US006833348B1

(12) United States Patent
Riccardi

(10) Patent No.: US 6,833,348 B1
(45) Date of Patent: Dec. 21, 2004

(54) INTRACELLULAR GLUCOCORTICOID-INDUCED LEUCINE ZIPPERS MODULATORS OF APOPTIC CELL DEATH PATHWAYS

(75) Inventor: Carlo Riccardi, Perugia (IT)

(73) Assignee: Applied Research Systems Ars Holding N.V., Curacao (NL)

( * ) Notice: Subject to any disclaimer, the term of this patent is extended or adjusted under 35 U.S.C. 154(b) by 0 days.

(21) Appl. No.: 09/403,861

(22) PCT Filed: Apr. 27, 1998

(86) PCT No.: PCT/EP98/02490

§ 371 (c)(1), (2), (4) Date: Feb. 11, 2000

(87) PCT Pub. No.: WO98/49291

PCT Pub. Date: Nov. 5, 1998

(30) Foreign Application Priority Data

Apr. 28, 1997 (EP) .......................................... 97107033

(51) Int. Cl.[7] ........................ C07K 17/00; A61K 38/00

(52) U.S. Cl. .......................................... 514/2; 530/350

(58) Field of Search ...................... 514/2–12; 530/350; 536/23.1, 23.5; 435/69.1

(56) References Cited

PUBLICATIONS

Shibanuma et al. Journal of Biological Chemistry, (1992) vol. 267, No. 15, pp. 10219–10224.*

Barret et al. Biochemistry (1996) vol. 35, No. 30, pp. 9746–9753.*

Jay et al. Biochem. Biophys. res. Comm. (1996) vol. 222, No. 3, pp. 821–826.*

Shibanuma et al. Journal of Biological Chemistry, (1992) vol. 267, No. 15, pp. 10219–10224.*

Hermann et al. Journal of Virology, vol. 71, No. 8, Aug. 1997, pp. 5922–5931.*

Jay et al. Biochem. Biophys. res. Comm. (1996) vol. 222, No. 3, pp. 821–826.*

Barrett et al., Coordinate regulation of glucocorticoid receptor and c–jun gene expression is cell type–specific and exhibits differential hormonal sensitivity for down– and up–regulation, *Biochemistry* 35(30):9746–9753 (1996).

D'Adamio et al., A new dexamethasone–induced gene of the leucine zipper family protects T lymphocytes from TCR/CD3–activated cell death, *Immunity*, 7(6):803–812 (1997).

Feng et al., Glucocorticoid and progesterone inhibit involution and programmed cell death in the mouse mammary gland, *J. Cell Biol.*, 131(4):1095–1103 (1995).

Jay et al., Cloning of the human homologue of the TGF beta–stimulated clone 22 gene, *Biochem. Biophys. Res. Commun.*, 222(3):821–826 (1996).

Jehn et al., Gene regulation associated with apoptosis, *Crit. Rev. Eukaryot. Gene Expr.*, 7(1–2):179–193 (1997).

Kato et al., Inhibition by dexamethasone of human neutrophil apoptosis in vitro, *Nat Immun.*, 14(4):198–208 (1995).

King et al., A targeted glucocorticoid receptor antisense transgene increase thymocyte apoptosis and alters thymocyte development, *Immunity*, 3(5):647–656 (1995).

Ohta et al., Mechanism of apoptotic cell death of human gastric carcinoma cells mediated by transforming growth factor beta, *Biochem. J.*, 324 (Pt 3):777–782 (1997).

Sillard et al., A novel 77–residue peptide from porcine brain contains a leucine–zipper motif and is recoginzed by an antiserum to delta–sleep–inducing peptide, *Eur. J. Biochem.*, 216(2):429–436 (1993).

Shibanuma et al., Isolation of a gene encoding a putative leucine zipper structure that is induced by t ransforming growth factor beta 1 and other growth factors, *J. Biol. Chem.*, 267(15):10219–10224 (1992).

Vogel et al., hDIP–a potential transcriptional regulator related to murine TSC–22 and Drosophila shortsighted (shs)–is expressed in a large number of human tissues, *Biochim. Biophys. Acta*, 1309(3):200–204 (1996).

Yang et al., Fas and activation–induced Fas ligand mediate apoptosis of T cell hybridomas: inhibition of Fas ligand expression by retinoic acid and glucocorticoids, *J. Exp. Med.*, 181(5):1673–1682 (1995).

* cited by examiner

*Primary Examiner*—Janet L. Epps-Ford
(74) *Attorney, Agent, or Firm*—Browdy and Neimark, PLLC

(57) ABSTRACT

A DNA sequence encoding a glucocorticoid-induced leucine-zipper family related protein (GILR), isoforms, fragments or analogs thereof said GILR, isoforms, fragments or analogs thereof capable of inhibiting apoptosis and stimulating lymphocyte activity, GILR proteins, isoforms, analogs, fragments and derivatives thereof encoded by the aforesaid DNA sequence, their preparation and uses.

15 Claims, 20 Drawing Sheets

FIG. 2

```
1          CTGGCTGCTGTGGAGTTTGTGACATACTAGGTGACACCCTTGGAGTCACTTC
53    TCTTCAACTCCAGCTTAGAAGTGCCTGCCTGGCTCAGGGTCTGCACTGCAGCCTACTCCT
113   TGCTTCAGGGCCTGACTGCAACGCCAAAGCCTATCCTATAGCGGCAGCGCCAGCAGCCAC
173   TCAAACCAGCCACAGCTCCCCGGCAACCGAACCATGAACACCGAAATGTATCAGACCCCC
                                      MetAsnThrGluMetTyrGlnThrPro

233   ATGGAGGTGGCGGTCTATCAGCTGCACAATTTCTCCACCTCCTTCTTTTCTTCTCTGCTT
      MetGluValAlaValTyrGlnLeuHisAsnPheSerThrSerPhePheSerSerLeuLeu

293   GGAGGGGATGTGGTTTCCGTTAAACTGGATAACAGTGCCTCCGGAGCCAGTGTGGTGGCC
      GlyGlyAspValValSerValLysLeuAspAsnSerAlaSerGlyAlaSerValValAla

353   CTAGACAACAAGATTGAGCAGGCCATGGACCTCGTGAAGAACCACCTGATGTACGCTGTG
      LeuAspAsnLysIleGluGlnAlaMetAspLeuValLysAsnHisLeuMetTyrAlaVal

413   AGAGAGGAGGTGGAGGTCCTAAAGGAGCAGATTCGTGAGCTGCTTGAGAAGAACTCCCAG
      ArgGluGluValGluValLeuLysGluGlnIleArgGluLeuLeuGluLysAsnSerGln

473   CTGGAGCGCGAGAACACCCTCCTGAAGACGCTGGCAAGCCCCGAGCAACTGGAAAAGTTC
      LeuGluArgGluLeuThrLeuLeuLysThrLeuAlaSerProGluGlnLeuGluLysPhe

533   CAGTCCCGGCTGAGCCCTGAAGAGCCAGCACCTGAAGCCCCAGAAACCCCGGAAACCCCG
      GlnSerArgLeuSerProGluGluProAlaProGluAlaProGluThrProGluThrPro

593   GAAGCCCCTGGTGGTTCTGCGGTGTAAGTGGCTCTGTCCTTAGGGTGGCAGAGCCACAT
      GluAlaProGlyGlySerAlaVal *

653   CTTGTTCTACCTAGTTCTTTCCAGTTTGTTTTTGGCTCCCCAAGGGTCATCTCATGTGGA
713   GAACTTTACACCTAACATAGCTGGTGCCAAGAGATGTCCCAAGGACATGCCCATCTGGGT
773   CCACTCCAGTGACAGACCCCTGACAAAGAGCAGGTCTCTGGAGACTAAGTTGCATGGGGC
833   CTAGTAACACCAAGCCAGTGAGCCTGTCGTGTCACCGGGCCCTGGGGGCTCCCAGGGCTG
893   GGCAACTTAGTTACAGCTGACCAAGGAGAAAGTAGTTTTGAGATGTGATGCCAGTGTGCT
953   CCAGAAAGTGTAAGGGGTCTGTTTTTCATTTCCATGGACATCTTCCACAGCTTCACCTGA
1013  CAATGACTGTTCCTATGAAGAAGCCACTTGTGTTCTAAGCAGAAGCAACCTCTCTCTTCT
1073  TCCTCTGTCTTTTCCAGGCAGGGGCAGAGATGGGAGAGATTGAGCCAAATGAGCCTTCTG
1113  TTGGTTAATACTGTATAATGCATGGCTTTGTGCACAGCCCAGTGTGGGGTTACAGCTTTG
1193  GGATGACTGCTTATAAAGTTCTGTTTGGTTAGTATTGGCATCGTTTTTCTATATAGCCAT
1253  AATGCGTATATATACCCATAGGGCTAGATCTATATCTTAGGGTAGTGATGTATACATATA
1313  CACATACACCTACATGTTGAAGGGCCTAACCAGCTTTGGGAGTACTGACTGGTCTCTTAT
1373  CTCTTAAAGCTAAGTTTTTGACTGTGCTAATTTACCAAATTGATCCAGTTTGTCCTTTAG
1433  ATTAAATAAGACTCGATATGAGGGAGGGAGGGGAAGACCAGCCTCACAATGCGGCCACAG
1493  ATGCCTTGCTGCTGCAGTCCTCCCTGATCTGTCCACTGAAGACATGAAGTCCTCTTTTGA
1553  ATGCCAAACCCACCATTCATTGGTGCTGACTACATAGAATGGGGTTGAGAGAAGATCAGT
1613  TTGGACTTCACATTTTTGTTTTAAGTTTTAGGTTGTTTTTTTTTGGTTTTGTTTGTTTGT
1673  TTGTTTGTTTGTTTTTGTTTTTTGTTTTTCTTTTTTAAGTTCTTGTGGGGAAACTTTGGG
1733  GTTAATCAAAGGATGTAGTCCTGTGGTAGACCAGAGGAGTAACTAGTTTTGATCCTTTGG
1793  GGTGTGGAAAATGTACCCAGGAAGCTTGTGTAAGGAGGTTCTGTGACAGTGAACACTTTC
1853  CACTTTCTGACACCTCATCCTGCTGTACGACTCCAGGATTTGGATTTGGATTTTTCAAAT
1913  GTAGCTTGAAATTTCAATAAACTTTGCTCCTTTTTCTAAAAATAAAAAAAAAAAAAAAA
```

| | |
|---|---|
| GILR | L K E Q I R E L L E K N S Q L E R E N T L L K T L A |
| TSC-22 | L K E Q I K E L I E K N S Q L E Q E N D L L K T L A |
| GCN4 | L E D K V E E L L S K N Y H L E N E V A R L K K L V |
| CREB | L E N R V A V L E N Q N K T L I E E L K A L K D L Y |
| CREM | L E N R V A V L E N Q N K T L I E E L K A L K D L Y |
| c-jun | L E E K V K T L K A Q N S E L A S T A N M L R E Q V |

```
   1 AATTCGGGGGCCGTGGAGTTTGTGACATACGAGGTGACACCCCTCGAGTCACTTCCCTTC
  61 AACTCCAGCTGGAGCGCCTGCTTGGCTTTGGGTTCGTTCTGCAGCCTTCGCCCCGCTCCT
 121 AGCCTCAGGGCCGGACTCCAGCGCAGAGCCCAGCCCAGCGCAGCCTGCCAGCAGCCACCC
 181 AGCCGCCCAGCCGCCCAGCCCCGCACGAAACCCGGCCAGAGCTTCCTAGCAGCCCGAGCC
 241 ATGAACACCGAAATGTATCAGACCCCCATGGAGGTGGCGGTCTACCAGCTGCACAATTTC
     MetAsnThrGluMetTyrGlnThrProMetGluValAlaValTyrGlnLeuHisAsnPhe

 301 TCCATCTCCTTCTTCTCTTCTCTGCTTGGAGGGGATGTGGTTTCCGTTAAGCTGGACAAC
     SerIleSerPhePheSerSerLeuLeuGlyGlyAspValValSerValLysLeuAspAsn

 361 AGTGCCTCCGGAGCCAGCGTGGTGGCCATAGACAACAAGATCGAACAGGCCATGGATCTG
     SerAlaSerGlyAlaSerValValAlaIleAspAsnLysIleAspGlnAlaMetAspLeu

 421 GTGAAGAATCATCTGATGTATGCTGTGAGAGAGGAGGTGGAGATCCTGAAGGAGCAGATC
     ValLysAsnHisLeuMetTyrAlaValArgGluGluValGluIleLeuLysGluGlnIle

 481 CGAGAGCTGGTGGAGAAGAACTCCCAGCTAGAGCGTGAGAACACCCTGTTGAAGACCCTG
     ArgGluLeuValGluLysAsnSerGlnLeuGluArgGluAsnThrLeuLeuLysThrLeu

 541 GCAAGCCCAGAGCAGCTGGAGAAGTTCCAGTCCTGTCTGAGCCCTGAAGAGCCAGCTCCC
     AlaSerProGluGlnLeuGluLysPheGlnSerCysLeuSerProGluGluProAlaPro

 601 GAATCCCCACAAGTGCCCGAGGCCCCTGGTGGTTCTGCGGTGTAAGTGGCTCTGTCCTCA
     GluSerProGlnValProGluAlaProGlyGlySerAlaVal *

 661 GGGTGGGCAGAGCCACTAAACTTGTTTTACCTAGTTCTTTCCAGTTTGTTTTTGGCTCCC
 721 CAAGCATCATCTCACGAGGAGAACTTTACACCTAGCACAGCTGGTGCCAAGAGATGTCCT
 781 AAGGACATGGCCACCTGGGTCCACTCCAGCGACAGACCCCTGACAAGAGCAGGTCTCTGG
 841 AGGCTGAGTTGCATGGGGCCTAGTAACACCAAGCCAGTGAGCCTCTAATGCTACTGCGCC
 901 CTGGGGGCTCCCAGGGCCTGGGCAACTTAGCTGCAACTGGCAAAGGAGAAGGGTAGTTTG
 961 AGGTGTGACACCAGTTTGCTCCAGAAAGTTTAAGGGGTCTGTTTCTCATCTCCATGGACA
1021 TCTTCAACAGCTTCACCTGACAACGACTGTTCCTATGAAGAAGCCACTTGTGTTTTAAGC
1081 AGAGGCAACCTCTCTCTTCTCCTCTGTTTCGTGAAGGCAGGGGACACAGATGGGAGAGAT
1141 TGAGCCAAGTCAGCCTTCTGTTGGTTAATATGGTATAATGCATGGCTTTGTGCACAGCCC
1201 AGTGTGGGATTACAGCTTTGGGATGACCGCTTACAAAGTTCTGTTTGGTTAGTATTGGCA
1261 TAGTTTTTCTATATAGCCATAAATGCGTATATATACCCATAGGGCTAGATCTGTATCTTA
1321 GTGTAGCGATGTATACATATACACATCCACCTACATGTTGAAGGGCCTAACCAGCCTTGG
1381 GAGTATTGACTGGTCCCTTACCTCTTATGGCTAAGTCTTTGACTGTGTTCATTTACCAAG
1441 TTGACCCAGTTTGTCTTTTAGGTTAAGTAAGAACTCGAGAGTAAAGGCAAGGAGGGGGGC
1501 CAGCCTCTGAATGCGGCCACGGATGCCTTGCTGCTGCAACCCTTTCCCCAGCTGTCCACT
1561 GAAACGTGAAGTCCTGTTTTGAATGCCAAACCCACCATTCACTGGTGCTGACTACATAGA
1621 ATGGGTTGAGAGAAGATCAGTTTGGGCTTCACAGTGTCATTTGAAAAAGCGTTTTTGTTT
1681 TGTTTTGAATTATTGTGGAAAACTTTCAAGTGAACAGAAGGATGGTGTCCTACTGTGGAT
1741 GAGGGATGAACAAGGGGATGGCTTTGATCCAATGGAGCCTGGGAGGTGTGCCCAGAAAGC
1801 TTGTCTGTAGCGGGTTTTGTGAGAGTGAACACTTTCCACTTTTTGACACCTTATCCTGAT
1861 GTATGGTTCCAGGATTTGGATTTTGATTTTCCAAATGTAGCTTGAAATTTCAATAAACTT
1921 TGCTCTGTTTTTCTAAAAAATAAAAA
```

FIG. 14A

```
  1 ...CTGGCTGCTGTGGAGTTTGTGACATACTAGGTGACACCCTTGGAGTC 47
         ||  || |||||||||||||||||| ||||||||||| | |||||
  1 aattcgggggccgtggagtttgtgacatacgaggtgacacccctcgagtc 50
             .         .         .         .         .
 48 ACTTCTCTTCAACTCCAGCTTAGAAGTGCCTGCCTGGCTCAGGGTCTGCA 97
    ||||| ||||||||||||||  | || |||||| |||||  ||||  |
 51 acttcccttcaactccagct..ggagcgcctgcttggctttgggttcgtt 98
             .         .         .         .         .
 98 CTGCAGCCT.......ACTCCTTGCTTCAGGGCCTGACTGCAACGCCAAA 140
    |||||||||        ||||| || |||||||| |||| || |||  |
 99 ctgcagccttcgccccgctcctagcctcagggccggactccagcgcagag 148
             .         .         .         .         .
141 GCCTATCC..........................TATAGCGGCAGCGCCA 164
     ||   ||                               | || || |
149 cccagcccagcgcagcctgccagcagccacccagccgcccagccgcccag 198
             .         .         .         .         .
165 GCAGCCACTCAAACCAGCCACAGCTCCCCGGCA.ACCGAACCATGAACAC 213
     |   |||  || || |||| |||| ||  |||  |||| ||||||||||
199 ccccgcacgaaacccggccagagcttcctagcagcccgagccatgaacac 248
             .         .         .         .         .
214 CGAAATGTATCAGACCCCCATGGAGGTGGCGGTCTATCAGCTGCACAATT 263
    |||||||||||||||||||||||||||||||||||| |||||||||||||
249 cgaaatgtatcagacccccatggaggtggcggtctaccagctgcacaatt 298
             .         .         .         .         .
264 TCTCCACCTCCTTCTTTTCTTCTCTGCTTGGAGGGGATGTGGTTTCCGTT 313
    |||||| ||||||||| |||||||||||||||||||||||||||||||||
299 tctccatctccttcttctcttctctgcttggaggggatgtggtttccgtt 348
             .         .         .         .         .
314 AAACTGGATAACAGTGCCTCCGGAGCCAGTGTGGTGGCCCTAGACAACAA 363
    || ||||| |||||||||||||||||||| ||||||||| ||||||||||
349 aagctggacaacagtgcctccggagccagcgtggtggccatagacaacaa 398
             .         .         .         .         .
364 GATTGAGCAGGCCATGGACCTCGTGAAGAACCACCTGATGTACGCTGTGA 413
    ||| || ||||||||||| || |||||||| || |||||||| |||||||
399 gatcgaacaggccatggatctggtgaagaatcatctgatgtatgctgtga 448
             .         .         .         .         .
414 GAGAGGAGGTGGAGGTCCTAAAGGAGCAGATTCGTGAGCTGCTTGAGAAG 463
    |||||||||||||| |||| ||||||||||| || |||||| | ||||||
449 gagaggaggtggagatcctgaaggagcagatccgagagctggtggagaag 498
             .         .         .         .         .
464 AACTCCCAGCTGGAGCGCGAGAACACCCTCCTGAAGACGCTGGCAAGCCC 513
    ||||||||||| ||||| |||||||||||  ||||||| |||||||||||
499 aactcccagctagagcgtgagaacaccctgttgaagaccctggcaagccc 548
             .         .         .         .         .
514 CGAGCAACTGGAAAAGTTCCAGTCCCGGCTGAGCCCTGAAGAGCCAGCAC 563
     ||||| ||||| |||||||||||| | |||||||||||||||||||| |
549 agagcagctggagaagttccagtcctgtctgagccctgaagagccagctc 598
             .         .         .         .         .
564 CTGAAGCCCCAGAAACCCCGGAAACCCCGGAAGCCCCTGGTGGTTCTGCG 613
    | ||| |||||          ||   || || ||||||||||||||||||
599 ccgaatcccca.........caagtgcccgaggcccctggtggttctgcg 639
             .         .         .         .         .
```

FIG. 14B

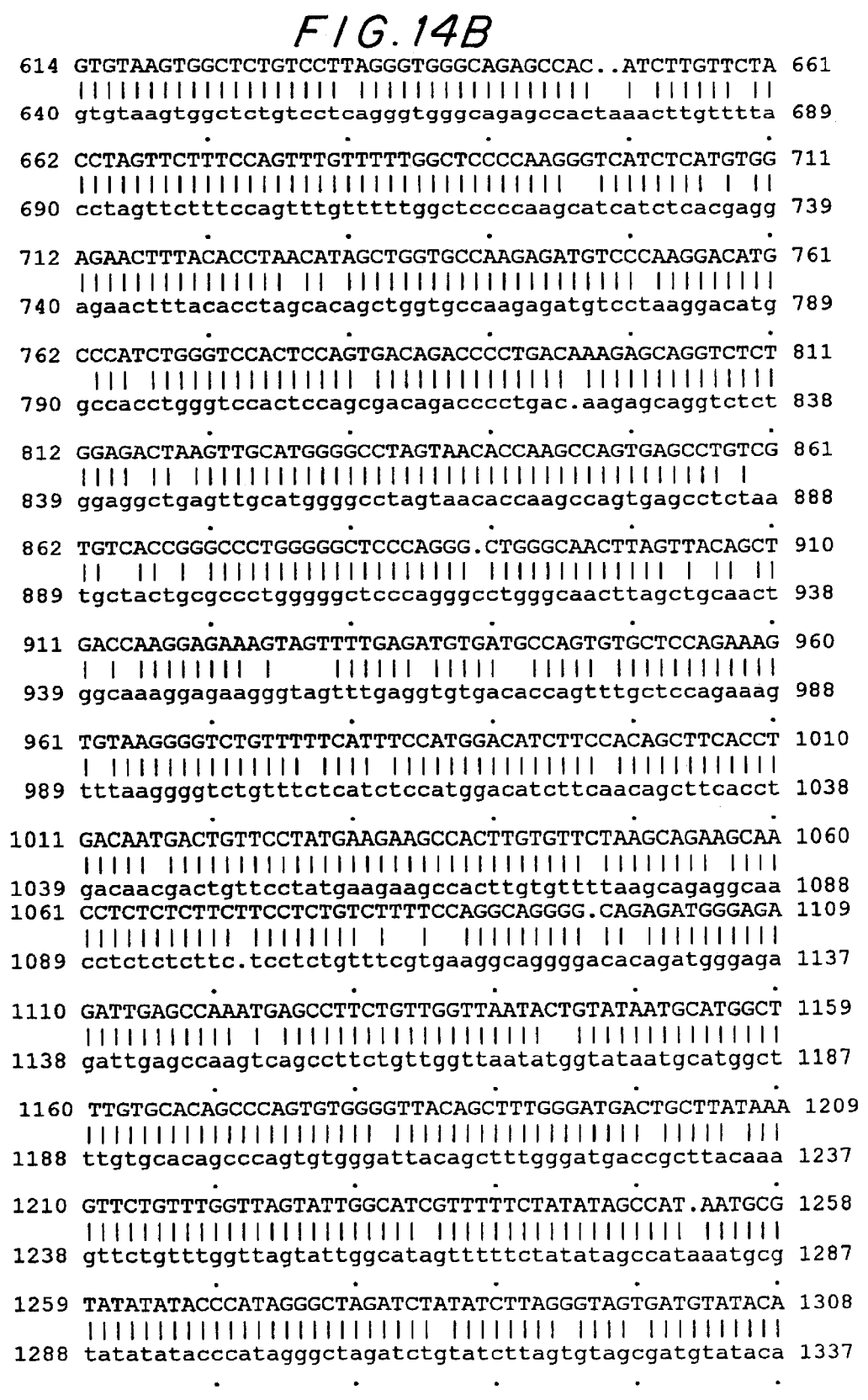

```
614  GTGTAAGTGGCTCTGTCCTTAGGGTGGGCAGAGCCAC..ATCTTGTTCTA  661
     ||||||||||||||||||| |||||||||||||||||  | |||||| ||
640  gtgtaagtggctctgtcctcagggtgggcagagccactaaacttgtttta  689

662  CCTAGTTCTTTCCAGTTTGTTTTTGGCTCCCCAAGGGTCATCTCATGTGG  711
     |||||||||||||||||||||||||||||||||||  |||||||| | ||
690  cctagttctttccagtttgtttttggctccccaagcatcatctcacgagg  739

712  AGAACTTTACACCTAACATAGCTGGTGCCAAGAGATGTCCCAAGGACATG  761
     ||||||||||||||| || ||||||||||||||||||||| |||||||||
740  agaactttacacctagcacagctggtgccaagagatgtcctaaggacatg  789

762  CCCATCTGGGTCCACTCCAGTGACAGACCCCTGACAAAGAGCAGGTCTCT  811
      ||| ||||||||||||||| |||||||||||||| ||||||||||||||
790  gccacctgggtccactccagcgacagacccctgac.aagagcaggtctct  838

812  GGAGACTAAGTTGCATGGGGCCTAGTAACACCAAGCCAGTGAGCCTGTCG  861
     |||| || |||||||||||||||||||||||||||||||||||||| |
839  ggaggctgagttgcatggggcctagtaacaccaagccagtgagcctctaa  888

862  TGTCACCGGGCCCTGGGGGCTCCCAGGG.CTGGGCAACTTAGTTACAGCT  910
     ||  || | ||||||||||||||||||| ||||||||||||| | || ||
889  tgctactgcgccctgggggctcccagggcctgggcaacttagctgcaact  938

911  GACCAAGGAGAAAGTAGTTTTGAGATGTGATGCCAGTGTGCTCCAGAAAG  960
     | | |||||||| |    |||||| |||||  ||||| ||||||||||||
939  ggcaaaggagaagggtagtttgaggtgtgacaccagtttgctccagaaag  988

961  TGTAAGGGGTCTGTTTTTCATTTCCATGGACATCTTCCACAGCTTCACCT  1010
     | |||||||||||||| |||| ||||||||||||||| ||||||||||||
989  tttaaggggtctgtttctcatctccatggacatcttcaacagcttcacct  1038

1011 GACAATGACTGTTCCTATGAAGAAGCCACTTGTGTTCTAAGCAGAAGCAA  1060
     ||||| |||||||||||||||||||||||||||||| |||||||| ||||
1039 gacaacgactgttcctatgaagaagccacttgtgttttaagcagaggcaa  1088
1061 CCTCTCTCTTCTTCCTCTGTCTTTTCCAGGCAGGGG.CAGAGATGGGAGA  1109
     ||||||||||| |||||||| |  |  ||||||||| || ||||||||||
1089 cctctctcttc.tcctctgtttcgtgaaggcaggggacacagatgggaga  1137

1110 GATTGAGCCAAATGAGCCTTCTGTTGGTTAATACTGTATAATGCATGGCT  1159
     ||||||||||| | |||||||||||||||||||  |||||||||||||||
1138 gattgagccaagtcagccttctgttggttaatatggtataatgcatggct  1187

1160 TTGTGCACAGCCCAGTGTGGGGTTACAGCTTTGGGATGACTGCTTATAAA  1209
     ||||||||||||||||||||| |||||||||||||||||| ||||| |||
1188 ttgtgcacagcccagtgtgggattacagctttgggatgaccgcttacaaa  1237

1210 GTTCTGTTTGGTTAGTATTGGCATCGTTTTTCTATATAGCCAT.AATGCG  1258
     |||||||||||||||||||||||| |||||||||||||||||| ||||||
1238 gttctgtttggttagtattggcatagtttttctatatagccataaatgcg  1287

1259 TATATATACCCATAGGGCTAGATCTATATCTTAGGGTAGTGATGTATACA  1308
     ||||||||||||||||||||||||| |||||||| |||| ||||||||||
1288 tatatatacccatagggctagatctgtatcttagtgtagcgatgtataca  1337
```

FIG. 14C

```
1309 TATACACATACACCTACATGTTGAAGGGCCTAACCAGCTTTGGGAGTACT 1358
     ||||||||| |||||||||||||||||||||||||||| ||||||||| |
1338 tatacacatccacctacatgttgaagggcctaaccagccttgggagtatt 1387
              .         .         .         .         .
1359 GACTGGTCTCTTATCTCTTAAAGCTAAGTTTTTGACTGTGCTAATTTACC 1408
     |||||||| |||| ||||||  ||||||| |||||||||| | |||||||
1388 gactggtcccttacctcttatggctaagtctttgactgtgttcatttacc 1437
              .         .         .         .         .
1409 AAATTGATCCAGTTTGTCCTTTAGATTAAATAAG.ACTCGATATGAGGGA 1457
     || |||| |||||||||| ||||| |||| |||| |||||| |  |  |
1438 aagttgacccagtttgtctttaggttaagtaagaactcgagagtaaagg 1487
              .         .         .         .         .
1458 GGGAGGGGAAGACCAGCCTCACAATGCGGCCACAGATGCCTTGCTGCTGC 1507
         | ||  | ||||||||  ||||||||||| ||||||||||||||||
1488 caaggaggggggccagcctctgaatgcggccacggatgccttgctgctgc 1537
              .         .         .         .         .
1508 AGTCC.TCCCTGATCTGTCCACTGAAGACATGAAGTCCTCTTTTGAATGC 1556
     |  || | ||  | |||||||||||| || ||||||||| ||||||||||
1538 aaccctttccccagctgtccactgaa.acgtgaagtcctgttttgaatgc 1586
              .         .         .         .         .
1557 CAAACCCACCATTCATTGGTGCTGACTACATAGAATGGGGTTGAGAGAAG 1606
     ||||||||||||||| |||||||||||||||||||| |||||||||||||
1587 caaacccaccattcactggtgctgactacatagaat.gggttgagagaag 1635
              .         .         .         .         .
1607 ATCAGTTTGGACTTCACATTTTTGTTTTAAGTTTTAGGTTGTTTTTTTTT 1656
     |||||||||| ||||||| | |  ||| ||     |    |||||| |||
1636 atcagtttgggcttcacagtgtcatttgaa.....aaagcgtttttgttt 1680
              .         .         .         .         .
1657 GGTTTTGTTTGTTTGTTTGTTTGTTTTTGTTTTTTGTTTTTCTTTT 1706
      ||||||  |  ||||
1681 tgttttgaattattgt.................................. 1696
              .         .         .         .         .
1707 TTAAGTTCTTGTGGGGAAACTTTGGGGTTAATCAAAGGATGTAGTCCTGT 1756
                  || |||||||   || ||    |||||||  |||||
1697 .............ggaaaactttcaagtgaacagaaggatggtgtcctac 1733
              .         .         .         .         .
1757 GGTAGACCAG......AGGAGTAACTAGTTTGATCCTTTGGGGTGTGGA 1800
      || ||  ||      |  ||    | | ||||||||   ||| |  |||
1734 tgtggatgagggatgaacaaggggatggctttgatccaatggagcctggg 1783
              .         .         .         .         .
1801 AAATGTACCCAGGAAGCTTGTGT.AAGGAGGTTCTGTGACAGTGAACACT 1849
     |  ||| ||||| |||||||| |  ||  |||| ||||| ||||||||||
1784 aggtgtgcccagaaagcttgtctgtagcgggttttgtgagagtgaacact 1833
              .         .         .         .         .
1850 TTCCACTTTCTGACACCTCATCCTGCTGTACGACTCCAGGATTTGGATTT 1899
     ||||||||| |||||||| |||||| |||| |  ||||||||||||||||
1834 ttccactttttgacaccttatcctgatgtatggttccaggatttggattt 1883
              .         .         .         .         .
1900 GGATTTTTCAAATGTAGCTTGAAATTTCAATAAACTTTGCTCCTTTTTCT 1949
      |||||| ||||||||||||||||||||||||||||||||||  ||||
1884 tgattttccaaatgtagcttgaaatttcaataaactttgctctgtttttc 1933
              .         .
1950 AAAAATAAAAAAAAAAAAAAAAA 1972
      |||| | |||||
1934 taaaaaataaaaa.......... 1946
```

FIG. 15

```
                                 .         .         .         .         .
mG     1 MNTEMYQTPMEVAVYQLHNFSTSFFSSLLGGDVVSVKLDNSASGASVVAL  50

hG     1 MNTEMYQTPMEVAVYQLHNFSISFFSSLLGGDVVSVKLDNSASGASVVAI  50
         ==================== ============================-

hT     2 KSQWCRPVAMDLGVYQLRHFSISFLSSLLGTENASVRLDNSSSGASVVAI  51
                  =---====  == == ===== -  ==-====-=======


                                 .         .         .         .         .
mG    51 DNKIEQAMDLVKNHLMYAVREEVEVLKEQIRELLEKNSQLERENTLLKTL 100

hG    51 DNKIEQAMDLVKNHLMYAVREEVEILKEQIRELVEKNSQLERENTLLKTL 100
         ========================-========-===============

hT    52 DNKIEQAMDLVKSHLMYAVREEVEVLKEQIKELIEKNSQLEQENNLLKTL 101
         ============ ================-==-=======-== =====

hD     1        MDLVKNHLMYAVREEVEILKEQIRELVEKNSQLERENTLLKTL  43
                =================-========-=======-========


                                 .         .         .
mG   101 ASPEQLEKFQSRLSPEEPAPEAPETPETPEAPGGSAV*            137

hG   101 ASPEQLEKFQSCLSPEEPAPES...PQVPEAPGGSAV*            134
         =========== =========-   =- =========

hT   102 ASPEQLAQFQAQLQTGSPPATTQPQGTTQPPAQPASQGSGPTA*      144
         ====== -==- =    =    -    =

hD    44 ASPEQLEKFQSCLSPEEPAPES...PQVPEAPGGSAV*             77
         ======-=== =========-   ============
```

INTRACELLULAR GLUCOCORTICOID-INDUCED LEUCINE ZIPPERS MODULATORS OF APOPTIC CELL DEATH PATHWAYS

CROSS REFERENCE TO RELATED APPLICATION

The present application is the national stage under 35 U.S.C. 371 of PCT/EP98/02490, filed Apr. 27, 1998.

FIELD OF THE INVENTION

The present invention is generally in the field of modulators of apoptopic cell death and uses thereof in therapeutic applications to inhibit or to enhance apoptosis, as desired depending on the disease and whether or not it is desired to kill the diseased cells or to rescue the diseased cells from apoptopic cell death. Specifically, the present invention concerns novel genes encoding novel proteins belonging to the leucine zipper family, which are capable of inhibiting apoptosis mediated by the CD3/TCR system or by the Fas/Fas-L system, and which are also capable of stimulating lymphocyte activation.

In particular, the present invention concerns a new protein and the gene encoding therefor called GILR, preparation and uses thereof, as well as any isoforms, analogs, fragments and derivatives of GILR, their preparation and uses.

BACKGROUND OF INVENTION AND PRIOR ART

Apoptosis (programmed cell death) is an important intracellular process having an important role in normal cell and tissue development as well as in the control of neoplastic growth (Cohen, 1993; Osborne and Schwartz, 1994; Wyllie et al., 1980; Kerr et al., 1972; Bursch et al., 1992).

A number of stimuli can either induce or inhibit programmed cell death through activation of molecules, involved in the signaling and execution of apoptosis, acting at different levels including the cell membrane, cytoplasm and nucleus. Among these, of note are those intracellular molecules, including some transcription factors, that have been shown to regulate cell growth. In particular, leucine zipper family proteins, such as for instance MYC, FOS and JUN, can modulate cell death (Shi et al., 1992; Smeyne et al., 1993; Goldstone and Lavin, 1994).

Apoptosis is also important in T-cell development (Dent et al., 1990; Ju et al., 1995; MacDonald and Lees, 1990). In particular, negative selection is due to apoptosis activated through the antigen (Ag) interaction with the T-cell-receptor (TCR)/CD3 complex (Smith et al., 1989). Engagement of the TCR/CD3 complex, either by APCs presenting antigenic peptide or by anti-CD3 antibody, triggers a series of activation events, such as for example, the expression of the Fas/Fas-Ligand (Fas/Fas-L) system, that can induce apoptosis in thymocytes, mature T cells and T cell hybridoma (Alderson et al., 1995; Dhein et al., 1995; Ju et al., 1995; Jenkinson et al., 1989; Webb et al., 1990; Yang et al., 1995). For example, triggering of such activation events in T cell hybridomas leads to cell cycle arrest, followed by apoptosis. This activation-induced cell death (AICD, Kabelitz et al., 1993) requires the interaction of Fas with Fas-L (Alderson et al., 1995; Itoh et al., 1991; Yang et al., 1995).

It has been shown that other stimuli, such as cytokines and glucocorticoid hormones (GCH), are also critical regulators of T-cell development (Migliorati et al., 1993; Nieto et al., 1990; Nieto and Lopez-Rivas, 1989; Cohen and Duke, 1984; Wyllie, 1980). For example, dexamethasone (DEX), a synthetic GCH which by itself induces apoptosis in T cell hybridomas and in normal T lymphocytes, can inhibit AICD induced by triggering of the TCR/CD3 complex (Zacharchuk et al., 1990). This inhibition may be due to prevention of activation induced expression of Fas and Fas-L (Yang et al., 1995).

With respect to the above noted Fas/Fas-L system, it should be noted that Fas has also been called the FAS receptor or FAS-R as well as CD95. For simplicity, this receptor will be called 'Fas' herein throughout and its ligand, as noted above, will be called 'Fas-L' herein throughout.

Fas is a member of the TNF/NGF superfamily of receptors and it shares homology with a number of cell-surface receptors including the p55-TNF receptor and the NGF receptor (see for example Boldin et al., 1995a and 1995b). Fas mediates cell death by apoptosis (Itoh et al. 1991) and appears to act as a negative selector of autoreactive T cells, i.e. during maturation of T-cells, Fas mediates the apoptopic death of T cells recognizing self-antigens. Mutations in the Fas gene, such as the lpr mutations in mice, have been shown to be responsible for a lymphoproliferation disorder in mice resembling the human autoimmune disease, systemic lupus erythomatosus (SLE; Watanabe-Fukunaga et al., 1992). The Fas-L molecule is apparently a cell surface-associated molecule carried by, amongst others, killer T cells (or cytotoxic T lymphocytes—CTLs), and hence, when such CTLs contact cells carrying Fas, they are capable of inducing apoptopic cell death of the Fas-carrying cells. Further, a monoclonal antibody specific to Fas has been prepared which is capable of inducing apoptopic cell death in cells carrying Fas, including mouse cells transformed by cDNA encoding human Fas (see, for example, Itoh et al, 1991).

While some of the cytotoxic effects of lymphocytes are mediated by interaction of lymphocyte-produced Fas-L with the widely-occurring Fas, it has also been found that various other normal cells besides T lymphocytes, express Fas on their surface and can be killed by the triggering of this receptor. Uncontrolled induction of such a killing process is suspected to contribute to tissue damage in certain diseases, for example, the destruction of liver cells in acute hepatitis. Accordingly, finding ways to restrain the cytotoxic activity of Fas may have therapeutic potential.

Conversely, since it has also been found that certain malignant cells and HIV-infected cells carry Fas on their surface, antibodies against Fas, or Fas-L itself, may be used to trigger Fas-mediated cytotoxic effects in these cells and thereby provide a means for combating such malignant cells or HIV-infected cells (see, for example, Itoh et al. 1991). Finding yet other ways for enhancing the cytotoxic activity of Fas may therefore also have therapeutic potential.

As noted above, Fas is related to one of the TNF receptors, namely, the p55-TNF receptor. TNF (both TNF-$\alpha$ and TNF-$\beta$, and as used throughout, 'TNF' will refer to both) has many effects on cells (see, for example, Wallach, D. (1986) In: Interferon 7 (Ion Gresser ed.), p. 83–122, Academic Press, London; and Beutler and Cerami (1987)).

TNF exerts its effects by binding to its receptors, the p55-TNF receptor and the p75-TNF receptor. Some of the TNF-induced effects are beneficial to the organism, such as, for example, destruction of tumor cells and virus-infected cells, and augmentation of antibacterial activities of granulocytes. In this way TNF contributes to the defense of the organism against tumors and infectious agents and contributes to recovery from injury.

Thus, TNF can be used as an anti-tumor and anti-infectious agent.

However, TNF can also have deleterious effects. For example, overproduction of TNF can have a pathogenic role in several diseases, including amongst others, septic shock (Tracey et al., 1986); excessive weight loss (cachexia); tissue damage in rheumatic diseases (Beutler and Cerami, 1987); tissue damage in graft-versus-host reactions (Piquet et al., 1987); and tissue damage in inflammation, to name but a few of the pathogenic effects of TNF.

The above cytocidal effects of TNF is mediated mainly by the p55-TNF receptor in most cells studied so far, which activity is dependent on the integrity of the intracellular domain of this receptor (see, for example, Brakebusch et al., 1992; Tartaglia et al., 1993). In addition, mutational studies indicate that the related Fas and p55 TNF-receptor mediate intracellular signaling processes, ultimately resulting in cell death, via distinct regions within their intracellular domains (see also, for example, Itoh and Nagata, 1993). These regions also designated 'death domains' present in both these receptors, have sequence similarity. The "death domains" of Fas and p55-TNF receptor are capable of self-association, which is apparently important for promoting the receptor aggregation necessary for initiating intracellular signaling (see, for example, Song et al. 1994; Wallach et al., 1994; Boldin et al., 1995a, b), and which, at high levels of receptor expression, can result in the triggering of ligand-independent signaling (Boldin et al., 1995a, b).

Recent studies have indicated that the cytotoxic effects mediated by Fas and p55-TNF receptor involves an intracellular signaling pathway which includes a number of protein-protein interactions, leading from the initial ligand-receptor binding to the eventual activation of enzymatic effector functions, and which include non-enzymatic protein-protein interactions which are involved in the initiation of the signaling for cell death (see also, for example, Nagata and Golstein, 1995; Vandenabeele et al., 1995; and Boldin et al., 1995a, b). Apparently the binding of the trimeric Fas-L and TNF to their receptors results in the interaction of the intracellular domains of these receptors which is augmented by a propensity of the death-domain regions or motifs to self-associate (Boldin et al., 1995a, b), and induced binding of at least two other cytoplasmatic proteins (which can also bind to each other) to the intracellular domains of these receptors, namely, the protein MORT-1 (also called FADD) which binds to Fas (see Boldin et al., 1995b; Chinnaiyan et al., 1995; Kischkel et al., 1995), and the protein TRADD which binds to the p55-TNF receptor (see Hsu et al., 1995; Hsu et al., 1996). A third such intracellular protein has also been identified called RIP (see Stanger et al., 1995) which binds to the intracellular domains of both Fas and the p55-TNF receptor. RIP can also interact with TRADD and MORT-1. Thus, these three intracellular proteins allow for a functional "cross-talk" between Fas and the p55-TNF receptor. The interactions between these receptors and their associated proteins (MORT-1, TRADD, RIP) occurs through the 'death domain' motifs present in each of these receptors and proteins.

Thus, the "death domain" motifs of the p55-TNF receptor and Fas as well as their three associated proteins MORT-1, RIP and TRADD appear to be the sites of protein-protein interactions. The three proteins MORT-1, RIP and TRADD interact with the p55-TNF receptor and Fas intracellular domains by the binding of their death domains to those of the receptors, and for both RIP and TRADD their death domains also self-associate, although MORT-1 differs in this respect in that its death domain does not self-associate. Accordingly, it would seem that the interaction between the three proteins MORT-1, RIP and TRADD is an important part of the overall modulation of the intracellular signaling mediated by these proteins. Interference of the interaction between these three intracellular proteins will result in modulation of the effects caused by this interaction. For example, inhibition of TRADD binding to MORT-1 may modulate the Fas-p55 TNF-receptor interaction. Likewise, inhibition of RIP in addition to the above inhibition of TRADD binding to MORT-1 may further modulate Fas-p55 TNF-receptor interaction.

Recent studies have also implicated a group of cytoplasmatic thiol proteases which are structurally related to the *Caenorhabditis elegans* protease CED3 and to the mammalian interleukin-1β converting enzyme (ICE) in the onset of various physiological cell death processes (reviewed in Kumar, 1995 and Henkart, 1996). There have also been some indications that protease(s) of this family may take part in the cell-cytotoxicity induced by Fas and TNF receptors. Specific peptide inhibitors of the proteases and two virus-encoded proteins that block their function, the cowpox protein crmA and the Baculovirus p35 protein, were found to provide protection to cells against this cell-cytotoxicity (Enari et al., 1995; Los et al., 1995; Tewari et al., 1995; Xue et al., 1995; Beidler et al., 1995). Rapid cleavage of certain specific cellular proteins, apparently mediated by protease(s) of the CED3/ICE family, could be demonstrated in cells shortly after stimulation of Fas or TNF receptors (both the p55-TNF receptor and the p75-TNF receptor).

One such protease and various isoforms thereof (including inhibitory ones), designated MACH which is a MORT-1 binding protein and which serves to modulate the activity of MORT-1 and hence of Fas and p55-TNF receptor, and which may also act independently of MORT-1, has been recently isolated, cloned, characterized, and its possible uses also described, as is set forth in detail in the international application No. PCT/US96/10521, and in a recent publication (Boldin et al., 1996). Another such protease and various isoforms thereof (including inhibitory ones), designated Mch4 has also recently been isolated and characterized (Fernandes-Alnemri et al., 1996; Srinivasula et al., 1996). This Mch4 protein is also a MORT-1 binding protein which serves to modulate the activity of MORT-1 and hence likely also of Fas and p55-TNF receptor and which may also act independently of MORT-1.

Moreover, it has also recently been found that besides the above noted cell cytotoxicity activities and modulation thereof mediated by the various receptors and their binding proteins including Fas, p55-TNF receptor, MORT-1, TRADD, RIP, MACH and Mch4, a number of these receptors and their binding proteins are also involved in the modulation of the activity of the nuclear transcription factor NF-κB, which is a key mediator of cell survival or viability, being responsible for the control of expression of many immune- and inflammatory-response genes. For example, it has been found that TNF-α can actually stimulate activation of NF-κB and thus TNF-α is capable of inducing two signals in cells, one eliciting cell death and another that protects cells against death induction by inducing gene expression via NF-κB (see Beg and Baltimore, 1996; Wang et al., 1996; Van Antwerp et al., 1996). A similar dual effect for Fas has also been reported (see reference to this effect as stated in above Van Antwerp et al., 1996). It would therefore appear that there exists a delicate balance between cell death and cell survival upon stimulation of various types of cells with TNF-α and/or the Fas-L, the ultimate outcome of the stimulation depending on which intracellular pathway is stimulated to a greater extent, the one leading to cell death (usually by apoptosis), or the one leading to cell survival via activation of NF-κB.

In addition, recently there has been further elucidated the possible pathway by which members of the TNF/NGF receptor family activate NF-κB (see Malinin et al., 1997 and the various relevant references set forth therein). Briefly, it arises that several members of the TNF/NGF receptor family are capable of activating NF-κB through a common adaptor protein, Traf2. A newly elucidated protein kinase called NIK (see above Malinin et al., 1997) is capable of binding to Traf2 and of stimulating NF-κB activity. In fact, it was shown (see aforesaid Malinin et al.) that expression in cells of kinase-deficient NIK mutants results in the cells being incapable of having stimulation of NF-κB in a normal endogenous manner and also in the cell having a block in induction of NF-κB activity by TNF, via either the p55-TNF receptor or Fas, and a block in NF-κB induction by TRADD, REP and MORT-1 (which are adaptor proteins that bind these p55-TNF and/or Fas receptors). All of the receptors p55-TNF and p75-TNF receptors and Fas, and their adaptor proteins MORT-1, TRADD and RIP bind directly or indirectly to Traf2, which by its binding ability to NIK apparently modulates the induction of NF-κB.

It has been a long felt need to provide a way for modulating the cellular response to Fas-L and to TNF. For example, in the pathological situations mentioned above, where Fas-L or TNF is overexpressed or otherwise present in excess amounts or where the Fas or, at least, p55-TNF receptor is over-activated or overexpressed, it would be desirable to inhibit the Fas-L or TNF-induced cytocidal effects, which in other situations, e.g. in tumor cells or wound healing applications, it would be desirable to enhance the TNF effect, or in the case of Fas, in tumor cells or HIV-infected cells, it would be desirable to enhance the Fas-mediated effect. To this end, a number of approaches have been attempted directed at the receptors themselves (to enhance or to inhibit their activity or amount, as the case may be) or directed at the signaling pathways, as noted above, in which these receptors or their associated proteins play a role (to enhance or inhibit the activities or amounts of the receptors or their associated proteins, as the case may be).

However, heretofore there has not been elucidated the role of glucocorticoid hormones (GCH) in the regulation of lymphocyte apoptosis, in particular, the role that GCH have in inducing gene expression, the product(s) of which may modulate apoptosis in T cells (and possibly other cells as well), which modulation may be by direct or indirect interaction with, or other means of modulation of, the Fas-mediated or the associated/related p55-TNF receptor-mediated intracellular signaling pathways leading to cell death (by apoptosis in which various proteases as noted above are involved) or leading to cell survival (via induction of NF-κB activation as noted above).

SUMMARY OF THE INVENTION

It is an object of the present invention to elucidate the role of glucocorticoid hormones (GCH) in the regulation of lymphocyte apoptosis, in particular, to elucidate the gene(s) or gene products(s) induced by GCH which can modulate apoptosis in T cells or in other cells. Hence, it is an object of the present invention to provide novel gene(s) which are induced by GCH, the product(s) of which can modulate apoptosis in T cells or other cells.

It is another object of the present invention to provide novel proteins, including all isoforms, analogs, fragments or derivatives thereof, which are encoded by the novel GCH-induced gene(s), which proteins, isoforms, analogs, fragments or derivatives can modulate apoptosis in T cells or in other cells. These new proteins, isoforms, analogs, fragments or derivatives may modulate apoptosis by modulating the signaling activity of Fas or the p55-TNF receptor intracellularly in a direct or indirect way, or may modulate apoptosis in an entirely Fas-independent and/or p55-TNF receptor-independent manner, by modulating the activity of other intracellular mediators of apoptosis. It should be understood that the modulation of apoptosis can be an enhancement/augmentation of apoptopic cell death or an inhibition of apoptopic cell death, these being the possible ways of direct modulation of apoptosis, be it via Fas- or p55-TNF-receptor-mediated pathways (inclusive of all the associated proteins/enzymes in these pathways as noted above) or via other pathways involving other intracellular mediators of apoptosis.

Indirect modulation of apoptosis is to be understood as, for example, induction by direct or indirect ways, of cell survival pathways (i.e. induction of NF-κB activation or other such cell survival-related pathways), which cell survival pathways essentially counteract apoptopic pathways.

Another object of the present invention is to provide antagonists (e.g. antibodies, peptides, organic compounds, or even some isoforms, analogs, fragments or derivatives) to the above new proteins, isoforms, analogs, fragments or derivatives thereof, which may be used to inhibit their activity in the intracellular signaling process in which they are involved, and hence to inhibit apoptosis, or conversely, to enhance apoptosis (inhibit cell-survival), as desired and depending on the activity of the protein, isoform, analogs, fragment or derivative, the activity of which is to be inhibited by the antagonist. For example, if a novel protein, isoform, analog, fragment or derivative of the invention is augmentory to apoptosis then such an antagonist would serve to block this augmentory role and ultimately block or reduce cell death via apoptosis. Likewise, if a novel protein, isoform, analog, fragment or derivative of the invention is inhibitory to apoptosis then such an antagonist would serve to block this inhibitory activity and ultimately enhance or augment apoptosis, i.e. result in increased cell death.

A further object of the present invention is to use the novel proteins, isoforms, analog, fragments and derivatives thereof, to isolate and characterize additional proteins or factors which may be involved in GCH-induced modulation of apoptosis (i.e. GCH-induced product(s) of gene expression capable of modulating apoptosis in T cells and other cells), which modulation may be as noted above. For example, other proteins may be isolated which may interact with the novel proteins of the invention and influence their activity, or other receptors or intracellular mediators further upstream or downstream in the signaling process(es) may be isolated with which the novel proteins of the present invention interact and hence in whose function the novel proteins of the invention are also involved.

Moreover, it is an object of the present invention to use the above-mentioned novel proteins, isoforms, analogs, fragments and derivatives as antigens for the preparation of polyclonal and/or monoclonal antibodies thereto. The antibodies, in turn, may be used, for example, for the purification of the new proteins from different sources, such as cell extracts or transformed cell lines. These antibodies may also be used for diagnostic purposes, for example, for identifying disorders related to abnormal functioning of cellular effects induced by GCH and/or mediated by the signaling processes in which the novel proteins of the invention play a role, such as, for example, the apoptopic pathways mediated by Fas and/or the p55-TNF receptor or cell survival pathways involving the induction of NF-κB activation, or any other such pathway in which such GCH-induced product(s) play a role.

A further object of the invention is to provide pharmaceutical compositions comprising the above novel proteins, isoforms, analogs, fragments or derivatives, as well as pharmaceutical compositions comprising the above noted antibodies or other antagonists.

In accordance with the present invention, a new gene and a new protein encoded by this gene have been identified and isolated. The new gene has been designated GILR (for: Glucocorticoid Induced Leucine-zipper family Related gene) which encodes a new member of the leucine zipper family. The designation GILR (Glucocorticoid Induced Leucine-Zipper gene) can be used as well as a synonymous. The mouse GILR protein is a protein of 137 amino acid residues characterized by having four leucine residues (at positions 76, 83, 90 and 97—see FIG. 2 and SEQ ID NO: 2) spanned by 7 amino acids and an asparagine residue (at position 87—see FIG. 2 and SEQ ID NO: 2) within the leucine zipper domain (see FIG. 4). The new GILR gene and the product it encodes, being the new GILR protein, were identified and isolated following dexamethasone (DEX) treatment of cells. DEX is a well known glucocorticoid hormone and hence the GILR gene and GILR protein represent a new glucocorticoid-induced gene and protein, respectively. Further, it appears that the GILR gene is induced in thymocytes and peripheral T cells and is also found to be expressed in normal lymphocytes from the thymus, spleen and lymph nodes. Little or no expression of the GILR gene was detected in other non-lymphoid tissues including brain, kidney and liver.

Using the previously cloned murine GILR as a probe, the human homologue of GILR has been cloned and sequenced (see FIG. 13 and SEQ ID NO 5), demonstrating the high level of conservativity of this sequence.

With respect to the biological activity of the new GILR protein, the experimental results indicate that this protein has at least one important activity being its ability to selectively protect T cells from apoptosis. More specifically, GILR expression selectively protects T cells from apoptosis induced by treatment of the T cells with anti-CD3 monoclonal antibody (mAb) but not by treatment with other apoptopic stimuli. This specific anti-apoptopic effect correlates with the inhibition of Fas and Fas-L expression.

Accordingly, GILR expression may also serve to modulate, albeit indirectly, other intracellular pathways, as noted above, in which Fas is involved, for example, the apoptopic processes common to Fas and the p55-TNF receptor in which their associated proteins and enzymes (e.g. MORT-1, TRADD, RIP, MACH, Mch4) are involved, which ultimately cause cell death by apoptosis. GILR, by specifically inhibiting Fas and Fas-L expression may therefore also inhibit pathways in which Fas acts together with the p55-TNF receptor due to the 'cross-talk' between these receptors mediated by the above proteins which bind to both of these receptors. Thus, while GILR expression may serve to inhibit Fas and Fas-L expression in a direct fashion and to a marked extent, GILR expression may also serve to inhibit the p55-TNF receptor's intracellular signaling activity, albeit in an indirect way and possibly to a lesser extent. In addition, as noted above, Fas is also involved in induction of NF-κB activation and hence GILR expression which inhibits FAS expression can possibly also serve to reduce this activity of Fas, although with apparently less detrimental effects to the cells, as, primarily the block of Fas-mediated apoptosis would serve to save the cells from cell death to a greater extent than would NF-κB activation save the cells.

In view of the above-mentioned it also arises, for example, that when it is desired to kill cells, e.g. tumor or HIV-infected cells, then it would be desirable to inhibit GILR expression, whilst, conversely, when it is desired to protect cells, e.g. liver cells in hepatitis patients, then it would be desired to increase the expression of GILR or augment its activity. Other uses of GILR and the control of its expression will be set forth herein below in greater detail.

As is detailed herein below, by comparing untreated and DEX-treated cells (for example, murine thymocytes, although any mammalian thymocytes and/or peripheral T cells and/or other lymphocytes, such as those obtained from humans, may be used equally) by employing the subtraction probe technique, it was possible to identify, isolate and clone the new GILR gene of the present invention.

The novel GILR protein of the invention is, in view of the above-mentioned and as set forth herein below, a modulator of apoptosis in lymphocytes, in general, and is in particular apparently an inhibitor of Fas-(and Fas-L-)mediated apoptosis, especially in T-lymphocytes.

Sequencing of the new GILR gene and protein has revealed that these are novel as based on comparisons of the GILR nucleotide and amino acid sequences (see FIGS. 2 and 13) with known sequences in various databases.

These comparisons revealed some homology between these GILR sequences and any known sequences.

The proteins that show the higher degree of homology are hDIP (Vogel et al., 1996) and human TSC-22 (Jay et al., 1996) (FIG. 15). All contain a similar leucine zipper domain (FIG. 4). Both these protein have been poorly characterized as potential transcriptional factor with a widespread distribution among different tissues. In this regard, GILR shows clearly distinct expression profile and activity, as it will be demonstrated in the examples.

In summary, based on the above mentioned and also taking into account the biological properties of the leucine zipper family which GILR is a member, it arises that, in general, GILR may be used to stimulate lymphocyte activity and to rescue cells from apoptotic cell death. GILR may of course, also be used as a probe to isolate other molecules which bind to GILR and which may serve to modulate its activity or otherwise be involved in intracellular signaling processes.

Accordingly, the present invention provides a DNA sequence encoding a glucocorticoid-induced leucine-zipper family related protein (GILR), isoforms, fragments or analogs thereof, said GILR, isoforms, fragments or analogs thereof capable of inhibiting apoptosis and stimulating lymphocyte activity.

Embodiments of the DNA sequence of the invention include:

(a) a cDNA sequence derived from the coding region of a native GILR protein;

(b) DNA sequences capable of hybridization to a sequence of (a) under moderately stringent conditions and which encode a biologically active GILR protein; and (c) DNA sequences which are degenerate as a result of the genetic code to the DNA sequences defined in (a) and (b) and which encode a biologically active GILR protein.

Other embodiments of the above DNA sequence are sequences comprising at least part of the DNA sequence depicted in SEQ ID NO:1 and encoding at least one active GILR protein, isoform, analog or fragment; as well as a DNA sequence encoding a GILR protein, isoform, analog or fragment having at least part of the amino acid sequence depicted in SEQ ID NO: 2.

Further embodiments of the above DNA sequence are sequences comprising at least part of the DNA sequence depicted in SEQ ID NO:5 and encoding at least one active human GILR protein, isoform, analog or fragment; as well as a DNA sequence encoding a human GILR protein, isoform, analog or fragment having at least part of the amino acid sequence depicted in SEQ ID NO: 6.

The present invention also provides a vector comprising any one of the above DNA sequences.

The vectors of the present invention are capable of being expressed in a eukaryotic host cell, or of being expressed in a prokaryotic host cell.

Accordingly, the present invention also provides transformed eukaryotic or prokaryotic host cells containing any of the above vectors.

By another aspect of the invention, there is provided a GILR protein, isoform, fragment, functional analogs or derivatives thereof encoded by any of the above DNA sequences, said protein, isoform, fragment, analogs and derivatives thereof being capable of inhibiting apoptosis and stimulating lymphocyte activity.

Embodiments of the above proteins, etc. of the invention include a GILR protein, isoform, fragment, analogs and derivatives thereof, wherein said protein, isoform, analogs, fragments and derivatives have at least part of the amino acid sequence SEQ ID NO: 2. or of the aminoacid sequence SEQ ID NO: 6.

The present invention also provides for a method for producing the GILR protein, isoform, fragment, analogs or derivatives thereof, comprising growing the transformed host cells under conditions suitable for the expression of said protein, analogs or derivatives, effecting post-translational modifications as necessary for obtaining of said protein, fragments, analogs or derivatives and isolating said expressed protein, fragments, analogs or derivatives.

In another aspect, there is provided antibodies or active fragments or derivatives thereof, specific for the GILR protein, isoform, fragment, analogs or derivatives of the invention.

The above DNA sequences and GILR proteins, etc. encoded thereby of the invention have many possible uses, and accordingly the present invention also provides for the following methods. It must be stressed that other therapeutic uses of GILR, its isoforms, analogs, fragments and derivatives, as well as antibodies against it and other antagonists of GILR activity, e.g. peptides, are also envisioned within the scope of the present invention, as are set forth in the detailed description of the invention or as arise from the disclosure herein below. Accordingly the following are but representative of the various methods in accordance with the present invention:

(i) A method for the inhibition of apoptosis in cells, mediated by the Fas/Fas-L system, CD3/TCR system or other intracellular mediators of apoptosis, comprising treating said cells with one or more GILR proteins, isoforms, analogs, fragments or derivatives, wherein said treating of said cells comprises introducing into said cells said one or more proteins, isoforms, analogs, fragments or derivatives in a form suitable for intracellular introduction thereof, or introducing into said cells a DNA sequence encoding said one or more proteins, isoforms, analogs, fragments or derivatives in the form of a suitable vector carrying said sequence, said vector being capable of effecting the insertion of said sequence into said cells in a way that said sequence is expressed in said cells.

(ii) A method as in (i) above for the inhibition of apoptosis in cells, wherein said treating of cells comprises introducing into said cells a DNA sequence encoding said GILR protein, isoforms, analogs, fragments or derivatives in the form of a suitable vector carrying said sequence, said vector being capable of effecting the insertion of said sequence into said cells in a way that said sequence is expressed in said cells.

(iii) A method as in (i) or (ii) above wherein said treating of said cells is by transfection of said cells with a recombinant animal virus vector comprising the steps of:

(a) constructing a recombinant animal virus vector carrying a sequence encoding a viral surface protein (ligand) that is capable of binding to a specific cell surface receptor on the surface of said cells to be treated and a second sequence encoding a protein selected from the GILR protein, isoforms, analogs, fragments and derivatives, that when expressed in said cells is capable of inhibiting apoptosis; and (b) infecting said cells with said vector of (a).

(iv) A method for enhancing apoptosis in cells by inhibiting the activity if GILR proteins in said cells, comprising treating said cells with antibodies or active fragments or derivatives thereof, said treating being by application of a suitable composition containing said antibodies, active fragments or derivatives thereof to said cells.

(v) A method for enhancing apoptosis in cells by inhibiting the activity of GILR proteins in said cells, comprising treating said cells with an oligonucleotide sequence encoding an antisense sequence for at least part of the DNA sequence encoding a GILR protein, said oligonucleotide sequence being capable of blocking the expression of the GILR protein.

(vi) A method as in (v) above wherein said oligonucleotide sequence is introduced to said cells via a virus of (iii) above wherein said second sequence of said virus encodes said oligonucleotide sequence.

(vii) A method for treating tumor cells or HIV-infected cells or other diseased cells, to enhance apoptosis in said cells by inhibiting the activity of GILR proteins in said cells, comprising:

(a) constructing a recombinant animal virus vector carrying a sequence encoding a viral surface protein capable of binding to a specific tumor cell surface receptor or HIV-infected cell surface receptor or receptor carried by other diseased cells and a sequence encoding an inactive GILR mutant protein, said mutant protein, when expressed in said tumor, HIV-infected, or other diseased cell is capable of inhibiting the activity of normal endogenous GILR and enhancing apoptosis in said cells; and (b) infecting said tumor or HIV-infected cells or other diseased cells with said vector of (a).

(viii) A method for enhancing apoptosis in cells by inhibiting the activity of GILR proteins in said cells, comprising applying the ribozyme procedure in which a vector encoding a ribozyme sequence capable of interacting with a cellular mRNA sequence encoding a GILR protein, is introduced into said cells in a form that permits expression of said ribozyme sequence in said cells, and wherein when said ribozyme sequence is expressed in said cells it interacts with said cellular mRNA sequence and cleaves said mRNA sequence resulting in the inhibition of expression of said GILR protein in said cells.

(ix) A method for enhancing apoptosis in cells by inhibiting the activity of GILR proteins in said cells, comprising introducing into said cells a peptide that is capable of binding the normal endogenous GILR in said cells and inhibiting its activity thereby enhancing apoptosis.

(x) A method for isolating and identifying proteins, which are GILR-like proteins belonging to the leucine zipper family or are proteins capable of binding directly to GILR, comprising applying the yeast two-hybrid procedure in which a sequence encoding said GILR is carried by one hybrid vector and sequence from a cDNA or genomic DNA library is carried by the second hybrid vector, the vectors then being used to transform yeast host cells and the positive transformed cells being isolated, followed by extraction of the said second hybrid vector to obtain a sequence encoding a protein which binds to said GILR.

(xi) A method as in any of the above wherein said protein is at least one of the GILR isoforms, analogs, fragments and derivatives thereof.

By yet another aspect of the present invention there are provided various pharmaceutical compositions, which are particularly useful for effecting at least some of the above methods of the invention. The following is therefore but a representative number of possible pharmaceutical compositions in accordance with the present invention, other possible compositions/formulations within the scope of the present invention are as set forth in the following detailed disclosure or as clearly arising therefrom:

a) a pharmaceutical composition for the inhibition of apoptosis in cells or for stimulating lymphocyte activation, comprising, as active ingredient, at least one GILR protein, its biologically active fragments, analogs, derivatives or mixtures thereof b) a pharmaceutical composition for inhibiting apoptosis in cells or for stimulating lymphocyte activation comprising, as active ingredient, a recombinant animal virus vector encoding a protein capable of binding a cell surface receptor and encoding at least one GILR protein, isoform, active fragments or analogs.

c) a pharmaceutical composition for enhancing apoptosis in cells by inhibiting GILR activity in said cells, comprising as active ingredient, an oligonucleotide sequence encoding an anti-sense sequence of the GILR protein mRNA sequence.

d) a pharmaceutical composition for enhancing apoptosis in cells by inhibiting GILR activity in said cells, comprising, as active ingredient, an inactive mutant GILR protein or DNA sequence encoding said inactive mutant GILR protein, which GILR mutant, when introduced into, or expressed in, said cells inhibits the activity of the normal endogenous GILR protein.

e) a pharmaceutical composition for enhancing apoptosis in cells by inhibiting GILR activity in said cells, comprising, as active ingredient, a peptide capable of binding to the active site or the leucine zipper domain of GILR and thereby inhibiting normal endogenous GILR activity in cells.

BRIEF DESCRIPTION OF THE DRAWINGS

FIG. 1 (A, B) shows reproductions of autoradiograms presenting the results of the analysis of GILR expression in various tissues and the effects of glucocorticoid induction (dexamethasone-DEX) induction of GILR expression in various tissues, wherein FIG. 1A, lanes 1 to 9: Spleen, Kidney, Bone Marrow, Heart, Liver, Brain, Lung Lymph nodes, Thymus. FIG. 1B, lanes 1 to 6: Lymph nodes, lymph nodes+DEX, Thymus, Thymus+DEX, Spleen, Spleen+DEX.

FIG. 2 depicts schematically the nucleotide (SEQ ID NO:1) and deduced polypeptide (amino acid (SEQ ID NO:2)) sequences of the mouse GILR gene and protein.

FIG. 3 (A, B, C) shows reproductions of autoradiograms presenting the results of the expression of GILR cDNA, wherein.

FIG. 4 is a schematic depiction of the comparison of the leucine zipper motif (residues 76–101 of SEQ ID NO:2) in the open reading frame of the urine GILR cDNA with those of other members of the leucine zipper family (SEQ ID NOS:7–11).

FIG. 9 (A, B) shows reproductions of autoradiograms presenting the expression of Fas mRNA in transfected clones wherein.

FIG. 10 (A, B) shows reproductions of autoradiograms presenting the results on the effect of different agents on the modulation of GILR mRNA expression, wherein

FIG. 11 (A, B) shows the results on the induction of GILR expression by anti-CD3 with or without Dexamethasone treatment. FIG. 1A shows a Western blot analysis of GILR protein in nuclear cell extracts of untreated thymocytes (lane 1), thymocytes cultivated on plates coated with anti-CD3 (1 μg/ml) for 3 hours (lane 2), thymocytes treated with 100 nM Dexamethasone for 3 hours (lane 3) and thymocytes cultivated on plates coated with anti-CD3 (1 μg/ml) for 3 hours and treated, for the same time, with 100 nM Dexamethasone. The amount of protein loaded in each lane is compared with an signal obtained with an antibody against β tubulin.

FIG. 11B is a protein immunoblot analysis of β tubulin protein in the same extracts.

FIG. 13 depicts schematically the nucleotide (SEQ ID NO:5) and deduced polypeptide (amino acid)(SEQ ID NO:6) sequences of the human GILR gene and protein FIG. 14 shows the comparison between mouse GILR (UPPERCASE) (SEQ ID NO:1) and human GILR (lowercase) (SEQ ID NO:5) cDNA sequence.

FIG. 15 shows the alignment of the protein sequences of mouse GILR (mG) (SEQ ID NO:2) compared to human GILR (hG) (SEQ ID NO:6), human DIP (hD;Vogel et al., 1996; accession number in Swiss-Prot Q99576) (SEQ ID NO:12) and human TSC-22 (hT; Jay et al., 1996; accession number in Swiss-Port Q15714) (SEQ ID NO:13). Residues which identical to mouse GILR are labelled with (=), meanwhile the residues which are homologous, are labelled with (–).

Figure 1A:
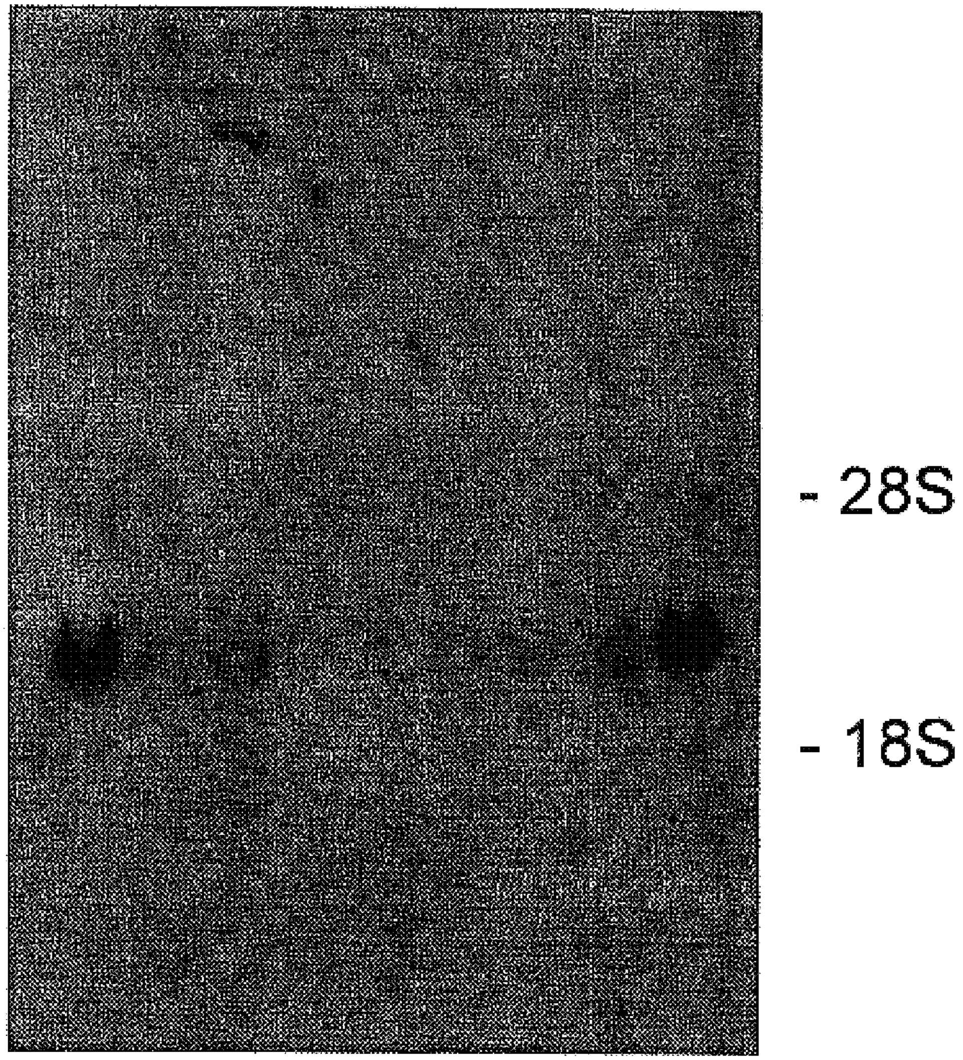
FIG. 1A shows the expression of GILR mRNA in mouse organs. Total RNA was extracted, separated on agarose gel and transferred to a nitrocellulose filter. The filter was hybridized with a nick-translation-labeled GILR cDNA probe, washed and autoradiographed and exposed for 8 days. Each lane was loaded with 2 μg of total RNA.

It should be noted that all of the above figures are also described and referred to in the Example herein below.

DETAILED DESCRIPTION OF THE INVENTION

In accordance with the present invention, a new member of the leucine zipper family, designated GILR, has been isolated. The cDNA encoding GILR has been identified, cloned, and sequenced and the protein encoded by this cDNA has been expressed, and its amino acid sequence has been deduced from the cDNA sequence. The GILR gene represents a gene whose transcription is regulated by glucocorticoid hormones (GCH) as evidenced by its induction by the synthetic GCH dexamethasone (DEX), and further represents such a GCH-regulated gene whose expression is involved in the modulation of T lymphocyte apoptosis.

The GILR protein (see FIGS. 2, 4 and 13) has good homology with all the other members of the leucine zipper family especially in the leucine zipper domain, including at least some homology with the protein TSC-22, whose function has not yet been defined, but which has also been shown to be induced by DEX-treatment (Shibanuma et al., 1992, Jay et al., 1996). Four leucine residues in GILR spanned by 7 amino acids (at positions 76, 83, 90 and 97) and an asparagine residue (at position 87) within the leucine zipper domain are compatible with the canonical leucine-zipper structure of the family.

However, like TSC-22, GILR does not seem to contain the canonical basic domain that is found in most transcription factors and is essential for binding to DNA.

Moreover, contrary to other leucine zipper molecules (Goldstone and Lavin, 1994; Hope and Struhl, 1987; Nicholas et al., 1991; Yamamoto et al., 1988), both TSC-22 and GILR, have a relatively small size (respectively 143 and 137 amino acids in total length) suggesting that these two may represent a new family of low molecular weight leucine zipper proteins. The GILR protein, moreover, has a domain, extended from residue 59 to residue 138 identical to protein hDIP (Vogel et al., 1996), whose function has not yet been defined.

The GILR mRNA is clearly detectable, by Northern blotting, in freshly isolated thymocytes, spleen and lymph node cells, and mRNA and protein expression is induced in lymphoid tissues such as thymocytes, spleen and lymph nodes, by treatment with DEX (see FIG. 1). Although these results may suggest that this gene is mainly expressed in T lymphocytes, the expression in other tissues, (including those in which there has been found low or no mRNA expression: bone marrow, heart, lung, liver, brain and kidney), cannot be excluded under peculiar contexts such as, for instance, during inflammatory processes and tissue regeneration or in the presence of tissue-specific signals. Anyway, the expression pattern of GILR is peculiar is compared to the more similar low molecular weight leucine zipper proteins: TSC-22 mRNA was detected, using Northern blot, fairly too ubiquitously among different tissue when its level was compared with that of tubulin in both mouse (Shibanuma et al., 1992) and human tissues (Jay et al., 1996), the analysis of hDIP gene expression pattern by combined Reverse Transcriptase-Polymerase Chain Reaction hybridization showed a significant expression of the hDIP gene at comparable level in each of the investigating tissues, comprising heart, lung, stomach, blood, pancreas and others (Vogel et al., 1996). The subcellular localization, as well, is different between GILR, which is clearly nuclear (FIG. 11) and TSC-22, which can be nuclear and cytoplasmatic (Shibanuma et al., 1992).

The results obtained following transfection experiments, indicate that the GILR gene is able to inhibit T-cell apoptosis induced by treatment with anti-CD3 mAb. On the contrary, the same transfected clones are protected only to a significantly lesser extent against the programmed cell death induced with other typical apoptotic agents such as DEX, UV irradiation, serum starvation or triggering of Fas by crosslinked anti-Fas mAb.

For example, DEX has previously been shown to induce apoptosis in T lymphocytes, including thymocytes and T cell hybridomas, as well as to inhibit cell death activated by triggering of the CD3/TCR complex (Cohen and Duke, 1984; Yang et al., 1995). These results indicate that GILR is specific in counteracting T-cell death activated by triggering of the CD3/TCR complex and could contribute in part to the DEX-induced inhibition of CD3/TCR-activated apoptosis.

Figure 8A:
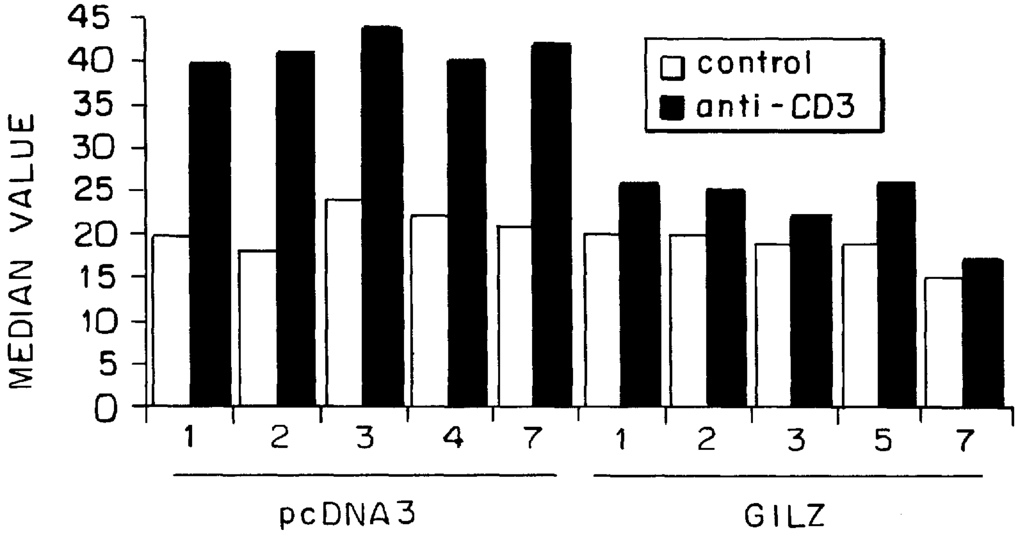
FIG. 8 (A, B) are bar-graph representations of the results of the Fas and Fas-L expression on 3DO transfected clones. 3DO cells transfected with empty vector or with GILR pcDNA3 were triggered with anti-CD3 mAb (1 μg/ml) for 20 hrs and analyzed for Fas (FIG. 8A) and Fas-L (FIG. 8B) expression.
Figure 8B:
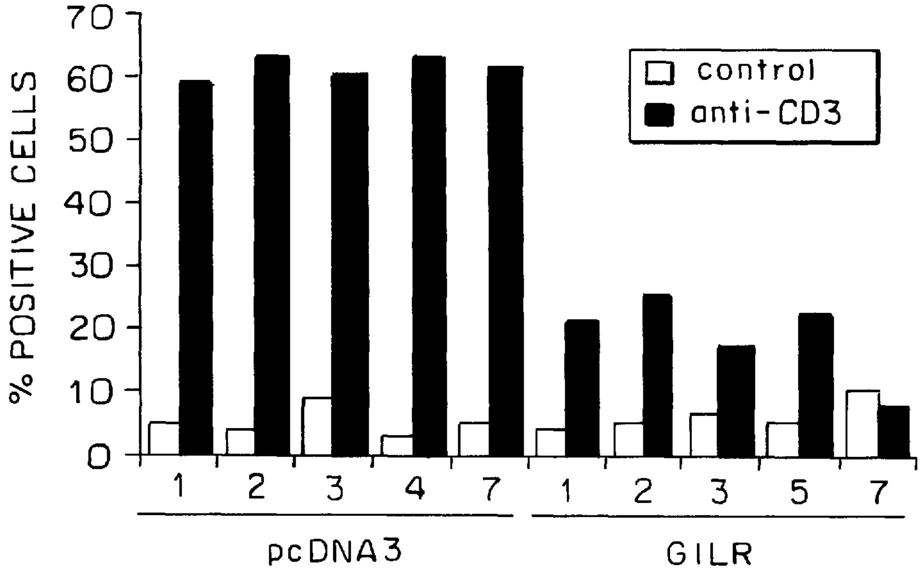
Figure 9A:
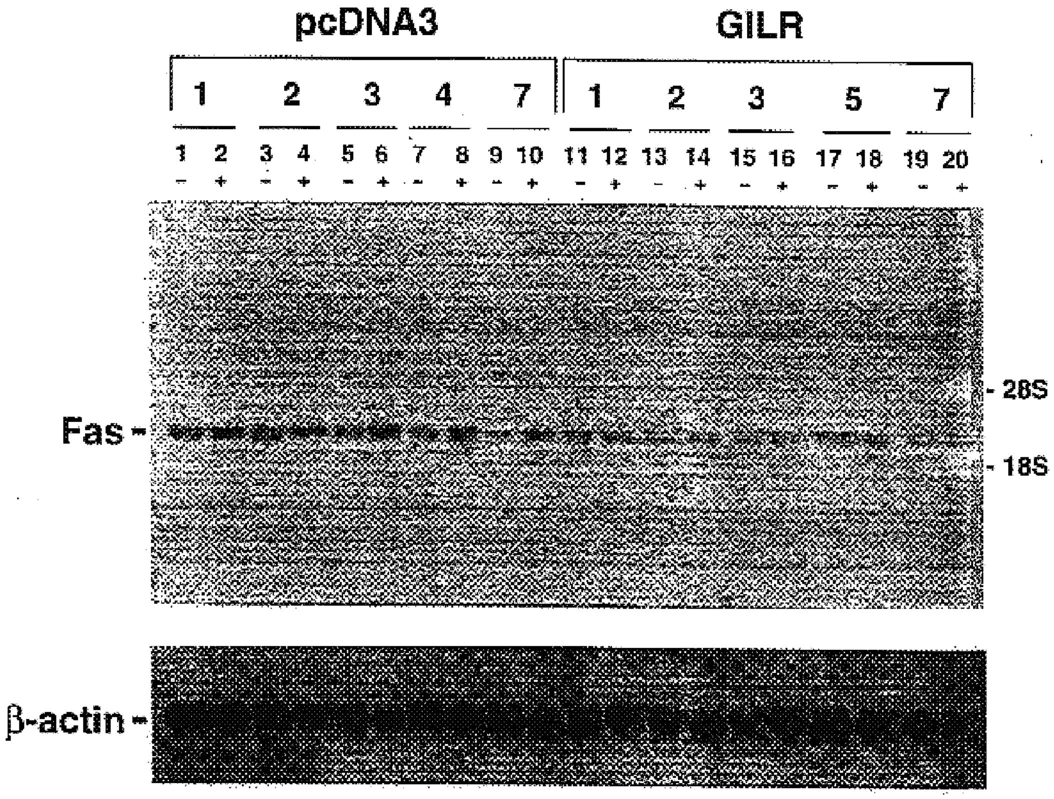
FIG. 9A shows the expression of Fas mRNA in clones transfected with empty pcDNA3 untreated (lanes 1, 3, 5, 7, 9), with empty pcDNA3 treated with anti-CD3 monoclonal antibody (1 μg/ml) for 20 hours (lanes 2, 4, 6, 8, 10), with GILR cDNA untreated (lanes 11, 13, 15, 17, 19) and with GILR cDNA treated with anti-CD3 monoclonal antibody (1 μg/ml) for 20 hours untreated (lanes 12, 14, 16, 18, 20).
Figure 9B:
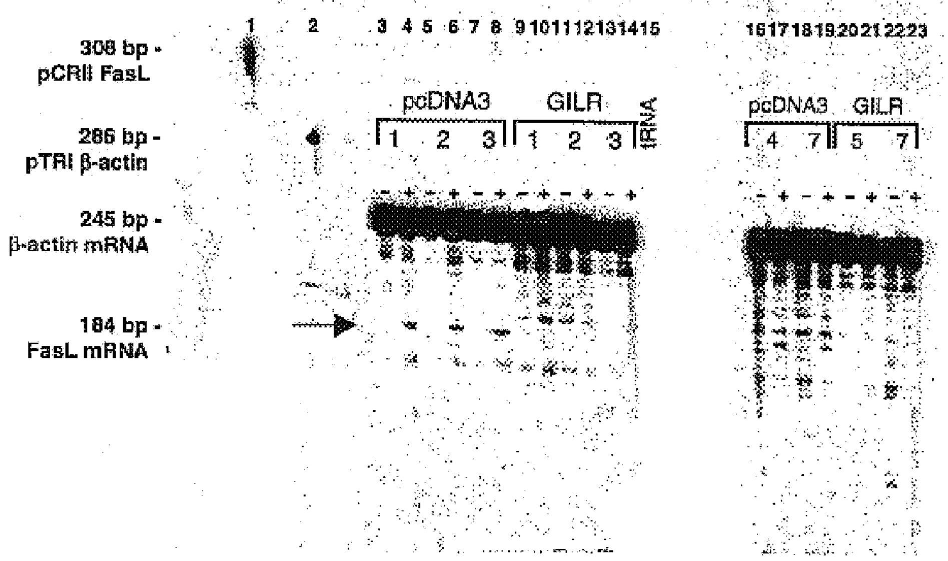
FIG. 9B shows the RNase protection analysis of FasL mRNA expression in the transfected clones. Fas-L (lane 1) or β-actin (lane 2) undigested probe; clones transfected with empty pcDNA3 untreated (lanes 3, 5, 7, 16, 18) or treated with anti-CD3 monoclonal antibody (1 μg/ml) for 20 hours (lanes 4, 6, 8, 17, 19) with GILR cDNA and untreated (lanes 9, 11, 13, 20, 22) and with GILR cDNA and then treated with anti-CD3 monoclonal antibody (1 μg/ml) for 20 hours (lanes 10, 12, 14, 21, 23); tRNA (lane 15). 20 μg RNA were loaded on each lane. The length of the protected antisense mRNA Fas-L fragment is 184 base pairs.

This protective effect raises the question about the possible mechanism(s) of GILR-induced inhibition of apoptosis. The present results indicate that the apoptosis inhibition, associated to GILR overexpression, correlates with the inhibition of Fas overexpression and Fas-L expression induced by treatment with anti-CD3 mAb (FIGS. 8, 9 and Table II). One possibility is that GILR interacts with other molecules, at the present unknown, which are involved in the activation of Fas and Fas-L gene expression.

GILR could interact either with signal(s), induced by TCR/CD3 triggering in activated lymphocytes, or directly with transcription factors involved in the regulation of Fas and Fas-L gene transcription.

Moreover, the increase of GILR expression, following DEX/T-cell interaction, suggests that this gene may be involved in regulating lymphocyte death. In fact, it has been suggested that GCH could participate in the regulation of T cell selection and contribute, together with other stimuli, (such as Ag/TCR interaction, cytokines and co-accessory molecules) in the complex selection network involved in the control of T-cell survival (Migliorati et al., 1993; Nieto et al., 1990; Nieto and Lopez-Rivas, 1989; Cohen and Duke, 1984; Wyllie, 1980).

The experimental results, in accordance with the present invention, thus describe the identification of a gene coding for a new molecule, GILR, of the Leucine zipper family which may be involved in the regulation of cell death.

The present invention therefore concerns, in one aspect, novel GILR proteins which are capable of mediating or modulating the intracellular Fas-mediated cell death or apoptosis pathway and possibly also cell survival pathways in which Fas plays a role as detailed herein above. This GILR appears to be an inhibitor of apoptosis activated by the triggering of the CD3/TCR complex as well as an inhibitor of Fas/Fas-L expression and as such GILR may play a key role in rescuing cells from cell death.

More particularly, in accordance with the present invention, a new protein GILR has been disclosed, which is involved in both the the cell death pathway intracellularly, and may also been involved in intracellular cell survival pathways. Hence, regulation or control of the activity of GILR can regulate either or both of these pathways or even the binding of TNF or Fas-ligand to their receptors (for TNF, the p55-R in particular), which are known to activate both cell death and cell survival pathways, the extent of activation of one pathway in comparison to the other possibly determining the final outcome of the, for example, CD3/TCR complex-, TNF-, or Fas-ligand-induced intracellular events, i.e. wheter the cell dies or survives. As GILR appears to directly effect (i.e. inhibit Fas/Fas-L expression it appears to be more directly related to protecting cells from cell death. Thus, the GILR protein of the present invention represents an important intracellular modulator or mediator, especially as regerds apoptosis.

Due to the unique ability of Fas, CD3/TCR and the TNF receptors to cause cell death, as well as the ability of the TNF receptors to trigger various other tissue-damaging activities, aberration of the function of these receptors can be particularly deleterious to the organism. Indeed, both excessive and deficient function of these receptors have been shown to contribute to the pathological manifestations of various diseases. Identifying molecules that take part in the regulation of the expression as well as the signaling activity of these receptors, and finding ways to modulate the function of these molecules, constitutes a potential clue for new therapeutical approaches to these diseases. In view of the suspected important role of GILR in Fas and possibly also p55-TNF receptor toxicity due to the inter-relationship or cross-talk between Fas and p55-TNF receptors, it seems particularly important to design drugs that can block the cytotoxic function of the Fas, CD3/TCR and other aforesaid mediators, possibly by way of increasing GILR expression or otherwise increasing the amounts of GILR. This would allow for the enhancement/augmentation of the rescue of cells from cell death in those pathological conditions where cell death should be reduced, e.g. in inflammation, various autoimmune diseases and the like where increased cell survival is sought.

Conversely, when it is desired to kill cells, for example cancer cells, HIV-infected cells and the like, it would be desirable to enhance the cytotoxic effects of Fas, CD3/TCR, p55-TNF receptor (and their associated proteins such as, for example, MORT-1, MACH, Mch4, TRADD), and this by reducing the expression or amounts of GILR.

It must be pointed out, though, that the presented experimental evidences on the GILR function (i.e. inhibition of T-cell apoptosis, specifically the one induced by treatment with anti-CD3 mAb and activated by the triggering of the CD3/TCR complex, as well as an inhibition of Fas/Fas-L expression) clearly differentiate GILR from the other elements of the same Leucine-zipper family. As more recently demonstrated, the transfection of a TSC-22 expression vector elicits the apoptotic cell death in a human gastric carcinoma cell line though the activation of TGF-β signalling pathway to apoptosis (Ohta et al., 1997).

The present invention also concerns the DNA sequence encoding a GILR protein and the GILR proteins encoded by the DNA sequences.

Moreover, the present invention further concerns the DNA sequences encoding biologically active isoforms, analogs, fragments and derivatives of the GILR protein, and the isoforms, analogs, fragments and derivatives encoded thereby. The preparation of such analogs, fragments and derivatives is by standard procedure (see for example, Sambrook et al., 1989) in which in the DNA sequences encoding the GILR protein, one or more codons may be deleted, added or substituted by another, to yield analogs having at least one amino acid residue change with respect to the native protein.

Of the above DNA sequences of the invention which encode a GILR protein, isoform, analog, fragment or derivative, there is also included, as an embodiment of the invention, DNA sequences capable of hybridizing with a cDNA sequence derived from the coding region of a native GILR protein, in which such hybridization is performed under moderately stringent conditions, and which hybridizable DNA sequences encode a biologically active GILR protein. These hybridizable DNA sequences therefore include DNA sequences which have a relatively high homology to the native GILR cDNA sequence and as such represent GILR-like sequences which may be, for example, naturally-derived sequences encoding the various GILR isoforms, or naturally-occurring sequences encoding proteins belonging to a group of GILR-like sequences encoding a protein having the activity of GILR. Further, these sequences may also, for example, include non-naturally occurring, synthetically produced sequences, that are similar to the native GILR cDNA sequence but incorporate a number of desired modifications. Such synthetic sequences therefore include all of the possible sequences encoding analogs, fragments and derivatives of GILR, all of which have the activity of GILR.

To obtain the various above noted naturally occurring GILR-like sequences, standard procedures of screening and isolation of naturally-derived DNA or RNA samples from various tissues may be employed using the natural GILR cDNA or portion thereof as probe (see for example standard procedures set forth in Sambrook et al., 1989).

Likewise, to prepare the above noted various synthetic GILR-like sequences encoding analogs, fragments or derivatives of GILR, a number of standard procedures may be used as are detailed herein below concerning the preparation of such analogs, fragments and derivatives.

A polypeptide or protein "substantially corresponding" to GILR protein includes not only GILR protein but also polypeptides or proteins that are analogs of GILR.

Analogs that substantially correspond to GILR protein are those polypeptides in which one or more amino acid of the GILR protein's amino acid sequence has been replaced with another amino acid, deleted and/or inserted, provided that the resulting protein exhibits substantially the same or higher biological activity as the GILR protein to which it corresponds.

In order to substantially correspond to GILR protein, the changes in the sequence of GILR proteins, such as isoforms are generally relatively minor. Although the number of changes may be more than ten, preferably there are no more than ten changes, more preferably no more than five, and most preferably no more than three such changes.

While any technique can be used to find potentially biologically active proteins which substantially correspond to GILR proteins, one such technique is the use of conventional mutagenesis techniques on the DNA encoding the protein, resulting in a few modifications. The proteins expressed by such clones can then be screened for their ability to bind to GILR and to modulate GILR activity in modulation/mediation of the intracellular pathways noted above.

"Conservative" changes are those changes which would not be expected to change the activity of the protein and are usually the first to be screened as these would not be expected to substantially change the size, charge or configuration of the protein and thus would not be expected to change the biological properties thereof.

Conservative substitutions of GILR proteins include an analog wherein at least one amino acid residue in the polypeptide has been conservatively replaced by a different amino acid. Such substitutions preferably are made in accordance with the following list as presented in Table A, which substitutions may be determined by routine experimentation to provide modified structural and functional properties of a synthesized polypeptide molecule while maintaining the biological activity characteristic of GILR protein.

TABLE A

| Original Residue | Exemplary Substitution |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Alternatively, another group of substitutions of GILR protein are those in which at least one amino acid residue in the polypeptide has been removed and a different residue inserted in its place according to the following Table B. The types of substitutions which may be made in the polypeptide may be based on analysis of the frequencies of amino acid changes between a homologous protein of different species, such as those presented in Table 1-2 of Schulz et al., G. E., Principles of Protein Structure Springer-Verlag, New York, N.Y., 1798, and FIGS. 3–9 of Creighton, T.E., Proteins: Structure and Molecular Properties, W. H. Freeman & Co., San Francisco, Calif. 1983. Based on such an analysis, alternative conservative substitutions are defined herein as exchanges within one of the following five groups:

TABLE B

| | |
|---|---|
| 1. | Small aliphatic, nonpolar or slightly polar residues: Ala, Ser, Thr (Pro, Gly); |
| 2. | Polar negatively charged residues and their amides: Asp, Asn, Glu, Gln; |
| 3. | Polar, positively charged residues: His, Arg, Lys; |
| 4. | Large aliphatic nonpolar residues: Met, Leu, Ile, Val (Cys); and |
| 5. | Large aromatic residues: Phe, Tyr, Trp. |

The three amino acid residues in parentheses above have special roles in protein architecture. Gly is the only residue lacking any side chain and thus imparts flexibility to the chain. This however tends to promote the formation of secondary structure other than a-helical. Pro, because of its unusual geometry, tightly constrains the chain and generally tends to promote β-turn-like structures, although in some cases Cys can be capable of participating in disulfide bond formation which is important in protein folding.

Note that Schulz et al., supra, would merge Groups 1 and 2, above. Note also that Tyr, because of its hydrogen bonding potential, has significant kinship with Ser, and Thr, etc.

Conservative amino acid substitutions according to the present invention, e.g., as presented above, are known in the art and would be expected to maintain biological and structural properties of the polypeptide after amino acid substitution. Most deletions and substitutions according to the present invention are those which do not produce radical changes in the characteristics of the protein or polypeptide molecule. "Characteristics" is defined in a non-inclusive manner to define both changes in secondary structure, e.g. a-helix or β-sheet, as well as changes in biological activity, e.g., inhibition of apoptosis mediated by CD3/TCR, Fas and other mediators, by GILR.

Examples of production of amino acid substitutions in proteins which can be used for obtaining analogs of GILR proteins for use in the present invention include any known method steps, such as presented in U.S. patent RE 33,653, U.S. Pat. Nos. 4,959,314, 4,588,585 and 4,737,462, to Mark et al.; U.S. Pat. No. 5,116,943 to Koths et al., U.S. Pat. No. 4,965,195 to Namen et al.; U.S. Pat. No. 4,879,111 to Chong et al.; and U.S. Pat. No. 5,017,691 to Lee et al.; and lysine substituted proteins presented in U.S. Pat. No. 4,904,584 (Shaw et al.).

Besides conservative substitutions discussed above which would not significantly change the activity of GILR protein, either conservative substitutions or less conservative and more random changes, which lead to an increase in biological activity of the analogs of GILR proteins, are intended to be within the scope of the invention.

When the exact effect of the substitution or deletion is to be confirmed, one skilled in the art will appreciate that the effect of the substitution(s), deletion(s), etc., will be evaluated by routine binding and cell death assays. Screening using such a standard test does not involve undue experimentation.

Acceptable GILR analogs are those which retain at least the capability of inhibiting apoptosis induced by CD3/TCR and/or Fas, or alternatively, those analogs which have no such inhibitory activity and serve rather as competitive antagonists of normal GILR molecules. Such antagonists are useful in situations where it is desired to enhance apoptosis.

In such a way, analogs can be produced which have a so-called dominant-negative effect, namely, an analog which is defective in inhibiting CD3/TCR-induced apoptosis or Fas/Fas-L expression. Further, analogs having a so called dominant-positive effect can be produced which have a greater than normal GILR capability for inhibiting apoptosis induced by CD3/TCR or Fas/Fas-L, these being particularly useful when it is desired to enhance cell survival in certain instances as noted above.

At the genetic level, these analogs are generally prepared by site-directed mutagenesis of nucleotides in the DNA encoding the GILR protein, thereby producing DNA encoding the analog, and thereafter synthesizing the DNA and expressing the polypeptide in recombinant cell culture. The analogs typically exhibit the same or increased qualitative biological activity as the naturally occurring protein, Ausubel et al., Current Protocols in Molecular Biology, Greene Publications and Wiley Interscience, New York, N.Y., 1987–1995; Sambrook et al., Molecular Cloning: A Laboratory Manual, Cold Spring Harbor Laboratory, Cold Spring Harbor, N.Y., 1989.

Preparation of a GILR protein in accordance herewith, or an alternative nucleotide sequence encoding the same polypeptide but differing from the natural sequence due to changes permitted by the known degeneracy of the genetic code, can be achieved by site-specific mutagenesis of DNA that encodes an earlier prepared analog or a native version of a GILR protein. Site-specific mutagenesis allows the production of analogs through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 complementing nucleotides on each side of the sequence being altered. In general, the technique of site-specific mutagenesis is well known in the art, as exemplified by publications such as Adelman et al., *DNA* 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., Third Cleveland Symposium on Macromolecules and Recombinant DNA, Editor A. Walton, Elsevier, Amsterdam (1981), the disclosure of which is incorporated herein by reference. These phage are readily available commercially and their use is generally well known to those skilled in the art. Alternatively, plasmid vectors that contain a single-stranded phage origin of replication (Veira et al., *Meth. Enzymol.* 153:3, 1987) may be employed to obtain single-stranded DNA.

In general, site-directed mutagenesis in accordance herewith is performed by first obtaining a single-stranded vector that includes within its sequence a DNA sequence that encodes the relevant polypeptide. An oligonucleotide primer bearing the desired mutated sequence is prepared synthetically by automated DNA/oligonucleotide synthesis. This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells, such as *E. coli* JM101 cells, and clones are selected that include recombinant vectors bearing the mutated sequence arrangement.

After such a clone is selected, the mutated GILR protein sequence may be removed and placed in an appropriate vector, generally a transfer or expression vector of the type that may be employed for transfection of an appropriate host.

Accordingly, gene or nucleic acid encoding for a GILR protein can also be detected, obtained and/or modified, in vitro, in situ and/or in vivo, by the use of known DNA or RNA amplification techniques, such as PCR and chemical oligonucleotide synthesis. PCR allows for the amplification (increase in number) of specific DNA sequences by repeated DNA polymerase reactions. This reaction can be used as a replacement for cloning; all that is required is a knowledge of the nucleic acid sequence.

In order to carry out PCR, primers are designed which are complementary to the sequence of interest. The primers are then generated by automated DNA synthesis.

Because primers can be designed to hybridize to any part of the gene, conditions can be created such that mismatches in complementary base pairing can be tolerated.

Amplification of these mismatched regions can lead to the synthesis of a mutagenized product resulting in the generation of a peptide with new properties (i.e., site directed mutagenesis). See also, e.g., Ausubel, supra, Ch. 16. Also, by coupling complementary DNA (cDNA) synthesis, using reverse transcriptase, with PCR, RNA can be used as the starting material for the synthesis of the extracellular domain of a prolactin receptor without cloning.

Furthermore, PCR primers can be designed to incorporate new restriction sites or other features such as termination codons at the ends of the gene segment to be amplified. This placement of restriction sites at the 5' and 3' ends of the amplified gene sequence allows for gene segments encoding GILR protein or a fragment thereof to be custom designed for ligation other sequences and/or cloning sites in vectors.

PCR and other methods of amplification of RNA and/or DNA are well known in the art and can be used according to the present invention without undue experimentation, based on the teaching and guidance presented herein. Known methods of DNA or RNA amplification include, but are not limited to polymerase chain reaction (PCR) and related amplification processes (see, e.g., U.S. Pat. Nos. 4,683,195, 4,683,202, 4,800,159, 4,965,188, to Mullis et al.; U.S. Pat. Nos. 4,795,699 and 4,921,794 to Tabor et al.; U.S. Pat. No. 5,142,033 to Innis; U.S. Pat. No. 5,122,464 to Wilson et al.; U.S. Pat. No. 5,091,310 to Innis; U.S. Pat. No. 5,066,584 to Gyllensten et al.; U.S. Pat. No. 4,889,818 to Gelfand et al.; U.S. Pat. No. 4,994,370 to Silver et al.; U.S. Pat. No. 4,766,067 to Biswas; U.S. Pat. No. 4,656,134 to Ringold; and Innis et al., eds., PCR Protocols: A Guide to Method and Applications) and RNA mediated amplification which uses anti-sense RNA to the target sequence as a template for double stranded DNA synthesis (U.S. Pat. No. 5,130,238 to Malek et al., with the tradename NASBA); and immuno-PCR which combines the use of DNA amplification with antibody labeling (Ruzicka et al., *Science* 260:487 (1993); Sano et al., *Science* 258:120 (1992); Sano et al., *Biotechniques* 9:1378 (1991), the entire contents of which patents and reference are entirely incorporated herein by reference.

In an analogous fashion, biologically active fragments of GILR proteins (e.g. those of any of the GILR or its isoforms) may be prepared as noted above with respect to the analogs of GILR proteins. Suitable fragments of GILR, proteins are those which retain the GILR activity as noted above. Accordingly, GILR protein fragments can be prepared which have a dominant-negative or a dominant-positive effect as noted above with respect to the analogs. It should be noted that these fragments represent a special class of the analogs of the invention, namely, they are defined portions of GILR proteins derived from the full GILR protein sequence (e.g., from that of any one of the GILR or its isoforms), each such portion or fragment having any of the above-noted desired activities. Such fragment may be, e.g., a peptide.

Similarly, derivatives may be prepared by standard modifications of the side groups of one or more amino acid residues of the GILR protein, its analogs or fragments, or by conjugation of the GILR protein, its analogs or fragments, to another molecule e.g. an antibody, enzyme, receptor, etc., as are well known in the art. Accordingly, "derivatives" as used herein covers derivatives which may be prepared from the functional groups which occur as side chains on the residues or the N- or C-terminal groups, by means known in the art, and are included in the invention. Derivatives may have chemical moieties such as carbohydrate or phosphate residues, provided such a fraction has the same or higher biological activity as GILR proteins.

For example, derivatives may include aliphatic esters of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aryl groups) or O-acyl derivatives of free hydroxyl group (for example that of seryl or threonyl residues) formed with acyl moieties.

The term "derivatives" is intended to include only those derivatives that do not change one amino acid to another of the twenty commonly occurring natural amino acids.

GILR is a protein or polypeptide, i.e. a sequence of amino acid residues. A polypeptide consisting of a larger sequence which includes the entire sequence of a GILR protein, in accordance with the definitions herein, is intended to be included within the scope of such a polypeptide as long as the additions do not affect the basic and novel characteristics of the invention, i.e., if they either retain or increase the biological activity of GILR protein or can be cleaved to leave a protein or polypeptide having the biological activity of GILR protein. Thus, for example, the present invention is intended to include fusion proteins of GILR protein with other amino acids or peptides.

The new GILR protein, their analogs, fragments and derivatives thereof, have a number of possible uses, for example:

(i) GILR protein, its isoforms, analogs, fragments and derivatives may be used to enhance/augment the inhibition of apoptosis mediated or induced by CD3/TCR, Fas/Fas-L, or any other related apoptosis mediators noted above. Such inhibition of apoptosis is particularly desirable in cases like, for example, tissue damage in septic shock, graft-versus-host rejection, acute hepatitis and various autoimmune and inflammatory diseases, in which it is desired to block apoptopic cell death mediated by Fas/Fas-L, CD3/TCR, or any other mediators. Thus, in view of the biological properties of the leucine zipper family to which GILR belongs and the functional knowledge of GILR itself, GILR, its isoforms, analogs, fragments or derivatives can be used to stimulate lymphocyte activity and enhance the rescue of cells from cell death by apoptosis.

This may be achieved by, for example, introducing GILR or any of its suitable isoforms, analogs, fragments or derivatives into cells by standard procedures known per se. Likewise, it is possible to construct a suitable fusion protein (this being one such GILR derivative) comprising the leucine zipper and/or praline-rich sequence of GILR and introducing this fusion protein into the cells by standard procedures, in which cells the fusion protein will exert its effect by, for example, interaction with other intracellular proteins, leading to enhanced inhibition of apoptosis.

To introduce the GILR protein, isoforms, analogs, fragments and derivatives (including the above fusion protein) into cells, there are a number of possible ways to do this: For example, it is preferable to introduce such GILR specifically into cells, such as T lymphocytes, in which the CD3/TCR and/or Fas/Fas-L systems are expressed and active in inducing apoptosis. One way of achieving this is to prepare a recombinant animal virus, e.g. one derived from Vaccinia, into which viral DNA will be introduced at least the following two genes: (i) the gene encoding a ligand that binds to cell surface proteins specifically expressed by the cells, e.g. ones present on the surface of T lymphocytes so that the recombinant virus vector will be capable of binding such T lymphocytes; and (ii) the GILR gene encoding the GILR protein. Thus, expression of the cell-surface binding protein (ligand) on the surface of the virus will target the virus specifically to the T lymphocytes, following which the GILR-encoding sequence will be introduced into the cells via the virus, and once so-expressed will inhibit apoptosis in these cells. In an analogous way encapsulated plasmids as are known in the art, may also be used for specific targeting of GILR-encoding plasmids/vectors to the cells in which the capsule allows for specificity of targeting and the plasmid DNA carries the GILR coding sequence to be expressed in the cells. Construction of such recombinant animal viruses or encapsulated plasmids are by standard procedures (see for example, Sambrook et al., 1989).

Another possibility of introducing DNA sequences encoding GILR including its isoforms, analogs, fragments and derivatives (including the above noted fusion proteins into cells is in the form of oligonucleotides which can be absorbed by the cells and expressed therein. Such a method is preferable when the cells to be treated, e.g. T lymphocytes, are treated in vitro with the aim of reintroducing such treated (rescued) cells back into the patient. Likewise, it is also possible to prepare, for example, a soluble GILR protein and introduce this into T cells in vitro, or to introduce the above noted viral vectors or encapsulate plasmids encoding GILR into T cells in vitro to bring about increased levels of GILR or GILR expression in these cells and then reintroduce them into the patient.

Similarly, for example, T lymphocytes can be treated in vivo or in vitro with a peptide mimicking GILR activity (e.g. inhibition of apoptosis) in these instances where it is desired to inhibit apoptosis, e.g. in inflammatory and autoimmune diseases, or acute hepatitis, or the like.

It should also be noted that proteins of the leucine zipper family to which GILR belongs, also appear to have the ability to stimulate lymphocyte activity (this being in addition to GILR ability to inhibit apoptosis). Thus, in certain situations where the activation of lymphocytes is more important than the inhibition of apoptosis, GILR may also be used to stimulate lymphocytes. For example, it has been found that in certain neoplastic (cancers) and immunodeficiency (including AIDS) diseases, there are unresponsive or low-level responsive T-lymphocytes in the patients, such as in various tumor-infiltrating T-lymphocytes. Thus, while it is desired to kill the tumor or HIV-infected cells by inducing increased apoptosis in these cells (e.g. by actually inhibiting GILR specifically in these diseased cells), it is however, not less desirable (if not more desirable) to specifically stimulate the activation of T-lymphocytes in these patients, which T-lymphocytes when activated may be more effective in combatting the tumor cells or overcoming the immunodeficiency caused by the HIV infection. Hence, in such situations it would be desirable to increase the amounts of GILR or GILR expression in such T lymphocytes in vivo or in vitro, which can be achieved by any of the ways noted above. T cells treated in vitro will then be transferred back into the patient.

This way of combatting diseased cells by stimulating lymphocytes has been used in other systems in which it was crucial to provide co-stimulation of T-cells. This approach of using GILR, its isoforms, analogs, fragments and derivatives to treat cells to stimulate T-cell activation and also, at the same time, to enable these cells to resist apoptosis (due to high GILR levels in the treated cells) is particularly useful in, for example, melanomas, in which the tumor cells kill cytotoxic T lymphocytes through the Fas/Fas-L system interaction.

Direct treatment of cells, other than T lymphocytes, with GILR, its isoforms, analogs, fragments or derivatives, either by in vitro or in vivo methods (the in vitro treatment followed by reintroduction of treated cells into the patient), in the various possible ways as noted above, is also important in various other diseases. For example, in acute hepatitis, liver cells die via apoptosis mediated by Fas/Fas-L system expression, which Fas/Fas-L system expression appears to induce and maintain the disease (see Galle et al., 1995). Increasing GILR levels or GILR expression specifically in these diseased liver cells should provide an effective way for treating this disease.

(ii) Conversely, in many instances it may be desirable to inhibit immune cell stimulation and to increase apoptopic cell death mediated by Fas/Fas-L, CD3/TCR or other mediators. For example, in various anti-tumor, anti-HIV, anti-inflammatory applications the diseased cells may be specifically killed by increasing the levels of induced apoptosis, e.g. increased Fas/Fas-L system expression. In such cases it would therefore be desirable to specifically inhibit GILR expression or levels in these cells, and in this way to reduce the inhibition of Fas/Fas-L system expression to provide, ultimately, higher levels of Fas/Fas-L system expression and higher levels of cell death via apoptosis.

To achieve inhibition of GILR expression or activity in such cells a number of possible ways exist: It is possible to introduce into the cells, by standard procedures, oligonucleotides having the anti-sense coding sequence for the GILR protein, which would effectively block translation of mRNAs encoding GILR, thereby blocking GILR expression and leading to increased levels of Fas/Fas-L system expression and apoptosis.

Such oligonucleotides may be introduced into the cells using the above recombinant virus approach, the second sequence carried by the virus being the oligonucleotide sequence.

Another possibility is to use antibodies specific for the GILR protein to inhibit its intracellular activity.

Yet another way of inhibiting the activity of GILR is by the recently developed ribozyme approach. Ribozymes are catalytic RNA molecules that specifically cleave RNAs. Ribozymes may be engineered to cleave target RNAs of choice, e.g., the mRNAs encoding the GILR protein of the invention. Such ribozymes would have a sequence specific for the GILR protein mRNA and would be capable of interacting therewith (complementary binding) followed by cleavage of the mRNA, resulting in a decrease (or complete loss) in the expression of the GILR protein, the level of decreased expression being dependent upon the level of ribozyme expression in the target cell. To introduce ribozymes into the cells of choice, any suitable vector may be used, e.g., plasmid, animal virus (retrovirus) vectors, that are usually used for this purpose (see also (i) above, where the virus has, as second sequence, a cDNA encoding the ribozyme sequence of choice). (For reviews, methods etc. concerning ribozymes see Chen et al., 1992; Zhao and Pick, 1993; Shore et al., 1993; Joseph and Burke, 1993; Shimayama et al., 1993; Cantor et al., 1993; Barinaga, 1993; Crisell et al., 1993 and Koizumi et al., 1993).

Moreover, to inhibit GILR expression, it is also possible to introduce, by the various ways noted above, a mutated GILR protein or DNA sequence encoding a mutated GILR, into cells, which mutated GILR would compete with normal GILR in these cells and effectively inhibit normal GILR activity.

Likewise it is also possible to inhibit GILR activity in cells by treating such cells with a peptide that binds the leucine zipper domain of GILR thus inhibiting the activity of GILR. Such a peptide may be prepared by standard means and introduced into the cells by standard procedures.

(iii) The GILR protein, its analogs, fragments or derivatives may also be used to isolate, identify and clone other proteins of the same class, i.e., those belonging to the leucine-zipper family or those which bind to GILR and which are involved in the intracellular signaling processes, e.g. inhibition of apoptosis. In this application the above noted (and detailed below in Example 1) subtraction probe technique may be used, or there may be used a recently developed system employing non-stringent Southern hybridization followed by PCR cloning (Wilks et al., 1989). In the Wilks et al. publication, there is described the identification and cloning of two putative protein-tyrosine kinases by application of non-stringent southern hybridization followed by cloning by PCR based on the known sequence of the kinase motif, a conceived kinase sequence. This approach may be used, in accordance with the present invention using the sequence of the GILR protein to identify and clone those of related proteins, including GILR-binding proteins. Likewise, the now standard and well known yeast-two hybrid system may be employed to specifically isolate and clone those proteins capable of specifically binding to GILR.

(iv) Yet another approach to utilizing the GILR protein, or its analogs, fragments or derivatives thereof, of the invention is to use them in methods of affinity chromatography to isolate and identify other proteins or factors to which they are capable of binding, e.g., other proteins or factors involved in the intracellular signaling process. In this application, the GILR protein, its analogs, fragments or derivatives thereof, of the present invention, may be individually attached to affinity chromatography matrices and then brought into contact with cell extracts or isolated proteins or factors suspected of being involved in the intracellular signaling process. Following the affinity chromatography procedure, the other proteins or factors which bind to the GILR protein, or its analogs, fragments or derivatives thereof of the invention, can be eluted, isolated and characterized.

(v) As noted above, the GILR protein, or its analogs, fragments or derivatives thereof, of the invention may also be used as immunogens (antigens) to produce specific antibodies thereto. These antibodies may also be used for the purposes of purification of the GILR protein (e.g., GILR or any of its isoforms) either from cell extracts or from transformed cell lines producing GILR protein, or its analogs or fragments. Further, these antibodies may be used for diagnostic purposes for identifying disorders related to abnormal functioning of the GILR protein.

It should also be noted that the isolation, identification and characterization of the GILR protein of the invention may be performed using any of the well known standard screening procedures. For example, one of these screening procedures, the subtraction probe technique was used as is set forth herein below. The yeast two-hybrid system may also be used (see, for example, Boldin et al., 1995a, b, and references therein). Likewise as noted above and below, other procedures may be employed such as affinity chromatography, DNA hybridization procedures, etc. as are well known in the art, to isolate, identify and characterize the GILR protein of the invention or to isolate, identify and characterize additional proteins, factors, receptors, etc. which are capable of binding to the GILR proteins of the invention.

As set forth hereinabove, the GILR protein may be used to generate antibodies specific to GILR proteins, e.g., GILR and its isoforms. These antibodies or fragments thereof may be used as set forth hereinbelow in detail, it being understood that in these applications the antibodies or fragments thereof are those specific for GILR proteins.

Based on the findings in accordance with the present invention that GILR is a modulator (inhibitor) of Fas/Fas-L expression and CD3/TCR system and can thus mediate/modulate cell death (apoptosis) pathways it is of importance to design drugs which may enhance or inhibit the GILR activity, as desired. There are many diseases in which such drugs can be of great help. Amongst others, acute hepatitis in which the acute damage to the liver seems to reflect Fas/Fas-L-mediated death of the liver cells; autoimmune-induced cell death such as the death of the β Langerhans cells of the pancreas, that results in diabetes; the death of cells in graft rejection (e.g., kidney, heart and liver); the death of oligodendrocytes in the brain in multiple sclerosis; and AIDS-inhibited T cell suicide which causes proliferation of the AIDS virus and hence the AIDS disease. In such cases it is desired to enhance GILR activity as noted above and in this way to block Fas/Fas-L activity and reduce cell death. However, in other cases as noted above it is desirable to block GILR activity in order to ultimately increase cell death.

With respect to such inhibitors, it is possible that one or more of the possible isoforms of GILR may serve as "natural" inhibitors of GILR activity and these may thus be employed as the above noted specific inhibitors of GILR. Likewise, mutant GILR proteins and other substances such as peptides, organic compounds, antibodies, etc. may also be screened to obtain specific drugs which are capable of inhibiting the activity of GILR, for example peptides capable of binding to the leucine zipper domain of GILR.

A non-limiting example of how peptide inhibitors of GILR would be designed and screened is based on previous studies on peptide inhibitors of ICE or ICE-like proteases, the substrate specificity of ICE and strategies for epitope analysis using peptide synthesis. The minimum requirement for efficient cleavage of peptide by ICE was found to involve four amino acids to the left of the cleavage site with a strong preference for aspartic acid in the $P_1$ position and with methylamine being sufficient to the right of the $P_1$ position (Sleath et al., 1990; Howard et al., 1991; Thornberry et al., 1992). Furthermore, the fluorogenic substrate peptide (a tetrapeptide), acetyl-Asp-Glu-Val-Asp-a-(4-methyl-coumaryl-7-amide) (SEQ ID NO:14) abbreviate Ac-DEVD-AMC, corresponds to a sequence in poly (ADP-ribose) polymerase (PARP) found to be cleaved in cells shortly after Fas stimulation, as well as other apoptopic processes (Kaufmann, 1989; Kaufmann et al., 1993; Lazebnik et al., 1994), and is cleaved effectively by CPP32 (a member of the CED3/ICE protease family) and MACH proteases.

As Asp in the $P_1$ position of the substrate appears to be important, tetrapeptides having Asp as the fourth amino acid residue and various combinations of amino acids in the first three residue positions can be rapidly screened for binding to the active site of the proteases using, for example, the method developed by Geysen (Geysen, 1985; Geysen et al., 1987) where a large number of peptides on solid supports were screened for specific interactions with antibodies. The binding of GILR to specific peptides can be detected by a variety of well known detection methods within the skill of those in the art, such as radiolabeling of the GILR, etc. This method of Geysen's was shown to be capable of testing at least 4000 peptides each working day.

In a similar way the exact binding region or region of homology which determines the active site of GILR or its leucine zipper domain can be elucidated and then peptides may be screened which can serve to block active site or domain, e.g. peptides synthesized having a sequence similar to that of the active site or zipper domain region or complementary thereto which can compete with natural GILR.

Since it may be advantageous to design peptide inhibitors that selectively inhibit GILR interactions without interfering with other physiological cell processes, the pool of peptides binding to GILR in an assay such as the one described above can be further synthesized as a fluorogenic substrate peptide to test for selective binding to other proteins to select only those specific for GILR. Peptides which are determined to be specific for GILR can then be modified to enhance cell permeability and enhance apoptosis by inhibiting GILR either reversibly or irreversibly. Thornberry et al. (1994) reported that a tetrapeptide (acyloxy) methyl ketone Ac-Tyr-Val-Ala-Asp-$CH_2OC$ (O)-[2,6-$(CF_3)_2$] Ph (SEQ ID NO:15) was a pot activator of ICE. Similarly, Milligan et al. (1995) reported that tetrapeptide inhibitors having a chloromethylketone (irreversibly) or aldehyde (reversibly) groups inhibited ICE. In addition, a benzyloxycarboxyl-Asp-$CH_2OC$ (O)-2,6-dichlorobenzene (DCB) was shown to inhibit ICE (Mashima et al., 1995). Accordingly, in an analogous way, tetrapeptides that selectively bind to GILR can be modified with, for example, an aldehyde group, chloromethylketone,(acyloxy) methyl ketone or a $CH_2OC$ (O)-DCB group to create a peptide inhibitor of GILR activity.

Further, to improve permeability, peptides can be, for example, chemically modified or derivatized to enhance their permeability across the cell membrane and facilitate the transport of such peptides through the membrane and into the cytoplasm.

Muranishi et al. (1991) reported derivatizing thyrotropin-releasing hormone with lauric acid to form a lipophilic lauroyl derivative with good penetration characteristics across cell membranes. Zacharia et al. (1991) also reported the oxidation of methionine to sulfoxide and the replacement of the peptide bond with its ketomethylene isoester ($COCH_2$) to facilitate transport of peptides through the cell membrane. These are just some of the known modifications and derivatives that are well within the skill of those in the art.

Furthermore, drug or peptide inhibitors, which are capable of inhibiting the activity of GILR and enhancing cell death via apoptosis can be conjugated or complexed with molecules that facilitate entry into the cell.

U.S. Pat. No. 5,149,782 discloses conjugating a molecule to be transported across the cell membrane with a membrane blending agent such as fusogenic polypeptides, ion-channel forming polypeptides, other membrane polypeptides, and long chain fatty acids, e.g. myristic acid, palmitic acid. These membrane blending agents insert the molecular conjugates into the lipid bilayer of cellular membranes and facilitate their entry into the cytoplasm.

Low et al., U.S. Pat. No. 5,108,921, reviews available methods for transmembrane delivery of molecules such as, but not limited to, proteins and nucleic acids by the mechanism of receptor mediated endocytotic activity. These receptor systems include those recognizing galactose, mannose, mannose 6-phosphate, transferrin, asialoglycoprotein, transcobalamin (vitamin $B_{12}$), $\alpha$-2 macroglobulins, insulin and other peptide growth factors such as epidermal growth factor (EGF). Low et al. teaches that nutrient receptors, such as receptors for biotin and folate, can be advantageously used to enhance transport across the cell membrane due to the location and multiplicity of biotin and folate receptors on the membrane surfaces of most cells and the associated receptor mediated transmembrane transport processes. Thus, a complex formed between a compound to be delivered into the cytoplasm and a ligand, such as biotin or folate, is contacted with a cell membrane bearing biotin or folate receptors to initiate the receptor mediated trans-membrane transport mechanism and thereby permit entry of the desired compound into the cell.

ICE is known to have the ability to tolerate liberal substitutions in the $P_2$ position and this tolerance to liberal substitutions was exploited to develop a potent and highly selective affinity label containing a biotin tag (Thornberry et al., 1994). Consequently, the $P_2$ position as well as possibly the N-terminus of the tetrapeptide inhibitor can be modified or derivatized, such as to with the addition of a biotin molecule, to enhance the permeability of these peptide inhibitors across the cell membrane.

In addition, it is known in the art that fusing a desired peptide sequence with a leader/signal peptide sequence to create a "chimerical peptide" will enable such a "chimerical peptide" to be transported across the cell membrane into the cytoplasm.

As will be appreciated by those of skill in the art of peptides, the peptide inhibitors of the GILR interaction according to the present invention is meant to include peptidomimetic drugs or inhibitors, which can also be rapidly screened for binding to GILR to design perhaps more stable inhibitors.

It will also be appreciated that the same means for facilitating or enhancing the transport of peptide inhibitors across cell membranes as discussed above are also applicable to the GILR or its isoforms themselves as well as other peptides and proteins derived therefrom, as noted above which exert their effects intracellularly.

As regards the antibodies mentioned herein throughout, the term 'antibody' is meant to include polyclonal antibodies, monoclonal antibodies' (in Abs), chimerical antibodies, anti-idiotypic (anti-Id) antibodies to antibodies that can be labeled in soluble or bound form, as well as fragments thereof provided by any known technique, such as, but not limited to enzymatic cleavage, peptide synthesis or recombinant techniques.

Polyclonal antibodies are heterogeneous populations of antibody molecules derived from the sera of animals immunized with an antigen. A monoclonal antibody contains a substantially homogeneous population of antibodies specific to antigens, which populations contains substantially similar epitope binding sites. MAbs may be obtained by methods known to those skilled in the art. See, for example Kohler and Milstein, *Nature,* 256:495–497 (1975); U.S. Pat. No. 4,376,110; Ausubel et al., eds., Harlow and Lane ANTIBODIES: A LABORATORY MANUAL, Cold Spring Harbor Laboratory (1988); and Colligan et al., eds., Current Protocols in Immunology, Greene Publishing Assoc. and Wiley Interscience N.Y., (1992–1996), the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of mAbs in vivo or in situ makes this the presently preferred method of production., Chimerical antibodies are molecules of which different portions are derived from different animal species, such as those having the variable region derived from a murine mab and a human immunoglobulin constant region. Chimerical antibodies are primarily used to reduce immunogenicity in application and to increase yields in production, for example, where murine mAbs have higher yields from hybridomas but higher immunogenicity in humans, such that human/murine chimerical mAbs are used. Chimerical antibodies and methods for their production are known in the art (Cabilly et al., *Proc. Natl. Acad. Sci. USA* 81:3273–3277 (1984); Morrison et al., *Proc. Natl. Acad. Sci. USA* 81:6851–6855 (1984); Boulianne et al., *Nature* 312:643–646 (1984); Cabilly et al., European Patent Application 125023 (published Nov. 14, 1984); Neuberger et al., *Nature* 314:268–270 (1985); Taniguchi et al., European Patent Application 171496 (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Sahagan et al., *J. Immunol.* 137:1066–1074 (1986); Robinson et al., International Patent Application No. WO8702671 (published May 7, 1987); Liu et al., *Proc. Natl. Acad Sci USA* 84:3439–3443 (1987); Sun et al., *Proc. Natl. Acad Sci USA* 84:214–218 (1987); Better et al., *Science* 240:1041–1043 (1988); and Harlow and Lane, ANTIBODIES:A LABORATORY MANUAL, supra. These references are entirely incorporated herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g. mouse strain) as the source of the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an “immunogen” to induce an immune response in yet another animal, producing a so-called anti-anti-ld antibody. The anti-anti-Id may be epitopically identical to the original mAb which induced the anti-Id.

Thus, by using antibodies to the idiotypic determinants of a mAb, it is possible to identify other clones expressing antibodies of identical specificity.

Accordingly, mAbs generated against the GILR proteins, analogs, fragments or derivatives thereof, of the present invention may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for an epitope of the above GILR protein, or analogs, fragments and derivatives thereof.

The anti-Id mAbs thus have their own idiotypic epitopes, or “idiotopes” structurally similar to the epitope being evaluated, such as GRB protein A.

The term “antibody” is also meant to include both intact molecules as well as fragments thereof, such as, for example, Fab and F(ab')2, which are capable of binding antigen. Fab and F(ab')2 fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')2 and other fragments of the antibodies useful in the present invention may be used for the detection and quantitation of the GILR protein according to the methods disclosed herein for intact antibody molecules. Such fragments are typically produced by proteolytic cleavage, using enzymes such as papain (to produce Fab fragments) or pepsin (to produce F(ab')2 fragments).

An antibody is said to be “capable of binding” a molecule if it is capable of specifically reacting with the molecule to thereby bind the molecule to the antibody. The term “epitope” is meant to refer to that portion of any molecule capable of being bound by an antibody which can also be recognized by that antibody. Epitopes or “antigenic determinants” usually consist of chemically active surface groupings of molecules such as amino acids or sugar side chains and have specific three dimensional structural characteristics as well as specific charge characteristics.

An “antigen” is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies, including fragments of antibodies, useful in the present invention may be used to quantitatively or qualitatively detect the GILR protein in a sample or to detect presence of cells which express the GILR protein of the present invention. This can be accomplished by immunofluorescence techniques employing a fluorescently labeled antibody (see below) coupled with light microscopic, flow cytometric, or fluorometric detection.

The antibodies (or fragments thereof) useful in the present invention may be employed histologically, as in immunofluorescence or immunoelectron microscopy, for in situ detection of the GILR protein of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the GILR protein, but also its distribution on the examined tissue.

Using the present invention, those of ordinary skill will readily perceive that any of wide variety of histological methods (such as staining procedures) can be modified in order to achieve such in situ detection.

Such assays for the GILR protein of the present invention typically comprises incubating a biological sample, such as a biological fluid, a tissue extract, freshly harvested cells such as lymphocytes or leukocytes, or cells which have been incubated in tissue culture, in the presence of a detectable labeled antibody capable of identifying the GILR protein, and detecting the antibody by any of a number of techniques well known in the art.

The biological sample may be treated with a solid phase support or carrier such as nitrocellulose, or other solid support or carrier which is capable of inmmobilizing cells, cell particles or soluble proteins. The support or carrier may then be washed with suitable buffers followed by treatment with a detectable labeled antibody in accordance with the present invention, as noted above. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Alternatively, the surface may be flat such as a sheet, test strip, etc.

Preferred supports or carriers include polystyrene beads. Those skilled in the art will know may other suitable carriers for binding antibody or antigen, or will be able to ascertain the same by use of routine experimentation.

The binding activity of a given lot of antibody, of the invention as noted above, may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an antibody in accordance with the present invention can be detectable labeled is by linking the same to an enzyme and used in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectable label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholin-esterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays.

For example, by radioactive labeling the antibodies or antibody fragments, it is possible to detect R-PTPase through the use of a radioimmunoassay (RIA). A good description of RIA may be found in Laboratory Techniques and Biochemistry in Molecular Biology, by Work, T.S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a g counter or a scintillation counter or by autoradiography.

It is also possible to label an antibody in accordance with the present invention with a fluorescent compound. When the fluorescently labeled antibody is exposed to light of the proper wavelength, its presence can be then detected due to fluorescence. Among the most commonly used fluorescent labeling compounds are fluorescein isothiocyanate, rhodamine, phycoerythrine, pycocyanin, allophycocyanin, o-phthaldehyde and fluorescamine.

The antibody can also be detectable labeled using fluorescence emitting metals such as $^{152}$E, or others of the lanthanide series. These metals can be attached to the antibody using such metal chelating groups as diethylenetriamine pentaacetic acid (ETPA).

The antibody can also be detectable labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemilumninescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectable labeled soluble antibody is added to permit detection and/or quantitation of the ternary complex formed between solid-phase antibody, antigen, and labeled antibody.

Typical, and preferred, immunometric assays include 'forward' assays in which the antibody bound to the solid phase is first contacted with the sample being tested to extract the antigen from the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

The GILR proteins of the invention may be produced by any standard recombinant DNA procedure (see for example, Sambrook, et al., 1989 and Ausubel et al., 1987–1995, supra) in which suitable eukaryotic or prokaryotic host cells well known in the art are transformed by appropriate eukaryotic or prokaryotic vectors containing the sequences encoding for the proteins. Accordingly, the present invention also concerns such expression vectors and transformed hosts for the production of the proteins of the invention. As mentioned above, these proteins also include their biologically active analogs, fragments and derivatives, and thus the vectors encoding them also include vectors encoding analogs and fragments of these proteins, and the transformed hosts include those producing such analogs and fragments. The derivatives of these proteins, produced by the transformed hosts, are the derivatives produced by standard modification of the proteins or their analogs or fragments.

The present invention also relates to pharmaceutical compositions comprising recombinant animal virus vectors encoding the GILR proteins, which vector also encodes a virus surface protein capable of binding specific target cell (e.g., lymphocytes, cancer cells, etc.) surface proteins to direct the insertion of the GILR protein sequences into the cells. Further pharmaceutical compositions of the invention comprises as the active ingredient (a) an oligonucleotide sequence encoding an anti-sense sequence of the GILR protein sequence, or (b) drugs that block the GILR activity.

Pharmaceutical compositions according to the present invention include a sufficient amount of the active ingredient to achieve its intended purpose. In addition, the pharmaceutical compositions may contain suitable pharmaceutically acceptable carriers comprising excipients and auxiliaries which facilitate processing of the active compounds into preparations which can be used pharmaceutically and which can stabilize such preparations for administration to the subject in need thereof as well known to those of skill in the art.

The invention will now be described in more detail in the following non-limiting Example and the accompanying drawings. It should be noted that all of the various procedures, unless otherwise indicated, are standard procedures of the art or are procedures readily apparent to all of skill in the art by virtue of their publication as noted in widely-available publications. Accordingly, all of the publications noted herein below, as well as those relevant publications noted herein above are included herein in their entirety, or at least as far as concerns the details to carry out the various procedures.

These procedures are thus to be construed as the full, enabling, disclosure of the same procedures used in accordance with the present invention as set forth in the following Example (Example 1). Likewise, all the various reagents, cells, etc. (i.e. 'materials') are also readily available to all of skill in the art by way of purchasing from the various manufacturers or by way of standard preparation thereof.

EXAMPLE 1

Identification, Isolation, Cloning and Characterization of the GILR Gene and the GILR Protein I. Materials and Methods a) Cells and Culture Conditions:

Thymocytes were obtained from 3 to 5-week-old C3H/HeN mice purchased from Charles River (Milan, Italy). The cell suspensions were washed, filtered and adjusted to a concentration of $8\times10^6$ cells/ml in complete medium. The cells were incubated at 37° C. alone or with 100 nM/l DEX (Sigma, St. Louis, Mo.) for 3 hrs. A CD3+, CD4+, CD2+, CD44+ sub-line obtained in our laboratory of the OVA-specific mouse hybridoma T cell line (3DO; Ayroldi et al., 1995) maintained in suspension in RPMI 1640 medium supplemented with 10% FCS and 10 μM HEPES buffer was used for transfection experiments. Cells were centrifuged at pre-established times at 200 g for 10 min, washed, and adjusted to the desired concentrations.

b) RNA Preparation:

Total cytoplasmatic RNA was isolated from thymocytes by using the protocol of Chirgwin (Chirgwin et al., 1979). Polyadenylated RNA was obtained as previously described (Maniatis et al., 1989).

c) Library Construction:

A directionally cloned cDNA library was constructed by using polyadenylated cytoplasmatic RNA from thymocytes cultured for 3 hours in the presence of DEX according to the Maniatis protocol (see Maniatis et al., 1989). Briefly, a first-strand cDNA was obtained with a reverse reaction using an oligo (dT) primer (10 μg) and 7 μg di-polyadenylated RNA. To monitor synthesis, 20 μCi [32P] dCTP (3000 Ci/mmol) was included in the reaction mixture. A second-strand cDNA was synthesized according to the procedures described by Gubler and Hoffman (Gubler and Hoffman, 1983). The cDNA was blunt-ended by using T4 polymerase (Behringer Mannheim, Mannheim, Germany) and then methylated with EcoRI methylase (Boehringer Mannheim). EcoRI linkers were ligated to the cDNA with T4 DNA ligase (New England Biolabs, Beverly, Mass.) at 16° C. for 12 hours. Following the ligation of linkers, the reaction was inactivated by heating to 68° C. and incubating at this temp. for 15 min. The cDNA suspension was precipitated in ethanol and purified on a CL4B column (Invitrogen BV, San Diego, Calif.).

The cDNA was inserted into λgt11 arms using EcoRI adaptors following the manufacture's protocol (Invitrogen). Recombinant clones (0.25×104 p.f.u./μl) were screened by hybridization with the subtraction probe (see below).

d) Subtraction Probe Procedure and Screening Library

To construct the subtracted probe, a biotinylated copy of the uninduced pool of mRNA (10 μg) and 32P-labeled cDNA from the induced mRNA (1 μg) were co-precipitated in ethanol. The precipitate was dried and dissolved in 2× hybridization buffer. The sample was heated at 100° C. for 1 minute and then incubated at 68° C. for 24 hours. To separate unhybridized from hybridized sequences, the reaction was diluted 10 to 15 times with streptavidin binding buffer and incubated with streptavidin for 10 minutes at room temperature. Two phenol-chloroform extractions were performed. After precipitation, the labeled cDNA probe was resuspended in 50 μl of sterile water and used directly as a subtraction probe for screening the cDNA library.

Mitrocellulose filters (Amersham Life Science International PLC, Buckinghamshire, England), with which there was obtained blotting plates containing 5×104 clones, were hybridized in 5×SSC, 5× Denhardt's solution, 1% SDS, 100 vg/vl tRNA (Sigma) and 20 mM sodium pyrophosphate (Ph 6.8) at 42° C. for 12 hours and the final wash was in 0.2×SSC, 0.1% SDS at 65° C. for 30 min.

e) Northern Blot Analysis

Indicated amounts (see 'Brief Description of the Drawings' above) of total cytoplasmatic RNA (ranging from 2 μg–25 μg RNA/lane on the gels, as noted with respect to the figures in 'Brief Description of the Drawings' herein above) were separated in 1.2% agarose gels and transferred to nitrocellulose filters (Scheicher and Schuell, Dassel, Germany). DNA probes were 32P-labeled using the nick-translation kit from Boehringer Mannheim and following manufacturer's instructions. Hybridization was carried out overnight. Filters were washed three times in 0.2×SSC with 0.5% SDS at 37° C. followed by two washes at 65° C.

f) Primer Extension Technique

The primer extension was performed according to the Maniatis procedure (Maniatis et al., 1989). The radiolabeled DNA primer (105 cpm), complementary to the sequence from the nucleotide at position 298 to the nucleotide at position 327 of GILR gene (see FIG. 2), was mixed with 20 μg mRNA from Dex-treated thymocytes for 3 hours.

g) DNA Sequence Determination cDNA clones were sequenced using $T_7$ DNA polymerase (Sequenase kit, US Biochemical Corp.) in conjunction with custom-synthesized 20- and 21-mer oligonucleotide primers (complementary to the cDNA sequence) and primers complementary to the plasmid cloning-site sequences. Overlapping sequences were obtained for both strands of the cDNA. cDNA sequences were derived from clones isolated from the screening of the cDNA library.

All sequence analysis and identification of structural motifs were done with the PC/Gene software program (Intelligenetics, Inc.). The most updated GenBank and EMBL nucleic acid data banks and the Swiss-Prot protein data bank were searched through the Internet network by using the FASTA program of Pearson and Lippman.

h) In Vitro Translation

RNA was translated in vitro using a rabbit reticulocyte lysate (Promega) by the procedure recommended by the manufacturer's instructions in the presence of [$^{35}$S] methionine (Amersham) and the products were analyzed by 15% SDS-PAGE. After electrophoresis, the gel was fixed and autoradiographed.

i) Preparation of Rabbit Anti-Mouse Antiserum and Western Blot Analysis

A rabbit polyclonal antiserum recognizing GILR was prepared with the se of a fusion protein containing the full GILR amino acid sequence fused to glutathione S-transferase (GST; Pharmacia). The GST-fusion protein was expressed in *Escherichia coli* (*E. coli*), induced with 1 mM isopropyl-β-D-thiogalactopyranoside (IPTG) and purified with glutathione (GSH)-agarose beads as described previously (Tan et al., 1994). This preparation was used to immunize New Zealand White rabbits (1 mg/rabbit).

After 4 weeks a booster injection of 0.2 mg of protein was given intravenously and blood was collected 1 week later for preparation of antiserum. The antiserum was purified using a fusion protein immobilized on nitrocellulose filter according to the Maniatis protocol (Maniatis et al., 1989). The antiserum was used for western blot analysis of proteins extracted from thymocytes treated with or without DEX, as previously described (Ayroldi et al., 1997) For Western blot, mouse thymocytes (5×10$^6$/sample) were lysed by incubating for 30 minutes on ice in 300 μl of lysis buffer (20 mM Tris-HCl, 0.15 NaCl, 5 mM EDTA, 100 mM PMSF, 2.5 mM Leupeptin, 2.5 mM Aprotinin). After centrifugation at 15,000 rpm for 15 minutes, the pellets were washed three times with cold lysis buffer, boiled for 3 minutes and then analyzed by electrophoresis in 10% SDS-PAGE gels followed by transfer to nitrocellulose (Bioblot-NC, Costar) for 5 hours at 250 mA at 4° C. in 25 mM Tris/glycine, ph 8.3 and 20% v/v methanol. Non-specific binding sites were blocked by immersing the membrane in 5% blocking reagent in Tris-buffered saline Tween (TBS-T) for 1 hour at room temperature.

The membranes were incubated with GILR polyclonal antiserum diluted 1:10000 1 hour at room temperature. After washing with TBS-T buffer, membranes were probed 1 hour at room temperature with HRP-labelled sheep anti-rabbit antibody diluted 1:5000 (Amersham), then incubated with ECL Western blotting reagents (Amersham) and exposed to hyperfilm-ECL (Amersham) for 15 seconds.

j) Transfections of Cultured Cells

The GILR cDNA coding sequence (874 bp—see FIG. 2) was cloned into a pcDNA3 plasmid (Invitrogen) for expression in mammalian cells. 3DO cells were transfected by electroporation (300 mA, 960 μF) with 15 μg of linearized pcDNA3 vector (control clones) or 15 μg linearized pcDNA3 vector expressing the GILR cDNA. 36 hours after transfection, the cells were cultured in medium containing 0.8 mg/gr G418 active-form (GIBCO-BRL, Life Technologies, Paisley, Scotland) and 100 μl of the cell suspension was plated in 96-wells plates (4 for each transfection). Following 15–20 days, no more than 15% of the wells had living growing cells. These surviving cells were considered clones and analyzed in an RNase protection assay for the expression of exogenous GILR (Vito et al., 1996).

k) RNase Protection Analysis (RPA)

Figure 5A:
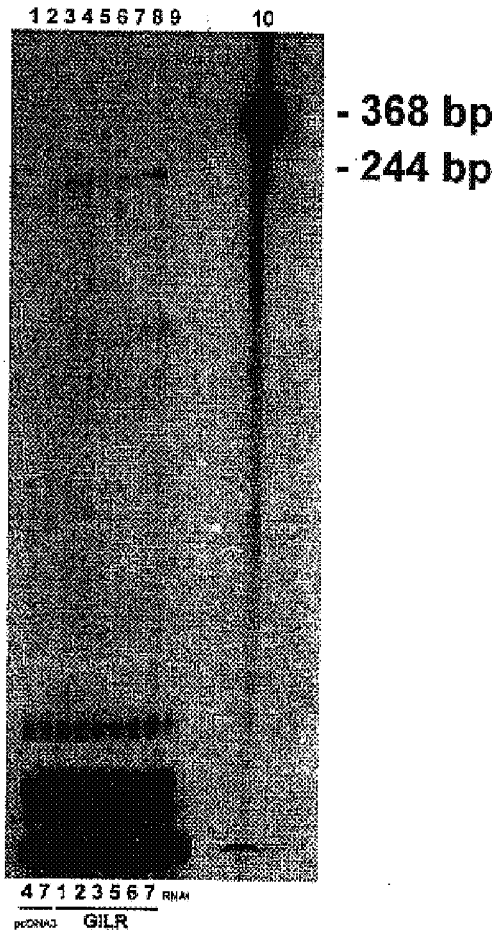
FIG. 5 (A, B, C) shows reproductions of autoradiograms presenting the results of the RNase protection analysis of GILR mRNA expression in transfected clones, wherein in FIG. 5A there is shown in lanes 1, 2, transfected clones with empty pcDNA3 controls; lanes 3–8, transfected clones with GILR cDNA; lane 9, tRNA control; lane 10, undigested probe control.
FIG. 5B shows in lane 1, undigested probe control; lanes 2–4, transfected clones with empty pcDNA3 controls; lanes 5–7, transfected clones with GILR cDNA; lane 8, tRNA control. 20 μg RNA was loaded on each lane.
FIG. 5C shows schematically the construct in which the fragment that the antisense probe would protect upon single-strand specific RNase digestion.
Figure 5B:
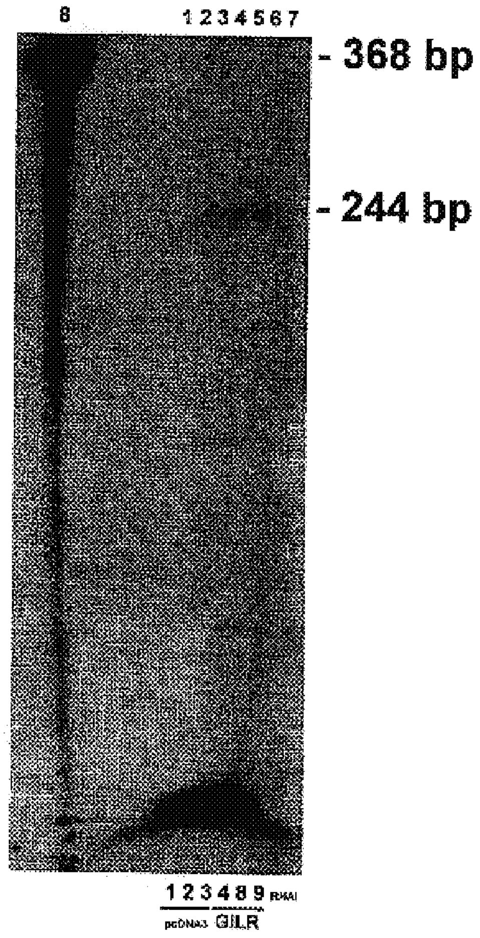
Figure 5C:
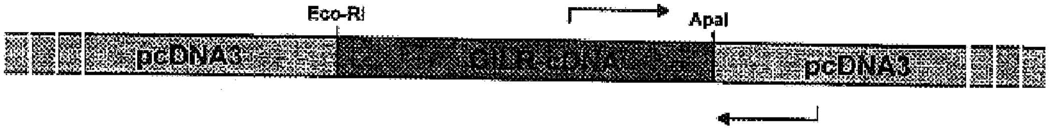

The probe for RPA was constructed by PCR using the Forward primer CCATCTGGGTCCACTCCAGT (located on GILR, 763–782 bp—see FIG. 2 and SEQ ID NO: 3) and the Reverse primer AGGACAGTGGGAGTGGCACC (located on pcDNA3—see FIG. 5C and SEQ ID NO: 4). The PCR product (244 bp) was cloned into a pCRII vector using the TA Cloning kit (Invitrogen). The product of this cloning was sequenced to exclude any possibility of a point mutation. Plasmid DNA was linearized with Xba I (New England Biolabs) and transcribed with $T_7$ RNA polymerase (GIBCO-BRL) in the presence of 50 μM [α32P]UTP. Following gel purification, the probe (2×105 cpm) was hybridized to total RNA (20 μg) overnight at 60° C. RNase digestion was performed by using a RNase A (Boehringer Mannheim) (40 μg/ml) and RNase $T_1$ (GIBCO-BRL) (1.5 U/μl) solution at 37° C. for 15 min. The undigested products were treated with phenol-chloroform, precipitated with ethanol and loaded onto a denaturing polyacrylamide sequencing gel. Autoradiographic exposure was carried out for 2 days.

l) Antibody Cross-Linking and Cell Treatment

Hamster anti-mouse CD3ε (clone 145-2C11; Pharmingen, San Diego, Calif.) mAb at 1 μg/well (=1 μg/ml of anti-CD3 antibody) was allowed to adhere to flat-bottomed, high-binding 96-well plates (Costar, Cambridge, Mass.) at 4° C. in 100 μl PBS. After 20 hours, plates coated with mAb were washed and transfected clones were plated at 1×105 cells/ well and incubated at 37° C. for 20 hours. Isotype-matched rat anti-mouse IgG 2b mAbs (clone R 35-38, Pharmingen) were used a control.

To evaluate Fas-mediated killing, 3DO cells (1×106) were incubated at room temperature for 30 minutes with 10 μg/ml of the antibody to Fas (hamster anti-mouse, done Jo2; Pharmingen), then washed and plated on wells coated with an antibody to hamster immunoglobulin G (5 μg/well; Pharmingen).

In selected experiments, a portion of T cells were treated with Cyclosporin (Calbiochem, San Diego, Calif.), in presence or absence of cross-linked monoclonal antibodies.

m) UV Irradiation, DEX Treatment and Starvation

In some experiments clones transfected with empty pcDNA3 or GELR-cDNA were exposed to different doses of UV rays from a UV Stratalinker (model 1800; Stratagene, La Jolla, Calif.).

Aliquots of 2 ml transfected clones (1×106/ml) were incubated with DEX or subjected to deprivation conditions (1% FCS). The apoptosis was evaluated after 20 hours as described below.

n) Flow Cytometry Analysis

A single suspension (1×106 cells/sample) was incubated for 30 minutes on ice in 50 μl staining buffer (PBS plus 5% FCS), containing 10 μg/ml hamster anti-mouse Fas mAb directly conjugated to R-phycoerythrin (PE) or PE-hamster IgG (isotype control).

Both mAbs were purchased from Pharmingen. Cells were also stained with rabbit polyclonal antibody raised against a peptide corresponding to amino acids 260–279 mapping at the carboxy terminus of human Fas-L (Santa Cruz Biotechnology, Inc., Santa Cruz, Calif.) or with isotype-matched antibody (ab), and with anti-rabbit IgG FITC conjugate, $F(ab')_2$ fragment (Sigma), as a second step reagent.

All clones were stained with hamster anti-mouse αCD3, directly conjugated with fluorescein (Pharmingen). The median or percentage of Fas and Fas-L histograms was calculated using lysis II research software (Becton-Dickinson, Mountain. View, U.S.A).

o) Apoptosis Evaluation by Propidium Iodide Solution

Apoptosis was measured by flow cytometry as described elsewhere (Nicoletti et al., 1991). After culturing, cells were centrifuged and the pellets gently resuspended in 1.5 ml hypotonic propidium iodide solution (PI, 50 μg/ml in 0.1% sodium citrate plus 0.1% Triton X-100). The tubes were kept overnight at 4° C. in the dark. The PI-fluorescence of individual nuclei was measured by flow cytometry using standard FACScan equipment (Becton Dickinson). The nuclei traversed a 488 nm Argon laser light beam. A 560 nm dichroid mirror (DM 570) and a 600 nm band pass filter (band width 35 nm) were used to collect the red fluorescence due to PI DNA staining. The data were recorded in logarithmic scale in a Hewlett Packard (HP 9000, model 310; Palo Alto, Calif.) computer. The percentage of apoptotic cell nuclei (sub-diploid DNA peak in the DNA fluorescence histogram) was calculated with specific FACScan research software (Lysis II).

p) Interleukin-2 (IL-2) Analysis

Supernatants from clones untreated or anti-CD3-treated for 18 hours, were tested for their concentration of IL-2 by two site ELISA using the monoclonal antibody JES6-1A12 as primary reagent and biotinlylated monoclonal antibody S4B6 as the secondary reagent. Both antibodies were purchased from Pharmingen. The IL2 titer (Means+/−Standard Deviation of replicate samples) was expressed as picogram per milliliter, calculated by reference to standard curves constructed with known amounts of IL-2. The sensitivity limit was approximately 20 pg/ml.

q) Nuclear and Cytoplasmatic Extracts

Nuclear proteins were extracted from $2\times10^7$ cells. Cells were washed with ice-cold PBS, and packed cells were resuspended in 1 ml of hypotonic buffer (25 mM HEPES, 50 mM KCl, 0.5% NP40, 0.1 mM Dithiothreitol, 10 μg/ml Leupeptin, 20 μg/ml Aprotinin, and 1 mM PMSF solution in ethanol. After 10 minutes of incubation on ice, the supernatants containing cytoplasmatic proteins were separated from the nuclear pellets by centrifugation. Nuclear pellets were then washed with ipotonic buffer without NP-40 and resuspended in 10 μl of lysis buffer (25 mM HEPES, 2 mM KCl, 0.1 mM Dithiothreitol, 10 μg/ml Leupeptin, 20 μg/ml Aprotinin, and 1 mM PMSF). After 15-min incubation on ice, lysates were diluted with 10 vol of dilution buffer (25 mM HEPES, 0.1 mM Dithiothreitol, 10 μg/ml Leupeptin, 20 μg/ml Aprotinin, and 1 mM PMSF and 20% glycerol) and cleared in a precooled microfuge for 30 min at 14,000×g, before loading.

r) Isolation of Human GILR

The human homologue of murine GILR was isolated from a λgt 11 human lymphocyte cDNA library (Clontech, Palo Alto, Calif., USA). Murine GILR cDNA $^{33}P$ labeled was used as a probe. Nitrocellulose filters (Amersham) obtained by blotting plates containing 5×10 clones were hybridized in 5×SSC, 5× Denhart's solution, 1% SDS, 100 μg/μl tRNA (SIGMA) and 20 mM sodium pyrophosphate (ph 6.8) at 42° C. for 12 hours, and the final wash was in 0.2×SSC, 0.1 SDS at 65° C. for 30 minutes. Fifty possible candidates were identified from replica filters and further screened as described (D'Adamio et al., 1997). Several clones derived from the third screening were isolated, digested with EcoRI and the cDNA insertions of about 2000 base pairs were subcloned into pcDNA3. After extraction and purification with alkaline lysis method (Maniatis et al., 1989), plasmid DNA from several clones were sequenced using T7 DNA polymerase in conjunction with Sp6 and T7 primers complementary to the plasmid cloning site sequences and with custom synthesized oligonucleotides primers (20 and 23 bases long).

Overlapping sequences were obtained for both strands of the cDNA.

II. Results a) Isolation of the Mouse GILR cDNA

In order to study the role of glucocorticoid hormones in the regulation of lymphocyte apoptosis, the isolation of mRNA induced by 3 hours treatment with the synthetic glucocorticoid hormone dexamethasone (DEX, 100 nM), in freshly isolated thymocytes, was performed. Comparing the cDNAs from untreated and DEX-treated cells, by the subtraction probe technique as noted above, some overexpressed mRNAs in the treated cells were identified. Upon sequencing the various detectable cDNAs, one of them, (designated 'GILR', for: Glucocorticoid Induced Leucine-zipper family Related gene), was shown to have some homology (40% similarity) with the, apparently unrelated, mouse TSC-22 sequence (Shibanuma et al., 1992) and hDIP (Vogel et al., 1996) this homology not being of major significance as the GILR sequence, more importantly, showed no homology with other sequences present in EMBL and Genbank database.

b) GILR Expression in Tissues: Induction in T Lymphocytes

Experiments were performed to examine and define GILR expression in different tissues. The results indicated that GILR mRNA was clearly detectable by Northern blotting (8 days exposure) in freshly isolated thymocytes, spleen and lymph node cells, slightly detectable in bone marrow, kidney and lung, and not detectable in liver, heart and brain, suggesting that the gene is mainly expressed in lymphoid tissues (FIG. 1A).

Figure 1B:
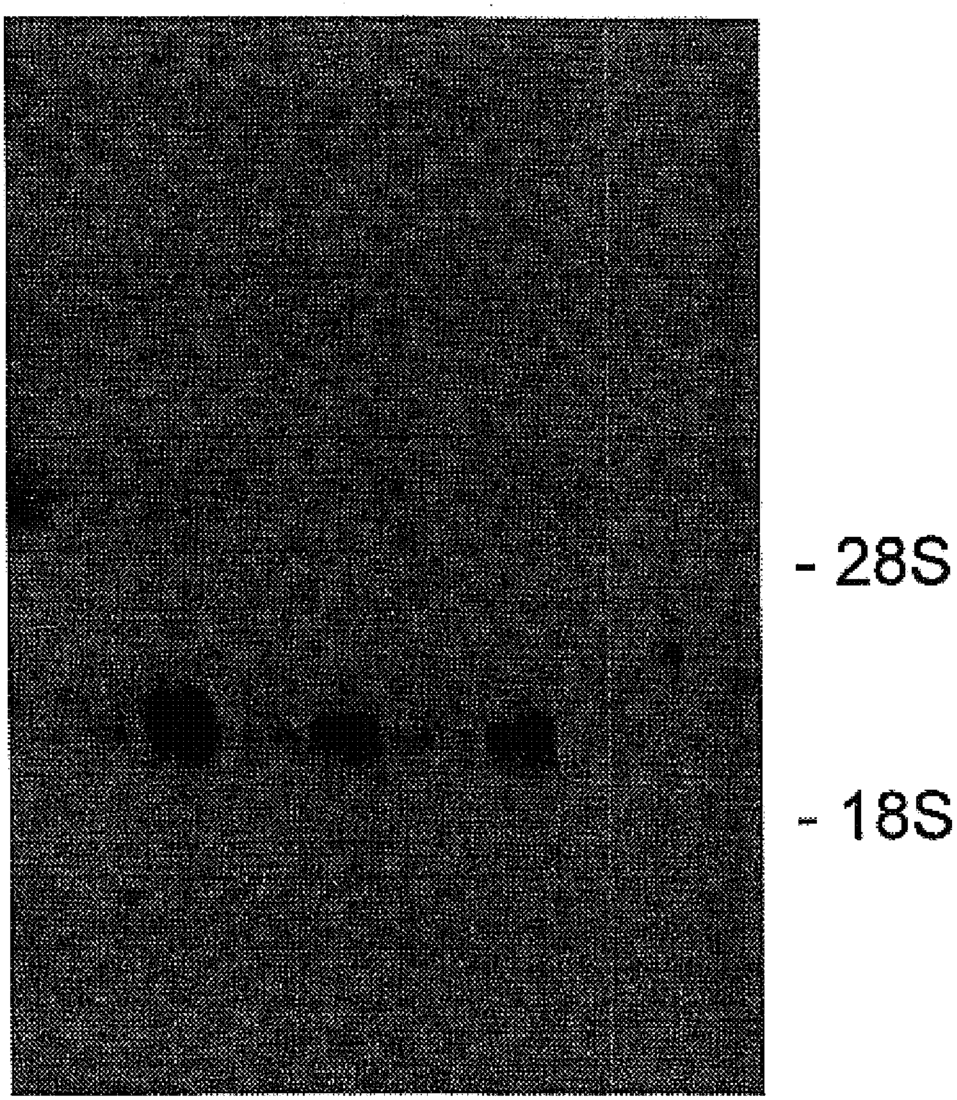
FIG. 1B shows the effect of Dexamethasone on GILR induction. Cells were either untreated (lanes 1, 3, 5) or treated (lanes 2, 4, 6) with 100 nM/l DEX for 3 hrs. Total RNA (25 μg) was extracted, electrophoresed on a gel and transferred to a nitrocellulose filter. The filter was hybridized with labeled GILR cDNA and exposed for 24 hours.

Experiments were performed to test the possible effect of DEX-treatment in lymphoid tissue. The results indicate that GILR expression was clearly increased by treatment with DEX in fresh thymocytes and lymphocytes from peripheral lymphoid tissues, including spleen and lymph node (FIG. 1B). This results differentiate clearly GILR from the more similar elements of the Leucine-zipper family hDIP (Vogel et al., 1996) and TSC-22 (Shibanuma et al., 1992), both ubiquitously expressed.

c) The Protein Coded by GILR is a Protein Belonging to the Leucine-Zipper Family In order to isolate a full-length GILR cDNA a thymus lymphocyte cDNA library was screened using an isolated probe (1100 bp) obtained by the subtraction probe procedure (see above). Several clones were isolated and 3 of them were 1972 bp long and displayed the same sequence. Since Northern blotting analysis (FIG. 1A) indicated that GILR mRNA was about 1.97 kB long, these clones were believed to represent fill-length cDNAs. This was confirmed by experiments using the primer-extension technique (results not shown).

Nucleotide sequencing of the above noted 3 cDNA clones coding for GILR showed the presence of a single open reading frame (ORF), beginning at nucleotide position number 206 and extending to a TAA termination codon at position 617 (FIG. 2).

The putative ATG initiation codon, at position 206, is surrounded by a sequence (GAACCATGA) in good agreement with the consensus sequence for initiation of translation in eukaryotes (Kozak, 1989). The termination codon is followed by a 3' untranslated region of 1355 bp. A polyadenylation signal is present 45 bp 5' to the poly-A tail.

The GILR amino acidic sequence displays significant homologies with molecules which belong to the leucine-zipper family (FIGS. 4 and 15; Shibanuma et al., 1992; Yamamoto et al., 1988; Nicholas et al., 1991; Hope and Struhl, 1987; Lamph et al., 1988).

The protein putatively encoded by the GILR mRNA is a leucine-zipper protein of 138 aa residues (FIG. 2). Four leucine residues are present at triplet positions 431–433, 452–454, 473–475 and 494–496, one asparagine at position 464–466, which is compatible with a leucine-zipper structure (underlined in FIG. 2) and presumably able to form dimers.

Furthermore a region (basic aa are underlined in FIG. 2), possibly representing a DNA-binding domain, is present at the N-terminal end, while a PAR region, rich in proline and acidic residues, is present at the C-terminal end region.

Figure 3A:
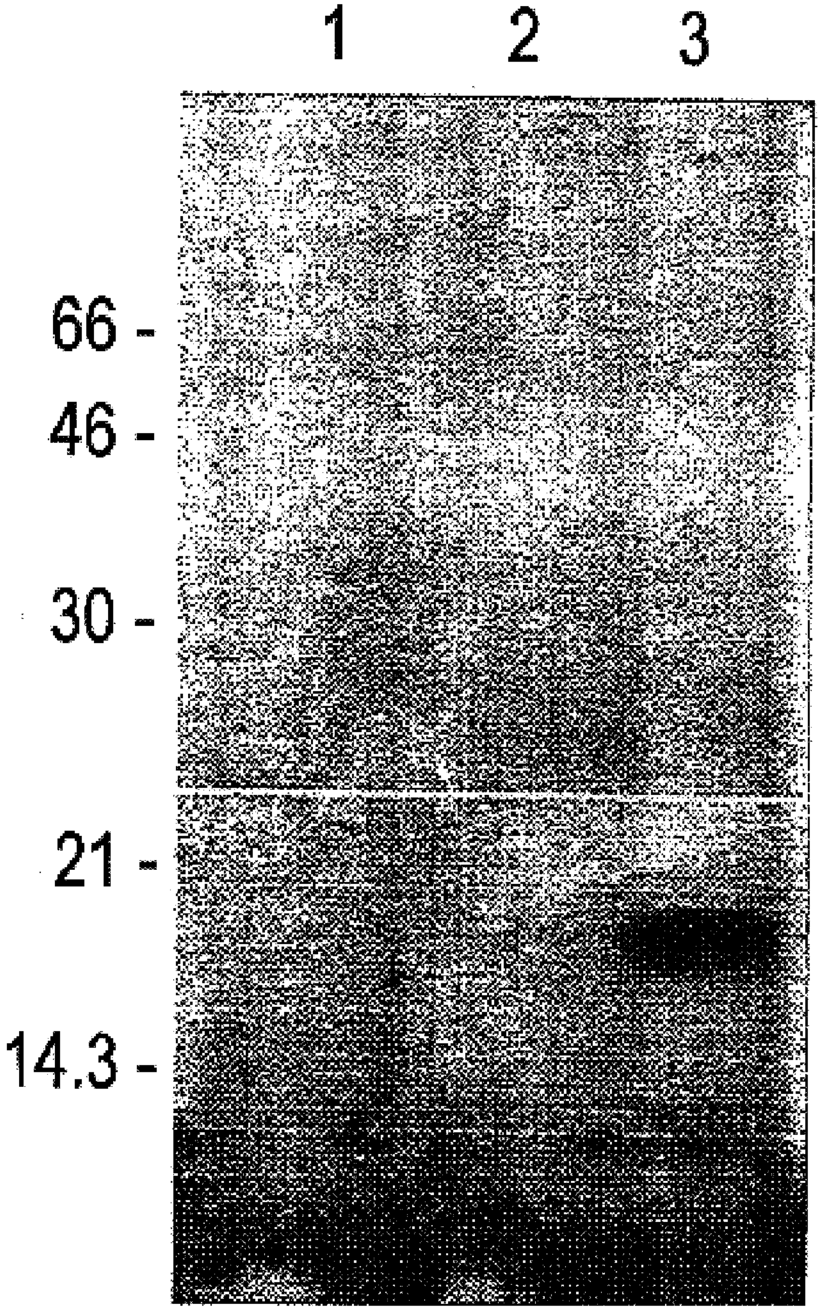
FIG. 3A shows the expression of GILR cDNA inserted into a Bluescript vector (lane 1, rabbit reticulocyte lysate control; lane 2, empty vector control; lane 3, vector carrying GILR cDNA (sense)) in which the expressed transcripts were translated in a rabbit reticulocyte lysate in the presence of [$^{35}$S]Met.
Figure 3B:
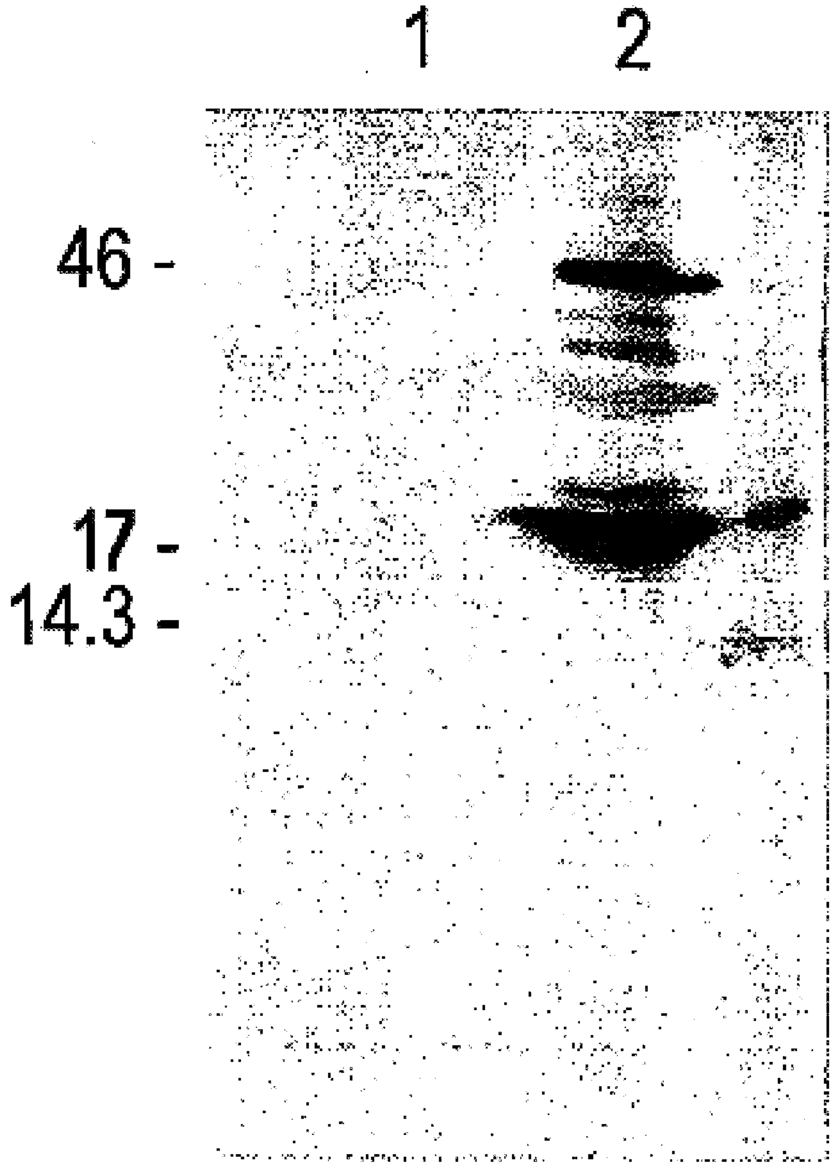
FIG. 3B shows a Western blot in which rabbit polyclonal antiserum was used for Western blot analysis of GILR fusion protein constructed and expressed as detailed herein below (lane 1, preimmune serum; lane 2, anti-GILR Ab)
Figure 3C:
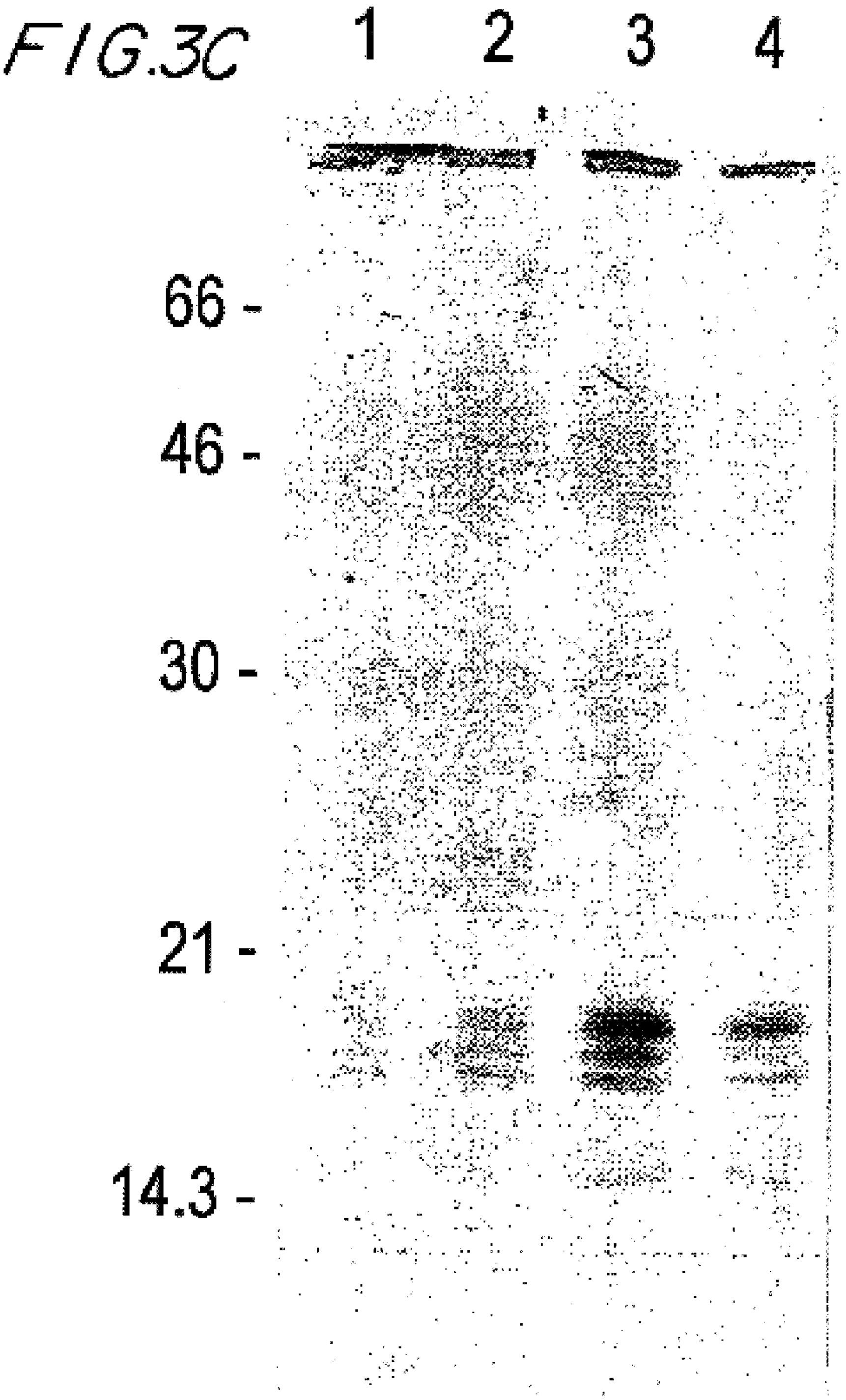
FIG. 3C shows the Western blot analysis of GILR protein performed using rabbit preimmune serum (lane 1, untreated thymocytes; lane 2, thymocytes treated with DEX 100 nM) or anti-GILR Ab (lane 3, untreated thymocytes; lane 4, thymocytes treated with DEX).

Based on these features, GILR can be classified as a leucine-zipper protein. The predicted molecular weight of the putative mature protein, before further post-translation modifications, is about 17,000 Da. The molecular weight of the native protein is about 17,000 Da (17 kDa) as indicated by in vitro translation experiments of the cloned cDNA (FIG. 3A) and by Western blot analysis experiments using a rabbit antiserum prepared against in vitro translated GILR protein (FIG. 3C). The antiserum was used to detect a cellular product of the GILR in normal untreated or DEX-treated (6 hours treatment) thymocytes. In particular, a band of molecular mass of approximately 17 kDa was detected by this antiserum in the protein extract of DEX-treated but not of untreated thymocytes, in a western blot analysis (FIG. 3C). FIG. 3B shows that this antiserum recognizes the in vitro translated fusion protein. In particular, the antiserum reveals either the GST fusion protein or the intact GILR protein obtained by thrombin digestion according to the Pharmacia protocol.

Figure 11A:
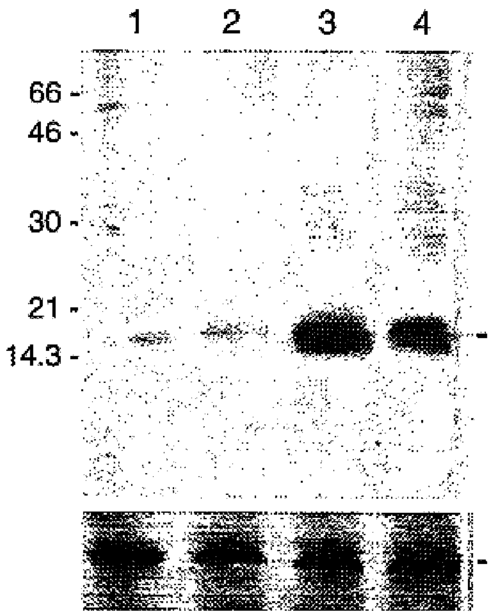
FIG. 11A is a protein immunoblot analysis of GILR protein. 3DO clones were trasfected with the empty vector pcDNA3: nuclear (lane 1) and cytoplasmatic (lane 3) protein extracts were purified, loaded on the gel and transferred to the filter. The nuclear and cytoplasmatic protein extracts from 3DO clones trasfected with GILR cDNA are shown in lane 2 and lane 4, respectively.
Figure 11B:
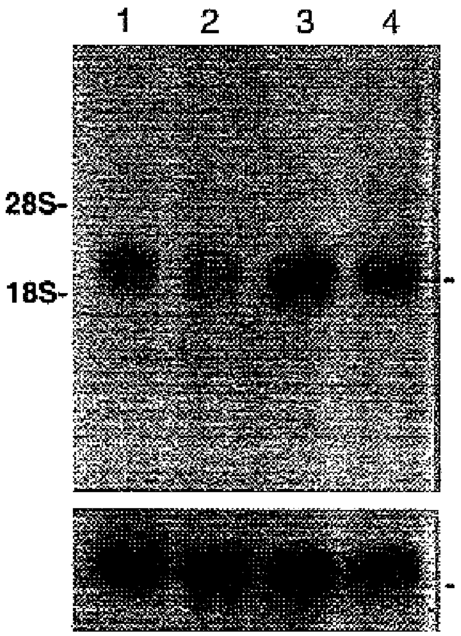
FIG. 11B shows an autoradiogram of a Northern blot analysis of GILR mRNA, comparing untreated thymocytes (lane 1), thymocytes cultivated on plates coated with anti-CD3 (1 μg/ml) for 3 hours (lane 2), thymocytes treated with 100 nM Dexamethasone for 3 hours (lane 3) and thymocytes cultivated on plates coated with anti-CD3 (1 μg/ml) for 3 hours and treated, for the same time, with 100 nM Dexamethasone. The filter was hybridized with labeled GILR cDNA and exposed for autoradiography for 48 hours. The amount of total RNA (25 μg) loaded in each lane, run on the gel and transferred to the filter is compared with the signal obtained with labeled β-actin cDNA.

Other experiments were performed to evaluate whether GILR protein and mRNA could be induced by treatment with DEX and whether this effect could be modulated by co-stimulation with anti-CD3 mAb (FIG. 11). Results of a representative Western blot experiment show that GILR protein is induced in thymocytes by treatment with DEX (lane 3) or anti-CD3 plus DEX (lane 4), whereas is down-modulated by treatment with anti-CD3 mAb alone (lane 2) (FIG. 11A). Similar results were obtained when GILR mRNA expression was evaluated. Northern blot experiment showed, in fact, that GILR mRNA is down-regulated by treatment with anti-CD3 mAb (FIG. 11B) (lane 2), it is induced by treatment with DEX (lane 3) or anti-CD3 plus DEX (lane 4). Similar results were obtained with spleen and lymph node cells (not shown).

Figure 12A:
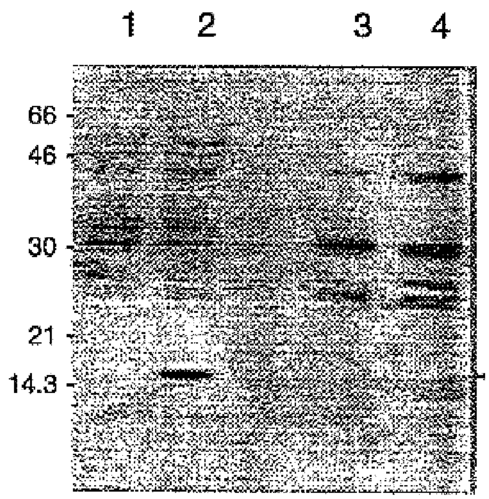
FIG. 12 (A, B) shows the results on the expression and the localization of GILR protein.
Figure 12B:
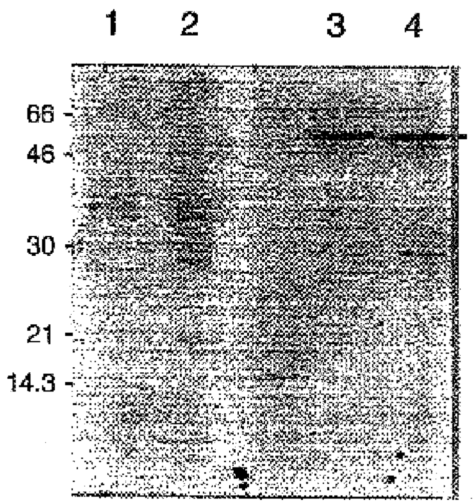

To define the subcellular localisation of GILR, the levels of GILR were evaluated in the nucleus and in the cytoplasm of clones transfected with the empty vector or with the GILR cDNA. FIG. 12A shows that GILR is detectable in the nucleic proteins extracted from a clone transfected with GILR cDNA but not in the cytoplasm or in the nucleus and cytoplasm of control clone. Anti-β tubulin antibody was used to control the possible nuclei contamination with cytoplasm material. Results in FIG. 12B indicate that β-tubulin is present in the cytoplasm protein extract of control (lane 3) and GILR transfected clones (lane 4) but not the nuclear extracts (lanes 1 and 2).

d) GILR Expression, in Transfected T Cells, Confers Resistance to TCR/CD3 Induced Apoptosis but not to Cell Death Induced by Other Stimuli Members of the leucine zipper family are involved in lymphocyte activation and are able to induce or inhibit apoptosis (Smeyne et al., 1993; Goldstone and Lavin, 1994). In order to test the possible effects of GILR expression on apoptosis, a hybridoma T-cell line, 3DO, was transfected, this 3DO cell line, like other T cell hybridomas, has been widely used in the investigation of apoptosis induced by anti-CD3 antibodies (Ayroldi et al., 1995; Vito et al., 1996). This transfection was carried out with an expression vector in which the GILR cDNA is expressed under the control of the CMV promoter. The apoptosis induced by anti-CD3 antibody in 3DO cells has been previously shown to be dependent on the Fas/Fas-L system (Yang et al., 1995). As controls, the empty vector (pcDNA3 control) was also used in such transfections. After selection with G418 antibiotic, cell clones were screened for the GILR expression by RNase protection analysis (FIG. 5). For each transfection, 9 clones were tested and used for functional characterization. In addition, 6 normal untransfected clones (nuc/1–6) were tested as further controls.

Figure 6:
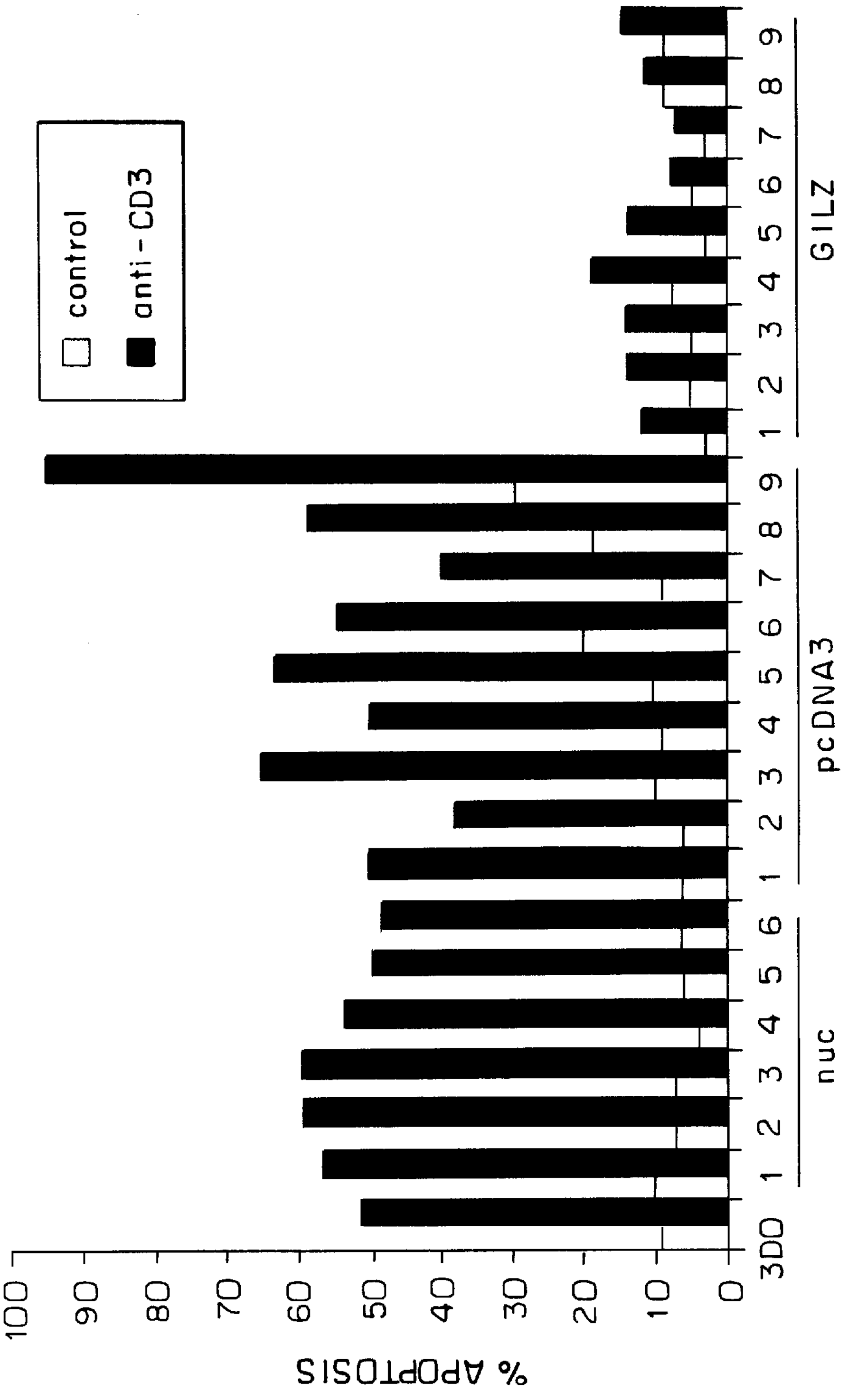
FIG. 6 shows a bar-graph representation of the results demonstrating the protection from TCR-induced death of 3DO transfected clones. 3DO cells were transfected by electroporation with 15 μg of linearized pcDNA3 or 15 μg linearized of pcDNA3 vector expressing the GILR cDNA. For induction of apoptosis, cells were cultured for 20 hrs on plates coated with anti-CD3 (1 μg/ml). The percentage of cell death was assessed by measurement of the DNA content of isolated nuclei stained with propidium iodide. The data shown are representative of three independent experiments.
Figure 7A:
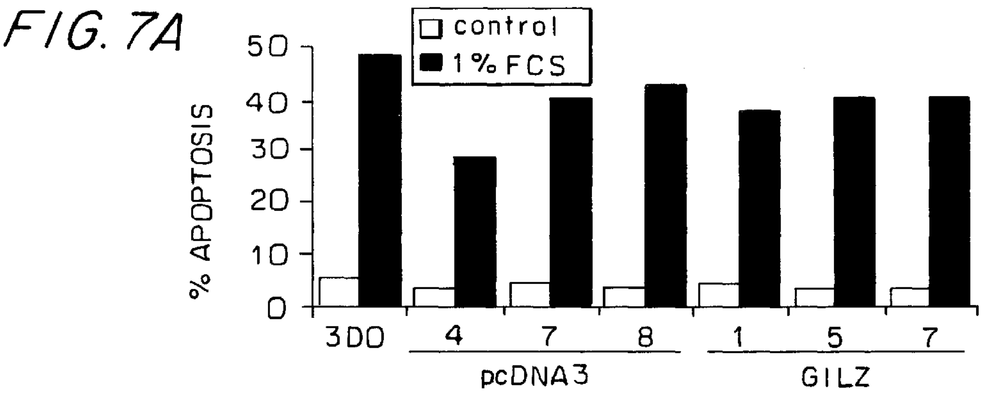
FIG. 7 (A-D) are bar-graph representations of the results of the analysis of apoptosis induced by other stimuli on 3DO transfected clones, wherein in FIG. 7A is shown the results obtained with withdrawn trophic factor.
in FIG. 7B is shown the results obtained with u.v. irradiation (100 J/m2)
in FIG. 7C is shown the results obtained with DEX (100 mM/l); and in FIG. 7D is shown the results obtained with monoclonal (mAb) anti-Fas antibody (5 μg/ml). All groups were treated for 20 hours. Cell death was measured as indicated above with respect to FIG. 6, and as noted herein below.
Figure 7B:
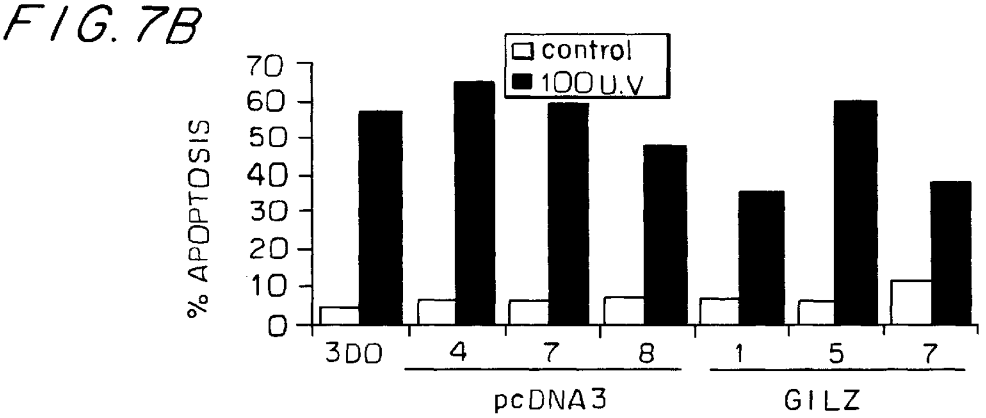
Figure 7C:
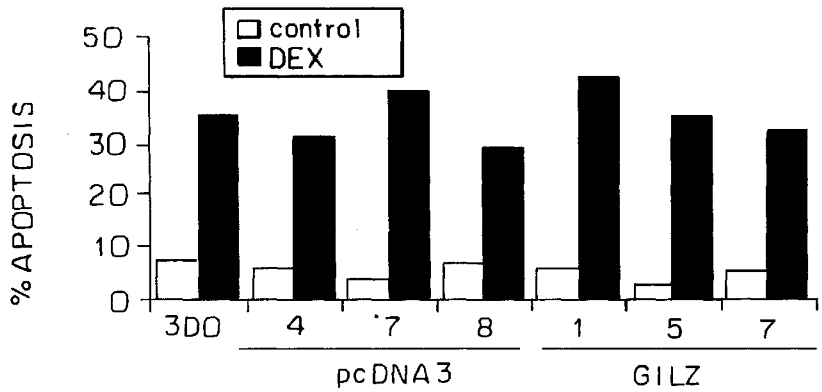
Figure 7D:
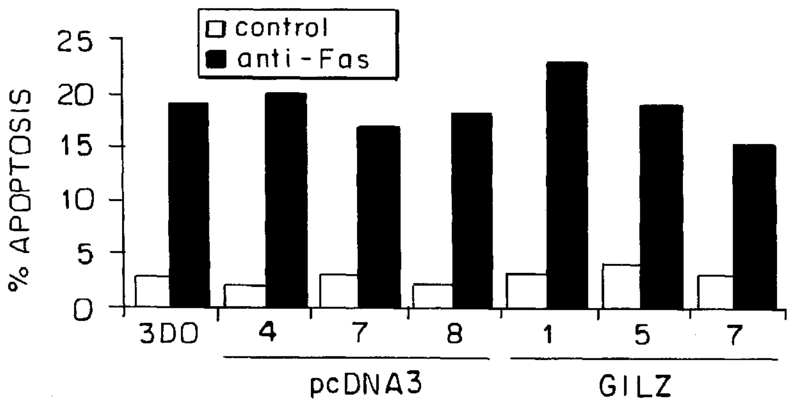

The results showed that cell clones overexpressing GILR (clones GILR/1–9) were all variably resistant to anti-CD3 mAb-induced apoptosis (apoptosis between 5% and 10%) with $P<0.0001$ as compared to pcDNA3 control clones (clones pcDNA3/1–9, apoptosis between 45% and 60%). No significant differences between pcDNA3 clones and normal untransfected clones (clones nuc/1–6, apoptosis between 45 and 60%) were detectable (FIG. 6). To exclude a possible effect of GILR gene on TCR/CD3 membrane expression, which could by itself account for diminished sensitivity to anti-CD3-induced apoptosis, all clones were stained with anti-CD3 mAb and analyzed by flow cytometry.

No differences of CD3 expression were detected between transfected and untransfected clones (results not shown).

It has been shown that T-cell apoptosis can be induced by various stimuli other than the triggering of the TCR/CD3 complex, including corticosteroids, UV irradiation and starvation (Zacharchuk et al., 1990; Bansal et al., 1991; Lowe et al., 1993).

Experiments were performed to test whether GILR expression could inhibit T cell apoptosis induced by other stimuli. Results obtained with the same clones (results with GILR/1,5,7 and pcDNA3/4,7,8 are shown in FIG. 7) indicate that GILR overexpression does not counteract apoptosis induced by DEX, various doses of Lw irradiation, starvation or triggering by crosslinked anti-Fas monoclonal antibody.

These results suggest that GILR can modulate T cell apoptosis triggered by TCR/CD3 complex but not by other stimuli.

Interestingly, the specific inhibitory effect of GILR on the CD3/TCR-dependent apoptotic signaling pathway is peculiarly different on the effect exerted by TSC-22, the more homologous Leucine-zipper protein. Scientific literature demonstrate that TSC-22 can induce apoptosis in a human carcinoma cell line (Ohta et al., 1997), it is induced by an anti cancer drug, Vesarinone, (Kawamata et al., 1998) in a human salivary gland cancer cell line and its down-regulation markedly enhances the growth of the cell line. (Nakashiro et al., 1998).

e) Expression of Fas and Fas-L in GILR Transfected T Cells

It has been suggested that T-cell AICD is also dependent on Fas/Fas-L interaction (Alderson et al., 1995; Dhein et al., 1995; Ju et al., 1995). In particular, the present inventors have previously shown that anti-CD3-induced apoptosis in 3DO cells is blocked by soluble anti-Fas mAb while crosslinked anti-Fas mAb directly induces cell death (Ayroldi et al., 1997). Experiments were performed to test whether blocking of Fas (using soluble, non-crosslinked anti-Fas mAb, 1 $\mu$g/ml) could inhibit the anti-CD3-induced apoptosis in this experimental system where clones of 3DO were tested. Results indicate that blocking of Fas significantly inhibits CD3-induced cell death (apoptosis, mean of results obtained with 3 normal clones in a 20 hours assay, was: 4±1 in untreated controls, 63±5 in anti-CD3-treated, 29±6 in anti-CD3-plus soluble anti-Fas-treated clones; $P<0.01$ comparing anti-CD3-treated with antiCD3-plus anti-Fas-treated).

Experiments were also performed to assess whether the inhibition of apoptosis in GILR-transfected cells could be mediated by an effect on Fas/Fas-L system expression.

Results show that 20 hours of anti-CD3 mAbs treatment induced Fas and Fas-L expression in 3DO cell line and in clones transfected the empty vector control (pcDNA3/4,7), but did not augment Fas and Fas-L expression in clones overexpressing GILR (clones GILR/1,2,3,5,7) (FIG. 8).

Kinetic experiments also indicate that while Fas-L expression is not evident at 3 hours after anti-CD3 treatment, when there is no detectable apoptosis, induction of Fas-L expression is detected at 10 hours when apoptosis is measurable. Results of a representative experiment with an empty vector and a GILR transfected clone are shown in Table I. Similar results were also obtained when Fas mRNA expression were evaluated by Northern blot and RNase protection assays (FIG. 9).

These results indicate that GILR expression inhibits TCR/CD3-activated apoptosis and Fas/Fas-L expression.

f) GILR in T-Cell Activation.

Having demonstrated that GILR overexpression rescued from anti-CD3-induced apoptosis by decreasing Fas/Fas-L expression, the role of GILR was then evaluated in T-cell activation. For that purpose, GILR transfected clones were activated and analyzed for apoptosis and expression of activation markers, like the interleukin-2 receptor (IL-2R). In particular, after stimulation with cross-linked anti-CD3 monoclonal antibodies (1 $\mu$g/ml), GILR-transfected and empty vector clones (used as control) were stained with anti-IL-2R monoclonal antibody (CD25) or treated for propidium iodide labeling for apoptosis evaluation. The supernatants from control and anti-CD3-treated clones were used for IL-2 detection in an ELISA assay.

Results showed that empty vector transfected clones express, upon anti-CD3 stimulation, high levels of IL-2R and produce IL-2, as evaluated by flow-cytometry analysis, and ELISA assay respectively. In contrast, GILR-transfected clones express low or undetectable levels of IL-2 (Table II). These data indicate tha overexpression of GILR inhibits anti-CD3 induced activation and suggest that GILR may play a role in controlling T-cell activation.

To further investigate the role of GILR in T-cell activation, we next examined its expression upon anti-CD3 and/or anti-CD2 stimulation and the effects of cyclosporin-A.

It has been demonstrated that CD2 triggering rescues T-cells from anti-CD3-induced apoptosis by down-modulation of the Fas/Fas-L system (Ayroldi et al., 1997).

Figure 10A:
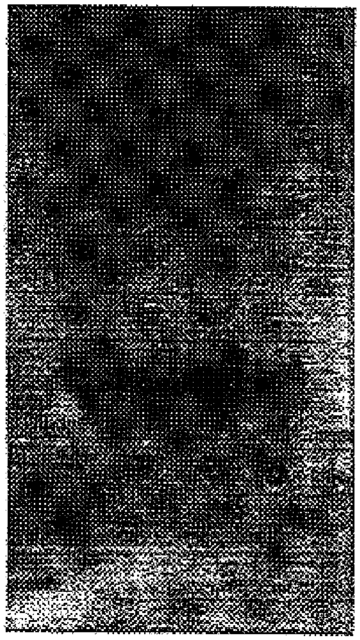
FIG. 10A shows that anti-CD3 down-modulates and anti-CD2 up-modulates GILR expression. 3DO cells were cultured in 96-well plates with medium alone, coated with anti-CD3 (1 μg/ml) and or anti-CD2 monoclonal antibody (1 μg/ml) and or anti-CD2 monoclonal antibody (50 μg/ml). Lane 1=control; lane 2=anti CD3+anti CD2; lane 3=anti-CD2; lane 4=anti CD3.

This effect is mediated by the decrease of IL-2 endogenous production and therefore of T-cell activation. The expression of GILR was then studied, using Northern blot, in 3DO cells treated with anti-CD3 and/or anti-CD2 monoclonal antibodies. FIG. 10A shows that GILR mRNA is down-regulated by anti-CD3 activation, whereas it is up-modulated by anti CD2 treatment. Co-stimulation with both anti-CD2 and anti-CD3 treatment restores GILR mRNA to the control level.

Figure 10B:
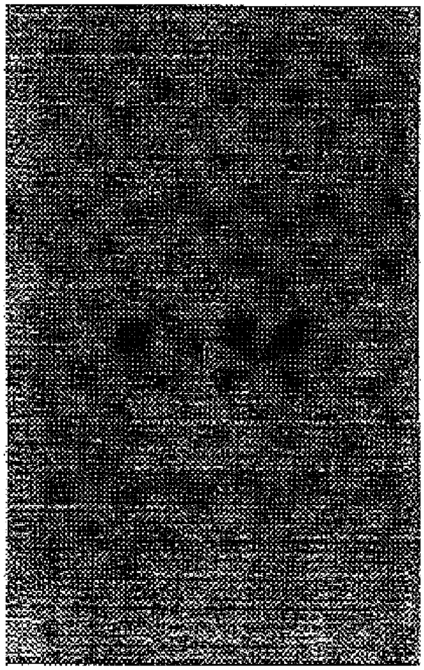
FIG. 10B shows that cyclosporin inhibits anti-CD3-driven down-modulation of GILZ expression. 3DO cells were cultured on anti-CD3-coated plates (1 μg/ml) in presence or in absence of cyclosporin (1 μg/ml). In both 10A and 10B, the expression of GILR was evaluated by Northern blot. 20 μg RNA were loaded on each lane. Lane 1=control; lane 2=anti CD3; lane 3=Cyclosporin; lane 4=anti CD3+cyclosporin.

It has been previously reported that cyclosporin specifically inhibits the TCR-mediated transcription of IL-2 gene. through the block of the calcium dependent signal transduction pathway (Liu et al., 1993). As FIG. 10B shows, cyclosporin-A reverts anti-CD3-induced GILR down-modulation.

These results further suggest the involvement of GILR in the control of T-cell activation.

g) Isolation of the Human GILR cDNA

The human homologue of murine GILR was isolated in a screening of a λgt11 human cDNA library created from T lymphocyte PHA stimulated, using the previously isolated mouse GILR cDNA as a probe. Among the positive clones, four displayed the same sequence, highly homologous to mouse GILR cDNA sequence, and the same length (1946 base pairs, FIG. 2).

The cDNA sequence of the human GILR (h-GILR) is shown in FIG. 13. The cDNA contains a single base pair open frame, beginning at nucleotide position 241 and extending to a termination codon at position 643. Human GILR has a 86% of identity at DNA level (FIG. 14), and a 94% identity and 97% similarity with mouse GILR(FIG. 15) at protein level. Human GILR is a Leucine-zipper protein which is highly homologous to murine GILR and shows similarity to the previously described TSC-22 and hDIP proteins especially at C-terminal, where the Leucine-zipper motif is located.

TABLE I

Time course of Fas/L expression related to anti-CD3-induced apoptosis on an empty vector or GILR transfected clone

| | 3 h | | 6 h | | 10 h | |
|---|---|---|---|---|---|---|
| | Fas/L | Apoptosis | Fas/L | Apoptosis | Fas/L | Apoptosis |
| pcDNA3(4) | 0.7* | 1.3 | 1.0 | 2.5 | 5.7 | 2.9 |
| pcDNA4(4) + anti-CD3 | 1.2 | 1.7 | 1.1 | 3.7 | 81.1 | 72.0 |
| GILR(7) | 1.0 | 0.3 | 1.7 | 1.8 | 0.1 | 2.8 |
| GILR(7) + anti-CD3 | 0.6 | 0.9 | 1.2 | 1.4 | 1.4 | 2.7 |

= Numbers represent the percent of cells positive for Fas/L at flow Cytometry analysis and of cells that were apoptotic to propidium iodide analysis.

TABLE II

Activation markers in GILR-transfected clones

| | APOPTOSIS (%) | | IL-2R (%) | | IL-2 (pg/ml) | |
|---|---|---|---|---|---|---|
| CLONES | control | anti-CD3 | control | anti-CD3 | control | anti-CD3 |
| empty vector | | | | | | |
| PV5 | 1.7 | 55.7 | 3.3 | 85.2 | neg. | |
| PV6 | 5.8 | 62.8 | 5.8 | 62.8 | 1200 | |
| PVT1 | 5.5 | 59.3 | 1.3 | 87.7 | neg. | |
| | | | | | 601 | |
| | | | | | neg. | |
| | | | | | 555 | |
| GILR vector- | | | | | | |
| ST7 | 6.4 | 39.3 | 6.9 | 32 | neg | 448 |
| SG11 | 2.4 | | 6.5 | 13 | neg. | |
| SG5 | 4.6 | | 7.1 | 33.6 | neg. | |
| ST5 | 6.5 | 41.6 | 4.4 | 28.1 | neg. | 339 |
| GILR19 | 2.4 | 32.8 | 2.6 | | neg. | 25 |
| | 2.6 | | 6.4 | | neg. | 6 |
| | 6.4 | | | | | |

REFERENCES

Alderson, M. R. et al. (1995). *J. Exp. Med.*, 181, 71–77.

Ausubel, F. M. et al. (1987–1995). Eds. Current Protocols in Molecular Biology.

Ayroldi, E. et al. (1995). *Blood,* 86: 2672–2678.

Ayroldi, E. et al., (1997). *Blood,* 89: 3717–3726.

Bansal, N., (1991). *FASEB J.,* 5: 211–216.

Barinaga, M. (1993). *Science,* 262:1512–1514.

Beg, A. A. and Baltimore, D. (1996). *Science,* 274:782–784.

Beidler, J. et al., (1995). *J. Biol. Chem.,* 270:16526–16528.

Beutler, B. and Ceranii, C. (1987). *NEJM,* 316:379–385.

Boldin, M. P. et al. (1995a). *J. Biol. Chem.,* 270:337–341.

Boldin, M. P. et al., (1995b). *J. Biol. Chem.,* 270:7795–7798.

Boldin, M. P. et al. (1996). *Cell,* 85:803–815.

Brakebusch, C. et al. (1992). *EMBO J.,* 11:943–950.

Bursch, W. et al. (1992). *Trends Pharmacol. Sci.,* 13, 245–251.

Cantor, G. H. et al. (1993). *Proc. Natl. Acad. Sci. USA,* 90:10932–10936.

Chen, C. J. et al. (1992). *Ann. N.Y. Acad. Sci.,* 660:271–273.

Chinnaiyan et al. (1995). *Cell,* 81:505–512.

Chirgwin, J. M. et al. (1979). *Biochemistry,* 18: 5294–5299.

Cohen, J. J. (1993). *Immunol. Today,* 14: 126–130.

Cohen, J. J. and Duke, R. C. (1984). *J. Immunol.,* 132, 38–42.

Crisell, P. et al. (1993). *Nucleic Acids Res.,* 21, 5251–5255.

D'Adamnio, F. et al. (1997). *Immunity,* 7, 803–808.

Dent, A. L. et al. (1990). *Nature,* 343: 714–719.

Dhein, J. et al. (1995). *Nature,* 373: 438–441.

Enari, M. et al. (1995). *Nature,* 375: 78–81.

Fernandes-Alnemri, T. et al. (1996). *Proc. Natl. Acad. Sci. USA,* 93: 7464–7469.

Galle, P. R. et al. (1995). *J. Exp. Med,* 182: 1223–1230.

Geysen, H. M. (1985). *Immunol. Today,* 6: 364–369.

Geysen, H. M. et al. (1987). *J. Immunol. Meth.,* 102: 259–274.

Goldstone, S. D. and Lavin, M. F. (1994). *Oncogene,* 9: 2305–2311.

Gubler, U. and Hoffman, B. J. (1983). *Genie,* 25: 263–269.

Henkart, P. A. (1996) *Immunity,* 4:195–201.

Hope, I. A. and Struhl, K. (1987). *EMBO J.,* 6: 2781–2784.

Howard, A. D. et al. (1991). *J. Immunol.,* 147:2964–2969.

Hsu, H. et al. (1995). *Cell,* 81: 495–504.

Hsu, H. et al. (1996). *Cell,* 84: 299–308.

Itoh, N. and Nagata, S. (1993). *J. Biol. Chem.,* 268: 10932–10937.

Itoh, N. et al. (1991). Cell, 66: 233–243.

Jay, P. et al. (1996), *Biochem. Biophys. Acta,* 222: 821–826

Jenkinson, E. J. et al. (1989). *Eur. J. Immuniol.,* 19: 2175–2177.

Joseph, S. and Burke, J. M. (1993) *J. Biol. Chem.,* 268: 24515–24518.

Ju-S. T. et al. (1995). *Nature,* 373: 444–448.

Kabelitz, D. et al. (1993). *Immunol. Today,* 14, 338–339.

Kaufmann, S. H. (1989). *Cancer Res.* 49: 5870–5878.

Kaufmann, S. H. (1993). *Cancer Res.* 53: 3976–3985.

Kawamata, H., et al. (1998). *Br. J. Cancer,* 77: 71–78

Kerr, J. F. R. et al. (1972). *Br. J. Cancer,* 26: 239–257.

Kischkel, F. C. et al. (1995). *EMBO J,* 14: 5579–5588.

Koizumi, M. et al. (1993). *Biol. Pharm. Bull* (Japan), 16: 879–883.

Kozak, M. (1989). *J. Cell. Biol,* 108: 229–241.

Kumar, S. (1995). *Trends Biochem Sci.,* 20: 198–202.

Lamph, W. W. et al. (1988). *Nature,* 334: 629–631.

Lazebnik, Y. A. et al. (1994). *Nature,* 371: 346–347.

Los, M. et al. (1995). *Nature,* 375: 81–83.

Lowe, S. W. et al. (1993). *Nature,* 362: 847–849.

Malinin, N. L. et al. (1997). *Nature,* 385: 540–544.

Maniatis, T. et al. (1989). Molecular cloning: A laboratory manual. Cold Spring Harbor, New York Cold Spring Harbor Laboratory.

MacDonald, H. R. and Lees, R. K. (1990). *Nature,* 343: 642–644.

Mashima, T. et al. (1995). *Biochem. Biophys. Res. Commun.* 209: 907–915.

Migliorati, G. et al. (1993). *Blood,* 81: 1352–1358.

Milligan, C. E. et al. (1995). *Neuron,* 15: 385–393.

Muranishi, S. et al. (1991). *Pharm. Research,* 8: 649.

Nagata, S. and Golstein, P. (1995). *Science,* 267: 1449–1456.

Nakashiro, K. et al. (1998). *Cancer Res.,* 58: 549–555.

Nicholas, S. F. et al. (1991). *Cell,* 64: 739–749.

Nicoletti, I. et al. (1991). *J. Immunol. Methods,* 139: 271–279.

Nieto, M. A et al. (1990). *J. Immunol.,* 145: 1364–1368.

Nieto, M. A. and Lopez-Rivas, A. (1989). *J. Immunol.,* 143: 4166–4170.

Ohta, S. et al. (1997). *Blochem. J.,* 324: 777–782.

Osborne, B. A and Schwartz, L. M. (1994). *Trends Cell. Biol.,* 4: 394–399.

Piquet, P. F. et al. (1987). *J. Exp. Med,* 166: 1280–1289.

Shibanuma, M. et al. (1992). *J. Biol. Chem.,* 267: 10219–10224.

Shi, Y. et al. (1992). *Science,* 257: 212–214.

Shimayamna, T. et al. (1993). *Nucleic Acids Symp. Ser.,* 29: 177–178
Shore, S. K. et al. (1993). *Oncogene,* 8: 3183–3188.
Sleath, P. R. et al. (1990). *J. Biol. Chem.,* 265: 14526–14528.
Smeyne, R. J. et al. (1993). *Nature,* 363: 166–169.
Smith, C. A et al. (1989). *Nature,* 337: 181–184.
Song, H. Y. et al. (1994). *J. Biol. Chem.,* 269: 22492–22495.
Srinivasula, S. M. et al. (1996). *Proc. Nail. Acad Scf. USA,* 93: 14486–14491.
Stanger, B. Z. et al. (1995). *Cell,* 81: 513–523.
Tan, Y. et al. (1994). *Mol. Cell. Biol.,* 14: 7546–7556.
Tartaglia, L. A. et al. (1993). *Cell,* 74: 845–853.
Tewani, M. et al. (1995). *J. Biol. Chem.,* 270: 3255–3260.
Thornberry, N. A. et al. (1992). Nature 356: 768–774.
Thornberry, N. A. et al. (1994). Biochemistry 33: 3934–3940.
Tracey, J. T. et al. (1987). *Nature,* 330: 662–664.
Van Antwerp, D. J. et al. (1996). *Science,* 274: 787–789.
Vandenabeele, P. et al. (1995). *Trends Cell Biol.,* 5: 392–400.
Vito, P. et al. (1996). *Science,* 271: 521–525.
Vogel. P. et al. (1996). *Biochem. Biophys. Acta.,* 1309: 200–204.
Wallach, D. (1986) In: *Interferon* 7 (Ion Gresser, ed.), pp. 83–122, Academnic Pres, London.
Waflach, D. et al. (1994) *Cytokine,* 6: 556.
Wang, C.-Y et al. (1996) *Science,* 274: 784–787.
Watanabe, F. R. et al. (1992). *J. Immunol.,* 148: 1274–1279.
Webb, S. et al. (1990). *Cell,* 63: 1249–1256.
Wilks, A. F. et al. (1989). *Proc. Natl. Acad. Sci. USA,* 86: 1603–1607.
Wyllie, A. H. (1980). *Nature,* 284: 555–556.
Wyllie, A. H. et al. (1980). *Int. Rev. Cytol.,* 68: 251–306.
Xue, D. et al. (1995) *Nature* 377:248–251.
Yamamoto, K. K. et al. (1988). *Nature,* 334: 494–498.
Yang, Y. et al. (1995). *J. Exp. Med,* 181: 1673–1682.
Yonehara, S. et al. (1989). *J. Exp. Med.,* 169: 1747–1756.
Zacharchuk, C. M. et al. (1990). J. Immunol., 145: 4037–4045.
Zaccharia, S. et al. (1991). *Eur. J. Pharmacol,* 203: 353–357.
Zhao, J. J. and Pick, L. (1993). *Nature,* 365: 448–451.

What is claimed is:

1. A glucocorticoid-induced leucine-zipper family related (GILR) protein capable of inhibiting apoptosis and stimulating lymphocyte activity, wherein said GILR protein:

(a) is encoded by the nucleotide sequence of SEQ ID NO: 1; or (b) contains no more than five amino acid changes from the amino acid sequence of SEQ ID NO:2, each of said changes being either alternative conservative substitutions within one of the following five groups of amino acid residues:

(1) Ala, Ser, Thr, Pro, Gly;

(2) Asp, Asn, Glu, Gln;

(3) His, Arg, Lys;

(4) Met, Leu, Ile, Val, Cys; and (5) Phe, Tyr, Trp or deletion of one or more of residues 123, 124, and 125 of SEQ ID NO:2.

2. A composition for the inhibition of apoptosis in cells or for stimulating lymphocyte activation, comprising, as an active ingredient, the GILR protein of claim 1.

3. A chemically modified GILR protein of claim 1, wherein said GILR protein of claim 1 is chemically modified by being conjugated or complexed with molecules facilitating or enhancing the transport of said GILR protein across cell membrane and wherein the chemically modified GILR protein has the same or higher biological activity as said GILR protein.

4. A composition for the inhibition of apoptosis in cells or for stimulating lymphocyte activation, comprising, as an active ingredient, the chemically modified GILR protein of claim 3.

5. The GILR protein of claim 1, which is encoded by the nucleotide sequence of SEQ ID NO:1.

6. The GILR protein of claim 1, wherein said no more than five amino acid changes from the amino acid sequence of SEQ ID NO:2 are present at amino acid residue positions selected from the group consisting of residue positions 22, 50, 75, 84, 112, 122, 123, 124, 125, 127, and 128 of SEQ ID NO:2.

7. The GILR protein of claim 1, which contains no more than three amino acid changes from the amino acid sequence of SEQ ID NO:2.

8. The GILR protein of claim 7, wherein said no more than three amino acid changes from the amino acid sequence of SEQ ID NO:2 are present at amino acid residue positions selected from the group consisting of residue positions 22, 50, 75, 84, 112, 122, 123, 124, 125, 127, and 128 of SEQ ID NO:2.

9. The GILR protein of claim 1, which contains a single amino acid change from the amino acid sequence of SEQ ID NO:2.

10. The GILR protein of claim 9, wherein said single amino acid change from the amino acid sequence of SEQ ID NO:2 is present at an amino acid position selected from the group consisting of residue positions 22, 50, 75, 84, 112, 122, 123, 124, 125, 127, and 128 of SEQ ID NO:2.

11. A glucocorticoid-induced leucine-zipper family related (GILR) protein capable of inhibiting apoptosis and stimulating lymphocyte activity, wherein said GILR protein contains no more than ten amino acid changes from the amino acid sequence of SEQ ID NO:2, each of said changes being either alternative conservative substitutions of amino acid residue positions selected from the group consisting of residue positions 22, 50, 75, 84, 112, 122, 127, and 128 of SEQ ID NO:2 within one of the following five groups of amino acid residues:

(1) Ala, Ser, Thr, Pro, Gly;

(2) Asp, Asn, Glu, Gln;

(3) His, Arg, Lys;

(4) Met, Leu, Ile, Val, Cys; and (5) Phe, Tyr, Trp, or deletion of one or more of residues 123, 124, and 125 of SEQ ID NO:2.

12. The GILR protein of claim 11, wherein said alternative conservative substitutions of amino acid residue positions are selected from the group consisting of residue positions 50, 75, 84, 122, and 128.

13. A composition for the inhibition of apoptosis in cells or for stimulating lymphocyte activation, comprising, as an active ingredient, the GILR protein of claim 11.

14. A chemically modified GILR protein of claim 11, wherein said GILR protein of claim 11 is chemically modified by being conjugated or completed with molecules facilitating or enhancing the transport of said GILR protein across cell membrane and wherein the chemically modified GILR protein has the same or higher biological activity as said GILR protein.

15. A composition for the inhibition of apoptosis in cells or for stimulating lymphocyte activation, comprising, as an active ingredient, the chemically modified GILR protein of claim 14.

* * * * *

```
                         SEQUENCE LISTING


(1) GENERAL INFORMATION:

   (iii) NUMBER OF SEQUENCES: 15


(2) INFORMATION FOR SEQ ID NO: 1:

     (i) SEQUENCE CHARACTERISTICS:
          (A) LENGTH: 1972 base pairs
          (B) TYPE: nucleic acid
          (C) STRANDEDNESS: single
          (D) TOPOLOGY: linear

    (ii) MOLECULE TYPE: cDNA

   (iii) HYPOTHETICAL: NO

    (iv) ANTI-SENSE: NO

    (ix) FEATURE:
          (A) NAME/KEY: CDS
          (B) LOCATION:206..616

    (xi) SEQUENCE DESCRIPTION: SEQ ID NO: 1:

CTGGCTGCTG TGGAGTTTGT GACATACTAG GTGACACCCT TGGAGTCACT TCTCTTCAAC      60

TCCAGCTTAG AAGTGCCTGC CTGGCTCAGG GTCTGCACTG CAGCCTACTC CTTGCTTCAG     120

GGCCTGACTG CAACGCCAAA GCCTATCCTA TAGCGGCAGC GCCAGCAGCC ACTCAAACCA     180

GCCACAGCTC CCCGGCAACC GAACC ATG AAC ACC GAA ATG TAT CAG ACC CCC       232
                            Met Asn Thr Glu Met Tyr Gln Thr Pro
                             1               5

ATG GAG GTG GCG GTC TAT CAG CTG CAC AAT TTC TCC ACC TCC TTC TTT       280
Met Glu Val Ala Val Tyr Gln Leu His Asn Phe Ser Thr Ser Phe Phe
 10                  15                  20                  25

TCT TCT CTG CTT GGA GGG GAT GTG GTT TCC GTT AAA CTG GAT AAC AGT       328
Ser Ser Leu Leu Gly Gly Asp Val Val Ser Val Lys Leu Asp Asn Ser
                 30                  35                  40

GCC TCC GGA GCC AGT GTG GTG GCC CTA GAC AAC AAG ATT GAG CAG GCC       376
Ala Ser Gly Ala Ser Val Val Ala Leu Asp Asn Lys Ile Glu Gln Ala
             45                  50                  55

ATG GAC CTC GTG AAG AAC CAC CTG ATG TAC GCT GTG AGA GAG GAG GTG       424
Met Asp Leu Val Lys Asn His Leu Met Tyr Ala Val Arg Glu Glu Val
         60                  65                  70
```

-continued

```
GAG GTC CTA AAG GAG CAG ATT CGT GAG CTG CTT GAG AAG AAC TCC CAG      472
Glu Val Leu Lys Glu Gln Ile Arg Glu Leu Leu Glu Lys Asn Ser Gln
     75                  80                  85

CTG GAG CGC GAG AAC ACC CTC CTG AAG ACG CTG GCA AGC CCC GAG CAA      520
Leu Glu Arg Glu Asn Thr Leu Leu Lys Thr Leu Ala Ser Pro Glu Gln
 90                  95                 100                 105

CTG GAA AAG TTC CAG TCC CGG CTG AGC CCT GAA GAG CCA GCA CCT GAA      568
Leu Glu Lys Phe Gln Ser Arg Leu Ser Pro Glu Glu Pro Ala Pro Glu
                110                 115                 120

GCC CCA GAA ACC CCG GAA ACC CCG GAA GCC CCT GGT GGT TCT GCG GTG      616
Ala Pro Glu Thr Pro Glu Thr Pro Glu Ala Pro Gly Gly Ser Ala Val
            125                 130                 135

TAAGTGGCTC TGTCCTTAGG GTGGGCAGAG CCACATCTTG TTCTACCTAG TTCTTTCCAG    676

TTTGTTTTTG GCTCCCCAAG GGTCATCTCA TGTGGAGAAC TTTACACCTA ACATAGCTGG    736

TGCCAAGAGA TGTCCCAAGG ACATGCCCAT CTGGGTCCAC TCCAGTGACA GACCCCTGAC    796

AAAGAGCAGG TCTCTGGAGA CTAAGTTGCA TGGGGCCTAG TAACACCAAG CCAGTGAGCC    856

TGTCGTGTCA CCGGGCCCTG GGGGCTCCCA GGGCTGGGCA ACTTAGTTAC AGCTGACCAA    916

GGAGAAAGTA GTTTTGAGAT GTGATGCCAG TGTGCTCCAG AAAGTGTAAG GGGTCTGTTT    976

TTCATTTCCA TGGACATCTT CCACAGCTTC ACCTGACAAT GACTGTTCCT ATGAAGAAGC   1036

CACTTGTGTT CTAAGCAGAA GCAACCTCTC TCTTCTTCCT CTGTCTTTTC CAGGCAGGGG   1096

CAGAGATGGG AGAGATTGAG CCAAATGAGC CTTCTGTTGG TTAATACTGT ATAATGCATG   1156

GCTTTGTGCA CAGCCCAGTG TGGGGTTACA GCTTTGGGAT GACTGCTTAT AAAGTTCTGT   1216

TTGGTTAGTA TTGGCATCGT TTTTCTATAT AGCCATAATG CGTATATATA CCCATAGGGC   1276

TAGATCTATA TCTTAGGGTA GTGATGTATA CATATACACA TACACCTACA TGTTGAAGGG   1336

CCTAACCAGC TTTGGGAGTA CTGACTGGTC TCTTATCTCT TAAAGCTAAG TTTTTGACTG   1396

TGCTAATTTA CCAAATTGAT CCAGTTTGTC CTTTAGATTA AATAAGACTC GATATGAGGG   1456

AGGGAGGGGA AGACCAGCCT CACAATGCGG CCACAGATGC CTTGCTGCTG CAGTCCTCCC   1516

TGATCTGTCC ACTGAAGACA TGAAGTCCTC TTTTGAATGC CAAACCCACC ATTCATTGGT   1576

GCTGACTACA TAGAATGGGG TTGAGAGAAG ATCAGTTTGG ACTTCACATT TTTGTTTTAA   1636

GTTTTAGGTT GTTTTTTTTT GGTTTTGTTT GTTTGTTTGT TTGTTTGTTT TTGTTTTTGT   1696

TTTTTCTTTT TTAAGTTCTT GTGGGGAAAC TTTGGGGTTA ATCAAAGGAT GTAGTCCTGT   1756

GGTAGACCAG AGGAGTAACT AGTTTTGATC CTTTGGGGTG TGGAAAATGT ACCCAGGAAG   1816

CTTGTGTAAG GAGGTTCTGT GACAGTGAAC ACTTTCCACT TTCTGACACC TCATCCTGCT   1876

GTACGACTCC AGGATTTGGA TTTGGATTTT TCAAATGTAG CTTGAAATTT CAATAAACTT   1936

TGCTCCTTTT TCTAAAAATA AAAAAAAAAA AAAAAA                             1972
```

(2) INFORMATION FOR SEQ ID NO: 2:

(i) SEQUENCE CHARACTERISTICS:
(A) LENGTH: 137 amino acids
(B) TYPE: amino acid
(D) TOPOLOGY: linear (ii) MOLECULE TYPE: protein (xi) SEQUENCE DESCRIPTION: SEQ ID NO: 2:

```
Met Asn Thr Glu Met Tyr Gln Thr Pro Met Glu Val Ala Val Tyr Gln
  1               5                  10                  15

Leu His Asn Phe Ser Thr Ser Phe Phe Ser Ser Leu Leu Gly Gly Asp
```

-continued

```
            20                  25                  30

Val Val Ser Val Lys Leu Asp Asn Ser Ala Ser Gly Ala Ser Val Val
        35                  40                  45

Ala Leu Asp Asn Lys Ile Glu Gln Ala Met Asp Leu Val Lys Asn His
    50                  55                  60

Leu Met Tyr Ala Val Arg Glu Glu Val Glu Val Leu Lys Glu Gln Ile
65                  70                  75                  80

Arg Glu Leu Leu Glu Lys Asn Ser Gln Leu Glu Arg Glu Asn Thr Leu
                85                  90                  95

Leu Lys Thr Leu Ala Ser Pro Glu Gln Leu Glu Lys Phe Gln Ser Arg
            100                 105                 110

Leu Ser Pro Glu Glu Pro Ala Pro Glu Ala Pro Glu Thr Pro Glu Thr
        115                 120                 125

Pro Glu Ala Pro Gly Gly Ser Ala Val
    130                 135
```

(2) INFORMATION FOR SEQ ID NO: 3:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: misc_feature
(B) LOCATION:1..20
(D) OTHER INFORMATION:/note= “PCR forward primer”

(xi) SEQUENCE DESCRIPTION: SEQ ID NO: 3:

CCATCTGGGT CCACTCCAGT 20

(2) INFORMATION FOR SEQ ID NO: 4:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (ix) FEATURE:
(A) NAME/KEY: misc_feature
(B) LOCATION:1..20
(D) OTHER INFORMATION:/note= “PCR reverse primer”

(xi) SEQUENCE DESCRIPTION: SEQ ID NO: 4:

AGGACAGTGG GAGTGGCACC 20

(2) INFORMATION FOR SEQ ID NO: 5:

(i) SEQUENCE CHARACTERISTICS:
(A) LENGTH: 1946 base pairs
(B) TYPE: nucleic acid
(C) STRANDEDNESS: single
(D) TOPOLOGY: linear (ii) MOLECULE TYPE: cDNA -continued (iii) HYPOTHETICAL: NO (iv) ANTI-SENSE: NO (ix) FEATURE:
(A) NAME/KEY: CDS
(B) LOCATION:241..642

(xi) SEQUENCE DESCRIPTION: SEQ ID NO: 5:

```
AATTCGGGGG CCGTGGAGTT TGTGACATAC GAGGTGACAC CCCTCGAGTC ACTTCCCTTC     60

AACTCCAGCT GGAGCGCCTG CTTGGCTTTG GGTTCGTTCT GCAGCCTTCG CCCCGCTCCT    120

AGCCTCAGGG CCGGACTCCA GCGCAGAGCC CAGCCCAGCG CAGCCTGCCA GCAGCCACCC    180

AGCCGCCCAG CCGCCCAGCC CCGCACGAAA CCCGGCCAGA GCTTCCTAGC AGCCCGAGCC    240

ATG AAC ACC GAA ATG TAT CAG ACC CCC ATG GAG GTG GCG GTC TAC CAG      288
Met Asn Thr Glu Met Tyr Gln Thr Pro Met Glu Val Ala Val Tyr Gln
                5                  10                  15

CTG CAC AAT TTC TCC ATC TCC TTC TTC TCT TCT CTG CTT GGA GGG GAT      336
Leu His Asn Phe Ser Ile Ser Phe Phe Ser Ser Leu Leu Gly Gly Asp
            20                  25                  30

GTG GTT TCC GTT AAG CTG GAC AAC AGT GCC TCC GGA GCC AGC GTG GTG      384
Val Val Ser Val Lys Leu Asp Asn Ser Ala Ser Gly Ala Ser Val Val
        35                  40                  45

GCC ATA GAC AAC AAG ATC GAA CAG GCC ATG GAT CTG GTG AAG AAT CAT      432
Ala Ile Asp Asn Lys Ile Glu Gln Ala Met Asp Leu Val Lys Asn His
    50                  55                  60

CTG ATG TAT GCT GTG AGA GAG GAG GTG GAG ATC CTG AAG GAG CAG ATC      480
Leu Met Tyr Ala Val Arg Glu Glu Val Glu Ile Leu Lys Glu Gln Ile
65                  70                  75                  80

CGA GAG CTG GTG GAG AAG AAC TCC CAG CTA GAG CGT GAG AAC ACC CTG      528
Arg Glu Leu Val Glu Lys Asn Ser Gln Leu Glu Arg Glu Asn Thr Leu
                85                  90                  95

TTG AAG ACC CTG GCA AGC CCA GAG CAG CTG GAG AAG TTC CAG TCC TGT      576
Leu Lys Thr Leu Ala Ser Pro Glu Gln Leu Glu Lys Phe Gln Ser Cys
            100                 105                 110

CTG AGC CCT GAA GAG CCA GCT CCC GAA TCC CCA CAA GTG CCC GAG GCC      624
Leu Ser Pro Glu Glu Pro Ala Pro Glu Ser Pro Gln Val Pro Glu Ala
        115                 120                 125

CCT GGT GGT TCT GCG GTG TAAGTGGCTC TGTCCTCAGG GTGGGCAGAG             672
Pro Gly Gly Ser Ala Val
    130

CCACTAAACT TGTTTTACCT AGTTCTTTCC AGTTTGTTTT TGGCTCCCCA AGCATCATCT    732

CACGAGGAGA ACTTTACACC TAGCACAGCT GGTGCCAAGA GATGTCCTAA GGACATGGCC    792

ACCTGGGTCC ACTCCAGCGA CAGACCCCTG ACAAGAGCAG GTCTCTGGAG GCTGAGTTGC    852

ATGGGGCCTA GTAACACCAA GCCAGTGAGC CTCTAATGCT ACTGCGCCCT GGGGGCTCCC    912

AGGGCCTGGG CAACTTAGCT GCAACTGGCA AAGGAGAAGG GTAGTTTGAG GTGTGACACC    972

AGTTTGCTCC AGAAAGTTTA AGGGGTCTGT TTCTCATCTC CATGGACATC TTCAACAGCT   1032

TCACCTGACA ACGACTGTTC CTATGAAGAA GCCACTTGTG TTTTAAGCAG AGGCAACCTC   1092

TCTCTTCTCC TCTGTTTCGT GAAGGCAGGG GACACAGATG GGAGAGATTG AGCCAAGTCA   1152

GCCTTCTGTT GGTTAATATG GTATAATGCA TGGCTTTGTG CACAGCCCAG TGTGGGATTA   1212

CAGCTTTGGG ATGACCGCTT ACAAAGTTCT GTTTGGTTAG TATTGGCATA GTTTTTCTAT   1272

ATAGCCATAA ATGCGTATAT ATACCCATAG GGCTAGATCT GTATCTTAGT GTAGCGATGT   1332

ATACATATAC ACATCCACCT ACATGTTGAA GGGCCTAACC AGCCTTGGGA GTATTGACTG   1392
```

-continued

```
GTCCCTTACC TCTTATGGCT AAGTCTTTGA CTGTGTTCAT TTACCAAGTT GACCCAGTTT   1452

GTCTTTTAGG TTAAGTAAGA ACTCGAGAGT AAAGGCAAGG AGGGGGGCCA GCCTCTGAAT   1512

GCGGCCACGG ATGCCTTGCT GCTGCAACCC TTTCCCCAGC TGTCCACTGA AACGTGAAGT   1572

CCTGTTTTGA ATGCCAAACC CACCATTCAC TGGTGCTGAC TACATAGAAT GGGTTGAGAG   1632

AAGATCAGTT TGGGCTTCAC AGTGTCATTT GAAAAAGCGT TTTTGTTTTG TTTTGAATTA   1692

TTGTGGAAAA CTTTCAAGTG AACAGAAGGA TGGTGTCCTA CTGTGGATGA GGGATGAACA   1752

AGGGGATGGC TTTGATCCAA TGGAGCCTGG GAGGTGTGCC CAGAAAGCTT GTCTGTAGCG   1812

GGTTTTGTGA GAGTGAACAC TTTCCACTTT TTGACACCTT ATCCTGATGT ATGGTTCCAG   1872

GATTTGGATT TTGATTTTCC AAATGTAGCT TGAAATTTCA ATAAACTTTG CTCTGTTTTT   1932

CTAAAAAATA AAAA                                                     1946
```

(2) INFORMATION FOR SEQ ID NO: 6:

(i) SEQUENCE CHARACTERISTICS:
(A) LENGTH: 134 amino acids
(B) TYPE: amino acid
(D) TOPOLOGY: linear (ii) MOLECULE TYPE: protein (xi) SEQUENCE DESCRIPTION: SEQ ID NO: 6:

```
Met Asn Thr Glu Met Tyr Gln Thr Pro Met Glu Val Ala Val Tyr Gln
  1               5                  10                  15

Leu His Asn Phe Ser Ile Ser Phe Phe Ser Ser Leu Leu Gly Gly Asp
             20                  25                  30

Val Val Ser Val Lys Leu Asp Asn Ser Ala Ser Gly Ala Ser Val Val
         35                  40                  45

Ala Ile Asp Asn Lys Ile Glu Gln Ala Met Asp Leu Val Lys Asn His
     50                  55                  60

Leu Met Tyr Ala Val Arg Glu Glu Val Glu Ile Leu Lys Glu Gln Ile
 65                  70                  75                  80

Arg Glu Leu Val Glu Lys Asn Ser Gln Leu Glu Arg Glu Asn Thr Leu
                 85                  90                  95

Leu Lys Thr Leu Ala Ser Pro Glu Gln Leu Glu Lys Phe Gln Ser Cys
            100                 105                 110

Leu Ser Pro Glu Glu Pro Ala Pro Glu Ser Pro Gln Val Pro Glu Ala
        115                 120                 125

Pro Gly Gly Ser Ala Val
    130
```

(2) INFORMATION FOR SEQ ID NO: 7:

(i) SEQUENCE CHARACTERISTICS:
(A) LENGTH: 26 amino acids
(B) TYPE: amino acid
(D) TOPOLOGY: linear (ii) MOLECULE TYPE: pepetide (xi) SEQUENCE DESCRIPTION: SEQ ID NO: 7:

```
Leu Lys Glu Gln Ile Lys Glu Leu Ile Glu Lys Asn Ser Gln Leu Glu
  1               5                  10                  15

Gln Glu Asn Asp Leu Leu Lys Thr Leu Ala
             20                  25
```

(2) INFORMATION FOR SEQ ID NO: 8:

-continued (i) SEQUENCE CHARACTERISTICS:
(A) LENGTH: 26 amino acids
(B) TYPE: amino acid
(D) TOPOLOGY: linear (ii) MOLECULE TYPE: peptide (xi) SEQUENCE DESCRIPTION: SEQ ID NO: 8:

```
Leu Glu Asp Lys Val Glu Glu Leu Leu Ser Lys Asn Tyr His Leu Glu
  1               5                  10                  15

Asn Glu Val Ala Arg Leu Lys Lys Leu Val
             20                  25
```

(2) INFORMATION FOR SEQ ID NO: 9:

(i) SEQUENCE CHARACTERISTICS:
(A) LENGTH: 26 amino acids
(B) TYPE: amino acid
(D) TOPOLOGY: linear (ii) MOLECULE TYPE: peptide (xi) SEQUENCE DESCRIPTION: SEQ ID NO: 9:

```
Leu Glu Asn Arg Val Ala Val Leu Glu Asn Gln Asn Lys Thr Leu Ile
  1               5                  10                  15

Glu Glu Leu Lys Ala Leu Lys Asp Leu Tyr
             20                  25
```

(2) INFORMATION FOR SEQ ID NO: 10:

(i) SEQUENCE CHARACTERISTICS:
(A) LENGTH: 26 amino acids
(B) TYPE: amino acid
(D) TOPOLOGY: linear (ii) MOLECULE TYPE: peptide (xi) SEQUENCE DESCRIPTION: SEQ ID NO: 10:

```
Leu Glu Asn Arg Val Ala Val Leu Glu Asn Gln Asn Lys Thr Leu Ile
  1               5                  10                  15

Glu Glu Leu Lys Ala Leu Lys Asp Leu Tyr
             20                  25
```

(2) INFORMATION FOR SEQ ID NO: 11:

(i) SEQUENCE CHARACTERISTICS:
(A) LENGTH: 26 amino acids
(B) TYPE: amino acid
(D) TOPOLOGY: linear (ii) MOLECULE TYPE: peptide (xi) SEQUENCE DESCRIPTION: SEQ ID NO: 11:

```
Leu Glu Glu Lys Val Lys Thr Leu Lys Ala Gln Asn Ser Glu Leu Ala
  1               5                  10                  15

Ser Thr Ala Asn Met Leu Arg Glu Gln Val
             20                  25
```

(2) INFORMATION FOR SEQ ID NO: 12:

(i) SEQUENCE CHARACTERISTICS:
(A) LENGTH: 77 amino acids
(B) TYPE: amino acid
(D) TOPOLOGY: linear (ii) MOLECULE TYPE: protein -continued (xi) SEQUENCE DESCRIPTION: SEQ ID NO: 12:

```
Met Asp Leu Val Lys Asn His Leu Met Tyr Ala Val Arg Glu Glu Val
  1               5                  10                  15

Glu Ile Leu Lys Glu Gln Ile Arg Glu Leu Val Glu Lys Asn Ser Gln
             20                  25                  30

Leu Glu Arg Glu Asn Thr Leu Leu Lys Thr Leu Ala Ser Pro Glu Gln
         35                  40                  45

Leu Glu Lys Phe Gln Ser Cys Leu Ser Pro Glu Glu Pro Ala Pro Glu
     50                  55                  60

Ser Pro Gln Val Pro Glu Ala Pro Gly Gly Ser Ala Val
 65                  70                  75
```

(2) INFORMATION FOR SEQ ID NO: 13:

(i) SEQUENCE CHARACTERISTICS:
(A) LENGTH: 143 amino acids
(B) TYPE: amino acid
(D) TOPOLOGY: linear (ii) MOLECULE TYPE: protein (xi) SEQUENCE DESCRIPTION: SEQ ID NO: 13:

```
Lys Ser Gln Trp Cys Arg Pro Val Ala Met Asp Leu Gly Val Tyr Gln
  1               5                  10                  15

Leu Arg His Phe Ser Ile Ser Phe Leu Ser Ser Leu Leu Gly Thr Glu
             20                  25                  30

Asn Ala Ser Val Arg Leu Asp Asn Ser Ser Ser Gly Ala Ser Val Val
         35                  40                  45

Ala Ile Asp Asn Lys Ile Glu Gln Ala Met Asp Leu Val Lys Ser His
     50                  55                  60

Leu Met Tyr Ala Val Arg Glu Glu Val Glu Val Leu Lys Glu Gln Ile
 65                  70                  75                  80

Lys Glu Leu Ile Glu Lys Asn Ser Gln Leu Glu Gln Glu Asn Asn Leu
                 85                  90                  95

Leu Lys Thr Leu Ala Ser Pro Glu Gln Leu Ala Gln Phe Gln Ala Gln
            100                 105                 110

Leu Gln Thr Gly Ser Pro Pro Ala Thr Thr Gln Pro Gln Gly Thr Thr
        115                 120                 125

Gln Pro Pro Ala Gln Pro Ala Ser Gln Gly Ser Gly Pro Thr Ala
    130                 135                 140
```

(2) INFORMATION FOR SEQ ID NO: 14:

(i) SEQUENCE CHARACTERISTICS:
(A) LENGTH: 4 amino acids
(B) TYPE: amino acid
(D) TOPOLOGY: linear (ii) MOLECULE TYPE: peptide (ix) FEATURE:
(D) OTHER INFORMATION:/note= "the N-terminus is modified by an acetyl group; the C-terminus is modified with a-(4-methyl-coumaryl-7-amide)"

(xi) SEQUENCE DESCRIPTION: SEQ ID NO: 14:

Asp Glu Val Asp (2) INFORMATION FOR SEQ ID NO: 15:

-continued

```
  (i) SEQUENCE CHARACTERISTICS:
       (A) LENGTH: 4 amino acids
       (B) TYPE: amino acid
       (D) TOPOLOGY: linear

 (ii) MOLECULE TYPE: peptide

 (ix) FEATURE:
       (D) OTHER INFORMATION:/note= "the N-terminus is modified by an
            acetyl group; the C-terminus is modified with
            CH2OC(O)-[2,6-(CF3)2]Ph"

 (xi) SEQUENCE DESCRIPTION: SEQ ID NO: 15:

Tyr Val Ala Asp
```